(12) United States Patent
Roche

(10) Patent No.: US 12,226,184 B2
(45) Date of Patent: Feb. 18, 2025

(54) METHOD FOR DETECTING BODY PARAMETERS

(71) Applicant: Martin W. Roche, Fort Lauderdale, FL (US)

(72) Inventor: Martin W. Roche, Fort Lauderdale, FL (US)

( * ) Notice: Subject to any disclaimer, the term of this patent is extended or adjusted under 35 U.S.C. 154(b) by 235 days.

(21) Appl. No.: 17/339,741

(22) Filed: Jun. 4, 2021

(65) Prior Publication Data

US 2021/0290063 A1 Sep. 23, 2021

Related U.S. Application Data

(63) Continuation of application No. 16/550,437, filed on Aug. 26, 2019, now Pat. No. 11,457,813, which is a (Continued)

(51) Int. Cl.
*A61B 5/00* (2006.01)
*A61B 5/07* (2006.01)
(Continued)

(52) U.S. Cl.
CPC ............ *A61B 5/0031* (2013.01); *A61B 5/076* (2013.01); *A61B 5/1116* (2013.01); *A61B 5/1121* (2013.01); *A61B 5/412* (2013.01); *A61B 5/447* (2013.01); *A61B 5/4504* (2013.01); *A61B 5/4509* (2013.01); *A61B 5/4528* (2013.01);
(Continued)

(58) Field of Classification Search
CPC ..... A61B 8/0875; A61B 8/565; A61B 5/0031; A61B 5/076; A61B 5/1116; A61B 5/1121; A61B 5/4528; A61B 5/686; A61B 5/4504; A61B 5/4533; A61B 2505/05; A61B 2562/046; A61B 5/116
See application file for complete search history.

(56) References Cited

U.S. PATENT DOCUMENTS

| 4,936,308 A | 6/1990 | Fukukita et al. |
| 5,197,488 A | 3/1993 | Kovacevic |
(Continued)

FOREIGN PATENT DOCUMENTS

| CN | 1420753 A | 5/2003 |
| CN | 101060815 A | 10/2007 |
(Continued)

OTHER PUBLICATIONS

Chinese Search Report of Chinese Patent App. 201510178035.9 dated Dec. 30, 2016.
(Continued)

*Primary Examiner* — Sameh R Boles
(74) *Attorney, Agent, or Firm* — Bookoff McAndrews, PLLC

(57) ABSTRACT

A method for detecting biometric parameters includes the steps of performing a bone graft procedure on at least one vertebra of a spine, providing at least one biometric sensor at the at least one vertebra, the sensor measuring at least one parameter selected from the group consisting of pressure, tension, shear, relative position, and vascular flow in an adjacent surrounding, and measuring the at least one biometric parameter at the vertebra with the sensor.

19 Claims, 52 Drawing Sheets

Related U.S. Application Data continuation of application No. 13/017,040, filed on Jan. 30, 2011, now abandoned, which is a continuation-in-part of application No. 13/015,685, filed on Jan. 28, 2011, now Pat. No. 8,449,556, and a continuation-in-part of application No. 13/014,767, filed on Jan. 27, 2011, now Pat. No. 8,372,147, and a continuation-in-part of application No. 13/014,773, filed on Jan. 27, 2011, now Pat. No. 8,372,153, and a continuation-in-part of application No. 13/014,782, filed on Jan. 27, 2011, now Pat. No. 8,444,654, and a continuation-in-part of application No. 12/748,099, filed on Mar. 26, 2010, now abandoned, and a continuation-in-part of application No. 12/748,147, filed on Mar. 26, 2010, now Pat. No. 8,906,027, and a continuation-in-part of application No. 12/748,136, filed on Mar. 26, 2010, now abandoned, and a continuation-in-part of application No. 12/748,112, filed on Mar. 26, 2010, now abandoned, and a continuation-in-part of application No. 12/748,126, filed on Mar. 26, 2010, now abandoned, and a continuation-in-part of application No. 12/604,083, filed on Oct. 22, 2009, now abandoned, and a continuation-in-part of application No. 12/604,072, filed on Oct. 22, 2009, now abandoned, and a continuation-in-part of application No. 12/604,099, filed on Oct. 22, 2009, now Pat. No. 8,099,168, and a continuation-in-part of application No. 11/391,988, filed on Mar. 29, 2006, now Pat. No. 7,918,887.

(60) Provisional application No. 61/211,023, filed on Mar. 26, 2009, provisional application No. 61/196,915, filed on Oct. 22, 2008, provisional application No. 61/196,914, filed on Oct. 22, 2008, provisional application No. 61/196,916, filed on Oct. 22, 2008, provisional application No. 60/763,869, filed on Feb. 1, 2006, provisional application No. 60/763,761, filed on Feb. 1, 2006, provisional application No. 60/665,797, filed on Mar. 29, 2005.

(51) Int. Cl.
*A61B 5/11* (2006.01)
*A61B 8/00* (2006.01)
*A61B 8/08* (2006.01)

(52) U.S. Cl.
CPC .......... *A61B 5/4533* (2013.01); *A61B 5/4561* (2013.01); *A61B 5/686* (2013.01); *A61B 8/0875* (2013.01); *A61B 8/565* (2013.01); *A61B 2505/05* (2013.01); *A61B 2560/063* (2013.01); *A61B 2562/0252* (2013.01); *A61B 2562/046* (2013.01)

(56) References Cited

U.S. PATENT DOCUMENTS

| | | | |
|---|---|---|---|
| 5,360,016 | A | 11/1994 | Kovacevic |
| 5,425,775 | A | 6/1995 | Kovacevic |
| 5,456,724 | A | 10/1995 | Yen et al. |
| 5,470,354 | A | 11/1995 | Hershberger et al. |
| 5,524,624 | A | 6/1996 | Tepper et al. |
| 5,683,396 | A | 11/1997 | Tokish et al. |
| 5,688,279 | A | 11/1997 | McNulty et al. |
| 5,702,429 | A | 12/1997 | King |
| 5,853,745 | A | 12/1998 | Darouiche |
| 5,871,018 | A | 2/1999 | Delp et al. |
| 5,873,368 | A | 2/1999 | Sabin |
| 5,921,929 | A | 7/1999 | Goll et al. |
| 6,014,588 | A | 1/2000 | Fitz |
| 6,063,091 | A | 5/2000 | Lombardo et al. |
| 6,090,114 | A | 7/2000 | Matsuno et al. |
| 6,228,089 | B1 | 5/2001 | Wahrburg et al. |
| 6,245,109 | B1 | 6/2001 | Mendes et al. |
| 6,304,766 | B1 | 10/2001 | Colvin, Jr. |
| 6,347,245 | B1 | 2/2002 | Lee et al. |
| 6,447,448 | B1 | 9/2002 | Ishikawa et al. |
| 6,493,588 | B1 | 12/2002 | Malaney et al. |
| 6,505,075 | B1 | 1/2003 | Weiner |
| 6,558,391 | B2 | 5/2003 | Axelson, Jr. et al. |
| 6,573,706 | B2 | 6/2003 | Mendes et al. |
| 6,582,365 | B1 | 6/2003 | Hines et al. |
| 6,583,630 | B2 | 6/2003 | Mendes et al. |
| 6,621,278 | B2 | 9/2003 | Ariav |
| 6,638,228 | B1 | 10/2003 | Brock-Fisher et al. |
| 6,645,214 | B2 | 11/2003 | Brown |
| 6,656,135 | B2 | 12/2003 | Zogbi et al. |
| 6,701,174 | B1 | 3/2004 | Krause et al. |
| 6,758,850 | B2 | 7/2004 | Smith et al. |
| 6,821,299 | B2 | 11/2004 | Kirking et al. |
| 6,856,141 | B2 | 2/2005 | Ariav |
| 6,920,347 | B2 | 7/2005 | Simon et al. |
| 6,925,339 | B2 | 8/2005 | Grimm et al. |
| 6,984,993 | B2 | 1/2006 | Ariav |
| 7,022,141 | B2 | 4/2006 | Dwyer et al. |
| 7,029,477 | B2 | 4/2006 | Grimm |
| 7,018,416 | B2 | 5/2006 | Hanson et al. |
| 7,080,554 | B2 | 7/2006 | Ariav |
| 7,156,853 | B2 | 1/2007 | Muratsu |
| 7,190,273 | B2 | 3/2007 | Liao et al. |
| 7,195,645 | B2 | 3/2007 | Disilvestro et al. |
| 7,206,627 | B2 | 4/2007 | Abovitz et al. |
| 7,266,989 | B2 | 9/2007 | Ariav |
| 7,313,491 | B2 | 12/2007 | Ariav |
| 7,325,460 | B2 | 2/2008 | Ariav |
| 7,325,640 | B2 | 2/2008 | Ariav |
| 7,366,562 | B2 | 4/2008 | Dukesherer et al. |
| 7,442,196 | B2 | 10/2008 | Fisher et al. |
| 7,458,977 | B2 | 12/2008 | McGinley et al. |
| 7,488,324 | B1 | 2/2009 | Metzger et al. |
| 7,520,179 | B2 | 4/2009 | Bernstein |
| 7,522,701 | B2 | 4/2009 | Jensen et al. |
| 7,525,309 | B2 | 4/2009 | Sherman et al. |
| 7,527,632 | B2 | 5/2009 | Houghton |
| 7,533,571 | B2 | 5/2009 | Ariav |
| 7,542,791 | B2 | 6/2009 | Mire et al. |
| 7,547,307 | B2 | 6/2009 | Carson et al. |
| 7,578,821 | B2 | 8/2009 | Fisher et al. |
| 7,606,613 | B2 | 10/2009 | Simon et al. |
| 7,710,124 | B2 | 5/2010 | Ariav |
| 7,716,988 | B2 | 5/2010 | Ariav |
| 2002/0010390 | A1 | 1/2002 | Guice et al. |
| 2002/0029784 | A1 | 3/2002 | Stark |
| 2002/0107537 | A1 | 8/2002 | Singh |
| 2002/0107573 | A1 | 8/2002 | Steinberg |
| 2002/0147416 | A1 | 10/2002 | Zogbi et al. |
| 2002/0151770 | A1 | 10/2002 | Noll et al. |
| 2002/0183628 | A1 | 12/2002 | Reich et al. |
| 2003/0187348 | A1 | 10/2003 | Goodwin |
| 2003/0229388 | A1 | 12/2003 | Hayashi et al. |
| 2004/0006263 | A1 | 1/2004 | Anderson et al. |
| 2004/0019382 | A1 | 1/2004 | Amirouche et al. |
| 2004/0054302 | A1 | 3/2004 | Czernicki |
| 2004/0127793 | A1 | 7/2004 | Mendlein et al. |
| 2004/0186396 | A1 | 9/2004 | Shuvo et al. |
| 2004/0186576 | A1 | 9/2004 | Biscup et al. |
| 2005/0010301 | A1 | 1/2005 | Disilvestro et al. |
| 2005/0012610 | A1 | 1/2005 | Liao et al. |
| 2005/0015002 | A1 | 1/2005 | Dixon et al. |
| 2005/0020941 | A1 | 1/2005 | Tarabichi |
| 2005/0021044 | A1* | 1/2005 | Stone .................. A61B 17/175 606/102 |
| 2005/0027206 | A1 | 2/2005 | Ariav |
| 2005/0107866 | A1* | 5/2005 | Brown ................. A61B 5/0031 623/1.1 |
| 2005/0176823 | A1 | 8/2005 | Diaz |
| 2005/0273170 | A1 | 12/2005 | Navarro et al. |
| 2006/0004431 | A1 | 1/2006 | Fuller et al. |

(56) References Cited

U.S. PATENT DOCUMENTS

| | | | |
|---|---|---|---|
| 2006/0030852 A1* | 2/2006 | Sevrain | A61B 17/72 606/328 |
| 2006/0036324 A1 | 2/2006 | Sachs et al. | |
| 2006/0046664 A1 | 3/2006 | Paradiso et al. | |
| 2006/0052782 A1* | 3/2006 | Morgan | A61B 5/14539 606/60 |
| 2006/0058790 A1* | 3/2006 | Carl | A61B 17/70 606/248 |
| 2006/0058798 A1 | 3/2006 | Roman | |
| 2006/0093646 A1 | 5/2006 | Cima | |
| 2006/0204738 A1 | 9/2006 | Dubrow | |
| 2006/0232408 A1 | 10/2006 | Nycz | |
| 2006/0246103 A1 | 11/2006 | Ralph et al. | |
| 2006/0247773 A1* | 11/2006 | Stamp | A61B 5/11 623/17.11 |
| 2006/0271112 A1 | 11/2006 | Martinson | |
| 2006/0287598 A1* | 12/2006 | Lasater | A61F 2/86 600/439 |
| 2007/0134287 A1 | 6/2007 | Troxel | |
| 2007/0179409 A1 | 8/2007 | Roy | |
| 2007/0219561 A1 | 9/2007 | Lavallee et al. | |
| 2007/0238992 A1 | 10/2007 | Donofrio | |
| 2007/0272747 A1 | 11/2007 | Woods | |
| 2008/0287856 A1 | 11/2008 | MacDonald | |
| 2008/0300481 A1 | 12/2008 | Groszmann | |
| 2008/0312530 A1 | 12/2008 | Malackowski | |
| 2009/0000627 A1 | 1/2009 | Quaid | |
| 2009/0105557 A1 | 4/2009 | Najafi | |
| 2009/0187120 A1 | 7/2009 | Nycz | |
| 2010/0204551 A1 | 8/2010 | Roche | |
| 2010/0204802 A1 | 8/2010 | Wilson et al. | |

FOREIGN PATENT DOCUMENTS

| | | |
|---|---|---|
| JP | 2000-126213 | 5/2000 |
| JP | 2004-154231 | 6/2004 |
| JP | 2005052642 | 3/2005 |
| SU | 260230 | 12/1969 |
| WO | 199628069 A1 | 9/1996 |
| WO | 199726833 A1 | 7/1997 |
| WO | 00/18294 A1 | 4/2000 |
| WO | 200038572 A1 | 7/2000 |
| WO | 2004057279 A1 | 8/2000 |
| WO | 200137733 A2 | 5/2001 |
| WO | 200215769 A2 | 2/2002 |
| WO | 2002087435 A1 | 11/2002 |
| WO | 2005120203 A2 | 12/2005 |

OTHER PUBLICATIONS

International Search Report and Written Opinion of PCT/US12/23158 dated May 16, 2012.
Australian Patent Examination Report for Application No. 2012203891 dated Apr. 8, 2014.
European Search Report for European Patent App. No. 15 16 456 dated Aug. 6, 2015.
Subsequent Examination Report issued Nov. 10, 2014, by the Government of Indian Patent Office, in IN Application No. 3729//KOLNP/2007.
Examiner's First Report issued Jan. 10, 2011 by the Australian Patert Office, in AU Patent Application No. 2006230176.
Examiner's Second Report issued Oct. 31, 2011 by the Australian Patent Office, in AU Patent Application No. 2006230176.
Office Action issued Aug. 20, 2013 by the Canadian Intellectual Property Office in CA Patent Application No. 2,600,613.
Office Action issued Jun. 5, 2014 by the Canadian Intellectual Property Office in CA Patent Application No. 2,600,613.
Office Action issued Aug. 7, 2009 by the State Intellectual Property Ofice of the People's Republic of China in CN Patent Application No. 2006800144919.

Office Action issued Jan. 22, 2010 by the State Intellectual Property Office of the People's Republic of China in CN Patent Application No. 2006800144919.
Office Action issued Apr. 19, 2013 by the State Intellectual Property Office of the People's Republic of China in CN Patent Application No. 2006800144919.
Office Action issued Jul. 24, 2013 by the State Intellectual Property Office of the People's Republic of China in CN Patent Application No. 2006800144919.
Office Action issued Nov. 1, 2013 by the State Intellectual Property Office of the People's Republic of China in CN Patent Application No. 2006800144919.
Ofice Action issued Mar. 21, 2014 by the State Intellectual Property Office of the People's Republic of China in CN Patent Application No. 2006800144919.
Extended European Search Report issued Mar. 23, 2010 by the European Patent Office in EP Patent Application No. 06748811.4.
Official Communication issued Jul. 5, 2011 by the European Patent Office in EP Patent Application No. 06748811.4.
Official Communication issued Feb. 20, 2012 by the European Patent Office in EP Patent Application No. 06748811.4.
Extended European Search Report issued Oct. 26, 2012 by the European Patent Office in EP Patent Application No. 12005171.9.
Official Communication issued Apr. 23, 2014 by the European Patent Office in EP Patent Application No. 12005171.9.
Official Communication issued Dec. 9, 2014 by the European Patent Office in EP Patent Application No. 12005171.9.
Extended European Search Report issued Oct. 26, 2012 by the European Patent Ofice in EP Patent Application No. 12005170.1.
Official Communication issued Jul. 3, 2013 by the European Patent Office in EP Patent Application No. 12005170.1.
Official Communication issued Apr. 22, 2014 by the European Patent Office in EP Patent Application No. 12005170.1.
First Examination Report issued Dec. 5, 2013 by the Government of India Patent Office, in IN Patent Application No. 3729/KOLNP/2007.
Notice of Rejection issued Oct. 25, 2011 by the Japanese Patent Office, in JP Patent Application No. 2008-504250.
Notice of Rejection issued Jun. 26, 2012 by the Japanese Patent Office, in JP Patent Application No. 2008-504250.
Decision of Rejection issued May 7, 2013 by the Japanese Patent Office, in JP Patent Application No. 2008-504250.
Notice of Rejection issued Jan. 28, 2014 by the Japanese Patent Office, in JP Patent Application No. 2012-237156.
Decision of Rejection issued Sep. 9, 2014 by the Japanese Patent Office, in JP Patent Application No. 2012-237156.
Notice of Grounds for Rejection issued Sep. 25, 2012 by the Korean Intellectual Property Office, in KR Patent Application No. 2007-7024121.
Notice Final Rejection issued Mar. 12, 2013 by the Korean Intellectual Property Office, in KR Patent Application No. 2007-7024121.
First Official Action, issue date unknown, by the Russian Patent Office, in RU Patent Application No. 2007136825/14.
Second Oficial Action, issue date unknown, by the Russian Patent Office, in RU Patent Application No. 2007136825/14.
First Office Action, issue Jan. 30, 2013, by the Russian Patent Office, in RU Patent Application No. 2011137823/14 (now abandoned).
Second Office Action, issue Aug. 1, 2013, by the Russian Patent Office, in RU Patent Application No. 2011137823/14 (now abandoned).
Notification on Patentability, issue Feb. 3, 2013, by the Russian Patent Office, in RU Patent Application No. 2011137823/14 (now abandoned).
Examination Report issued Oct. 20, 2008, by the UK Intellectual Property Office, in GB Patent Application No. 0719382.4.
Examination Report issued Apr. 22, 2009, by the UK Intellectual Property Office, in GB Patent Application No. 0719382.4.

* cited by examiner

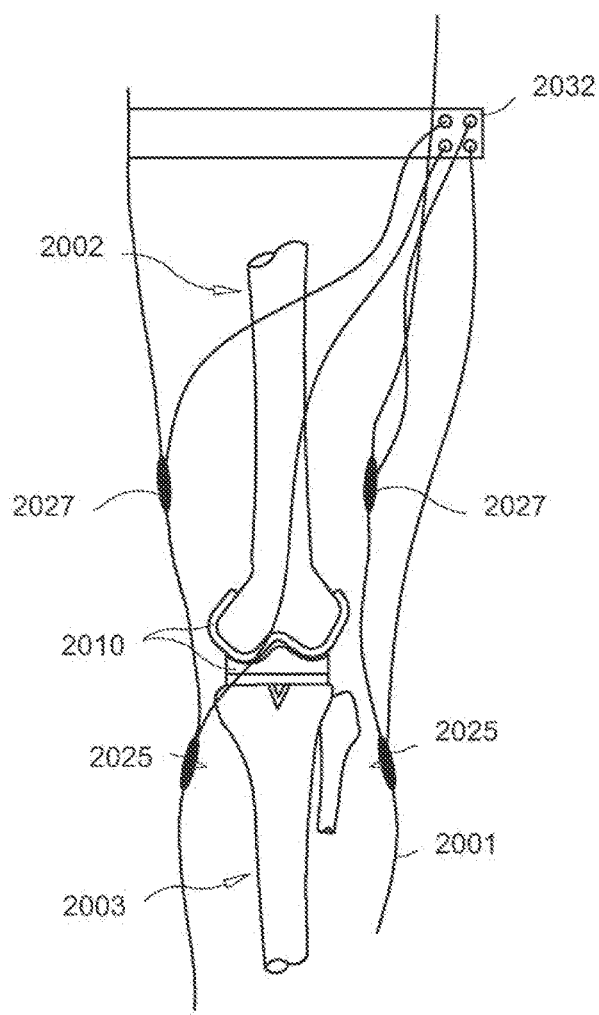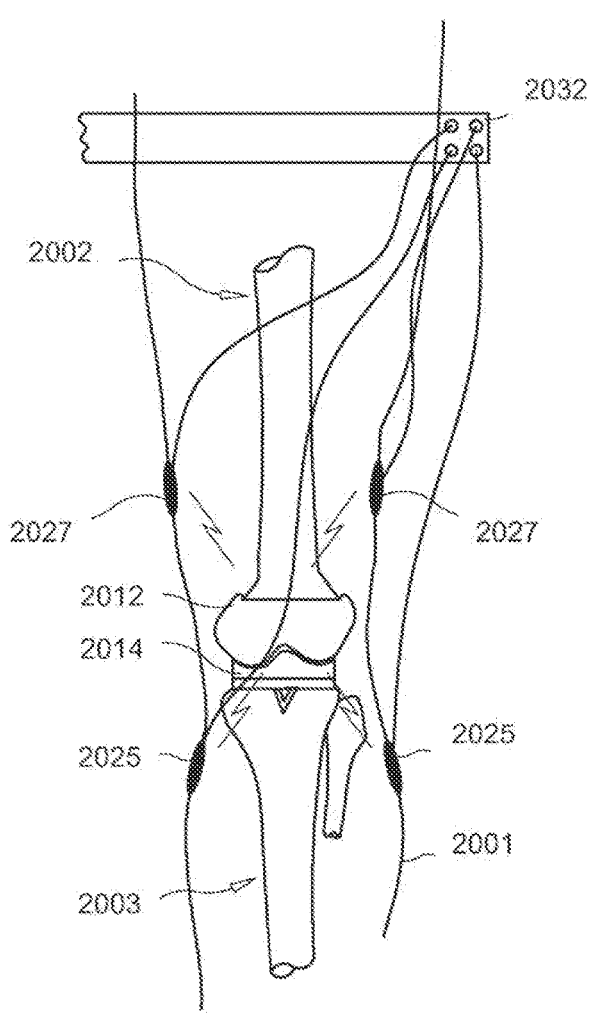

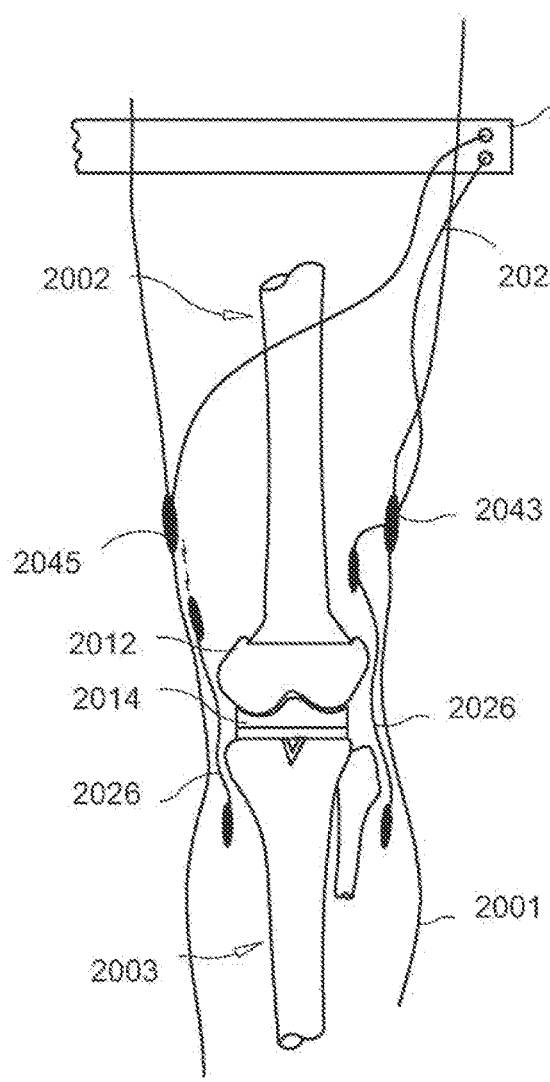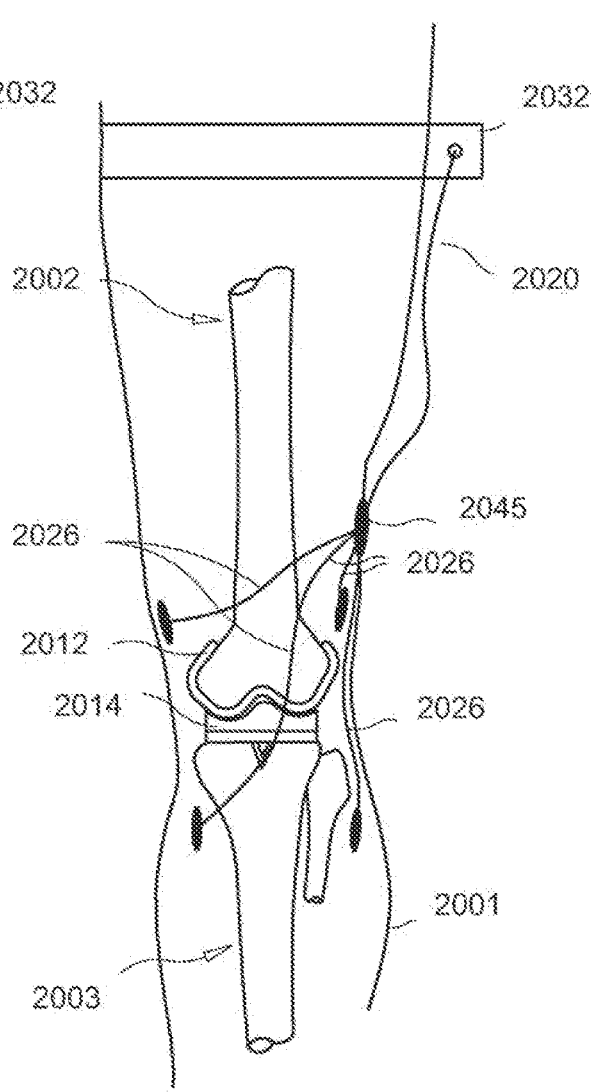

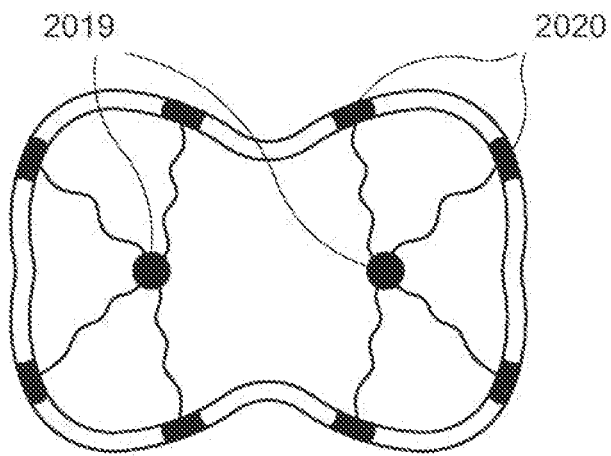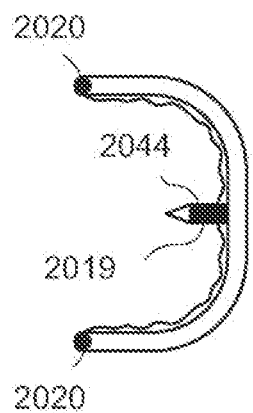
FIG. 26a  FIG. 26b
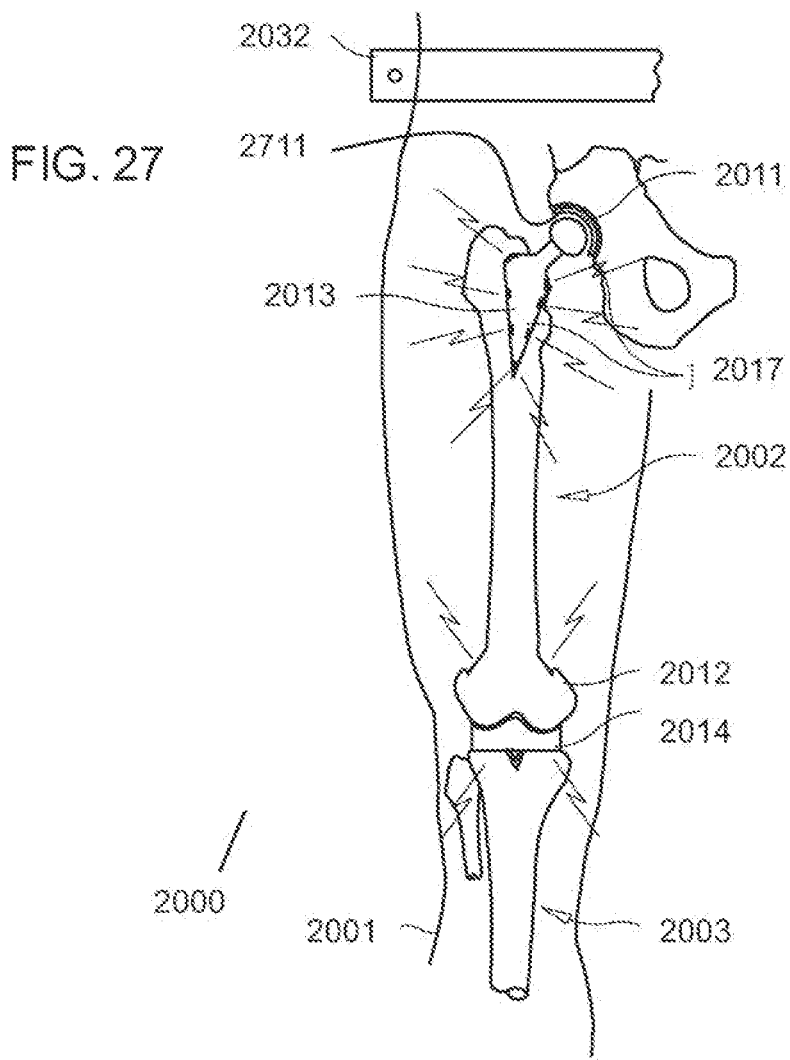
FIG. 27

Acetabulum Component

Femoral Component

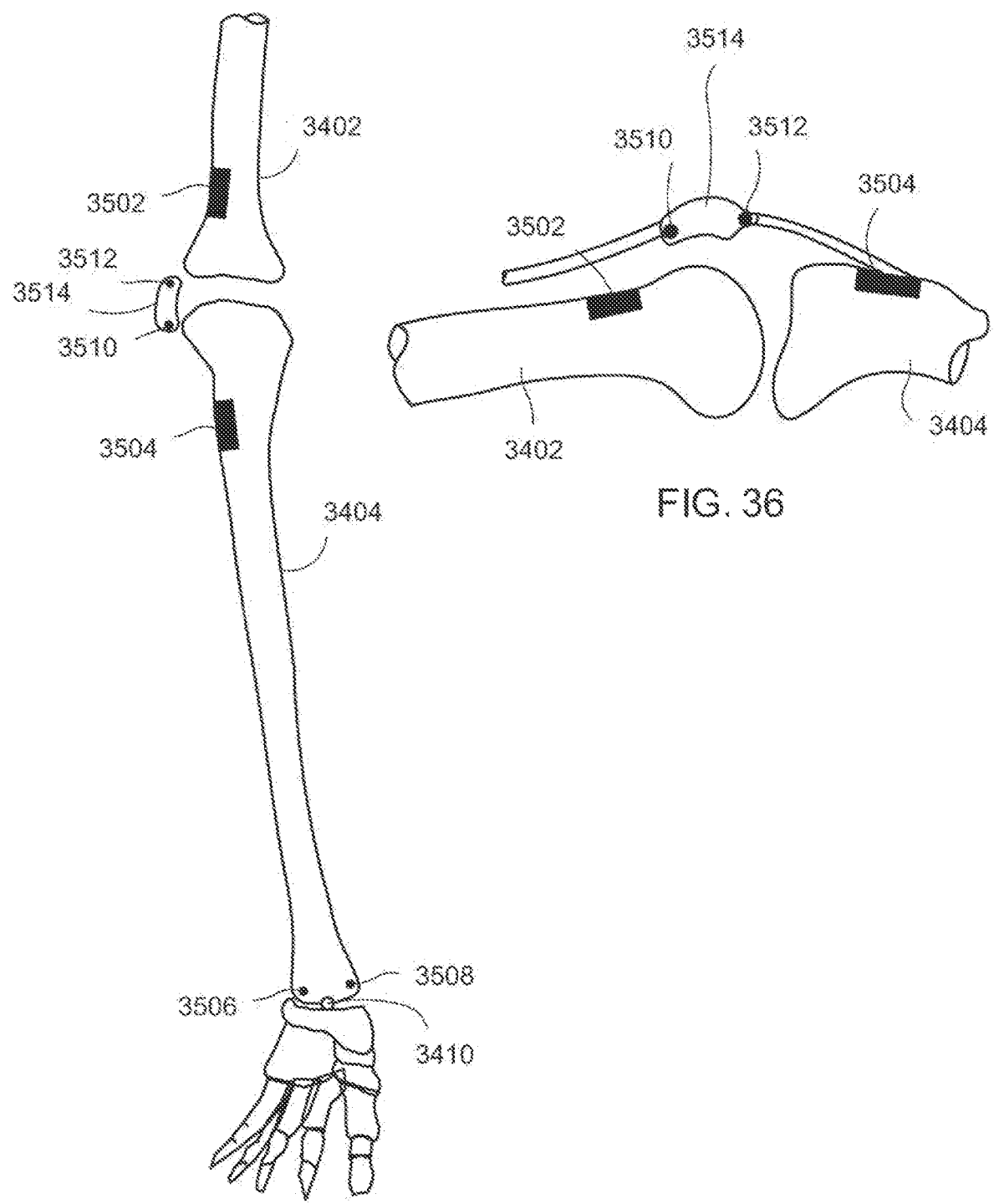

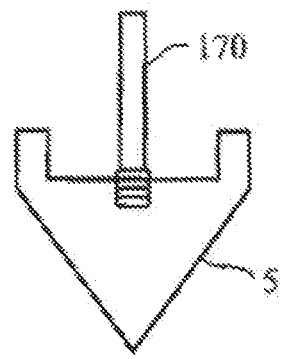 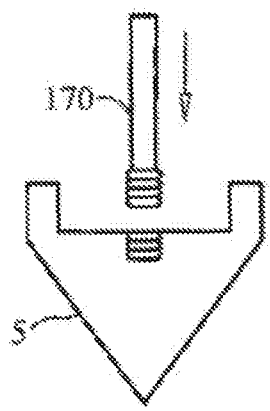
FIG. 46  FIG. 47
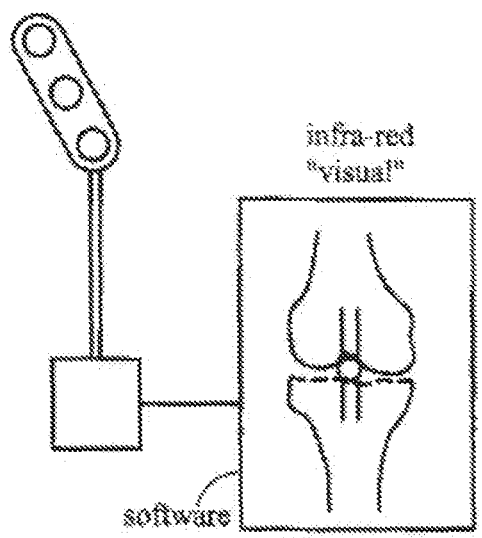 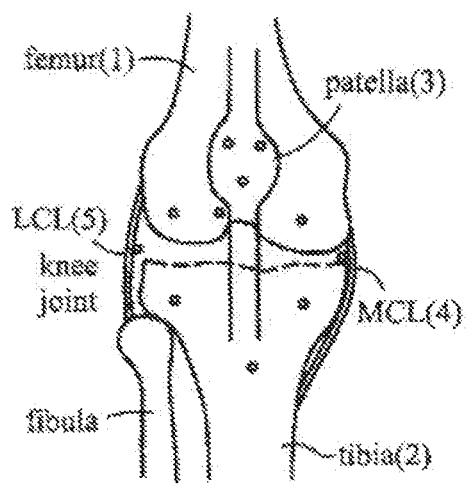
FIG. 48  FIG. 50

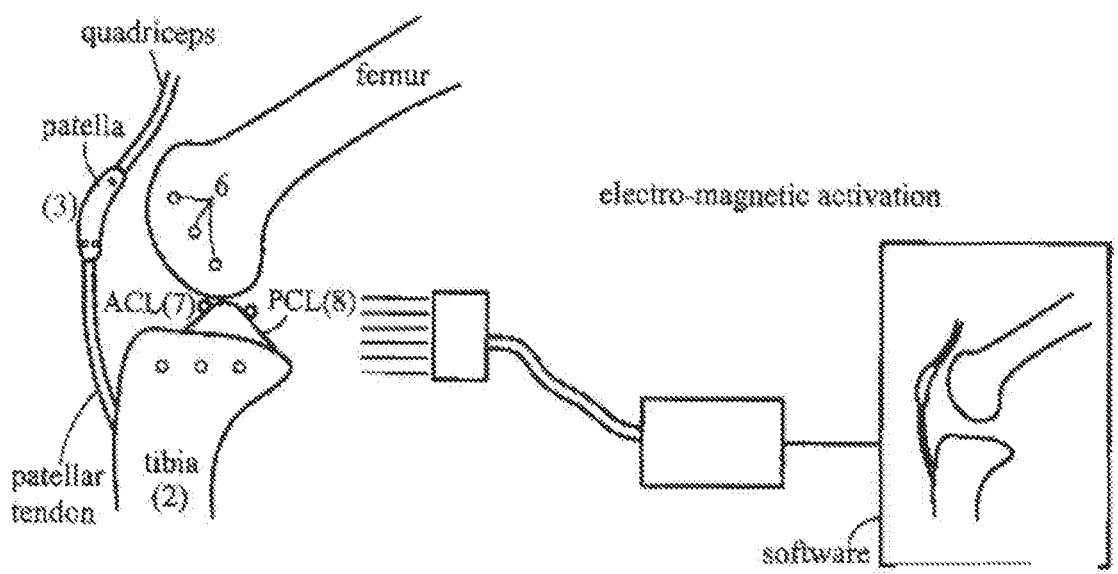
FIG. 51
FIG. 49
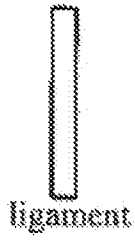
FIG. 52
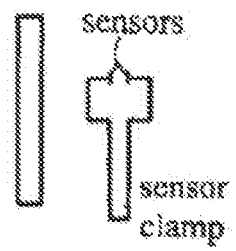
FIG. 53
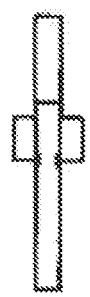
FIG. 54
FIG. 55

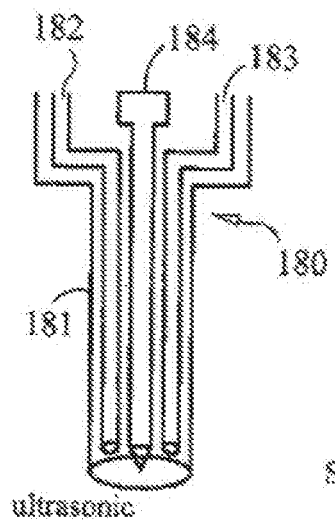
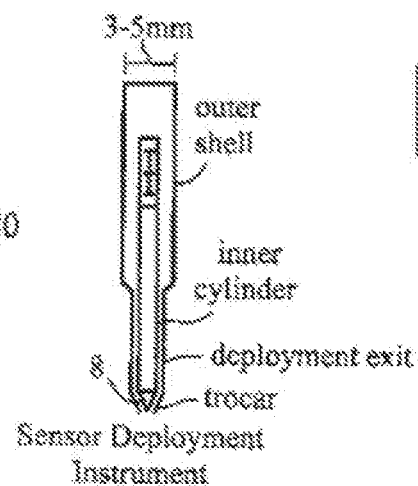
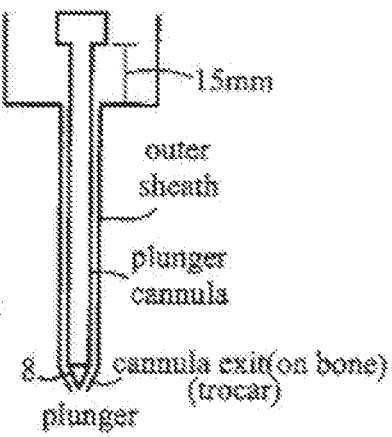
FIG. 67  FIG. 68  FIG. 69
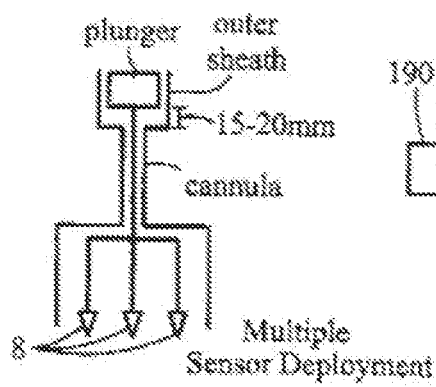
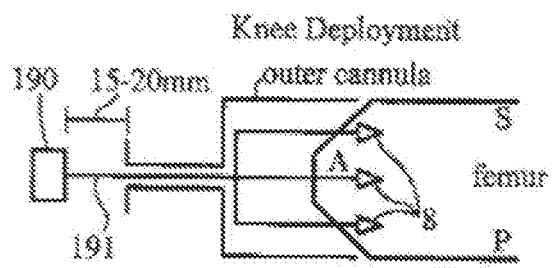
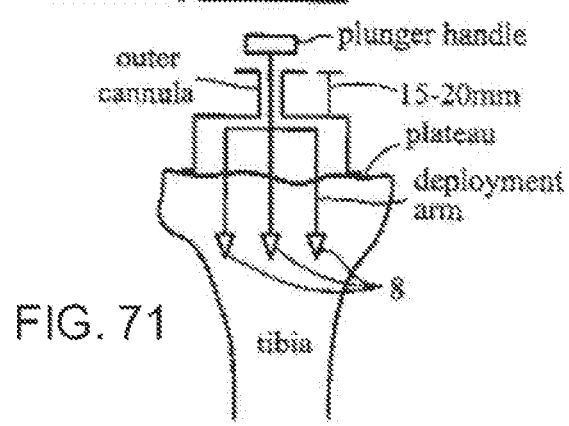
FIG. 70  FIG. 71

FIG. 86
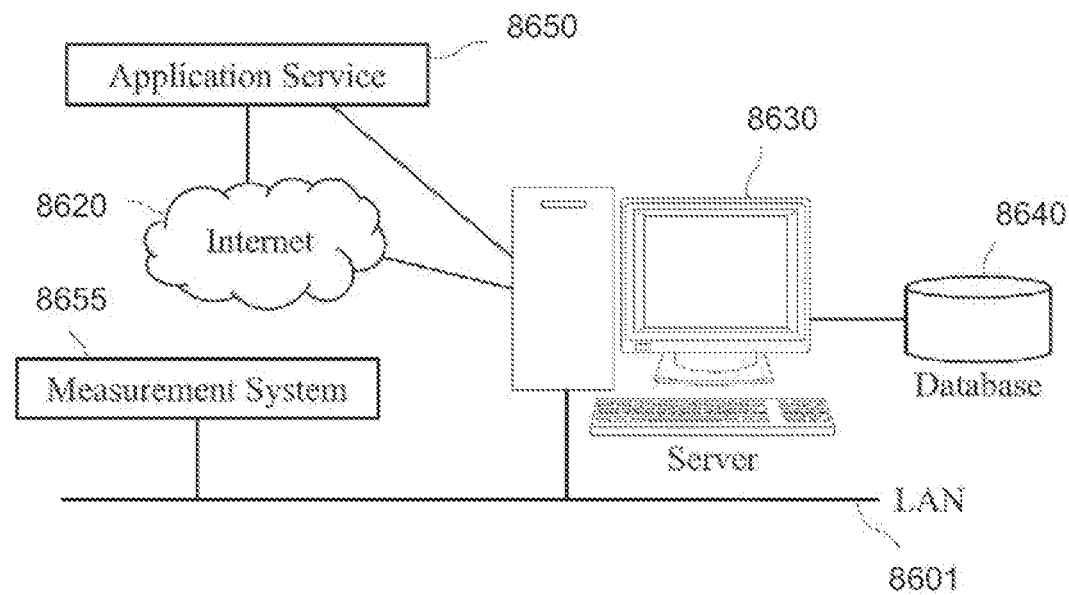
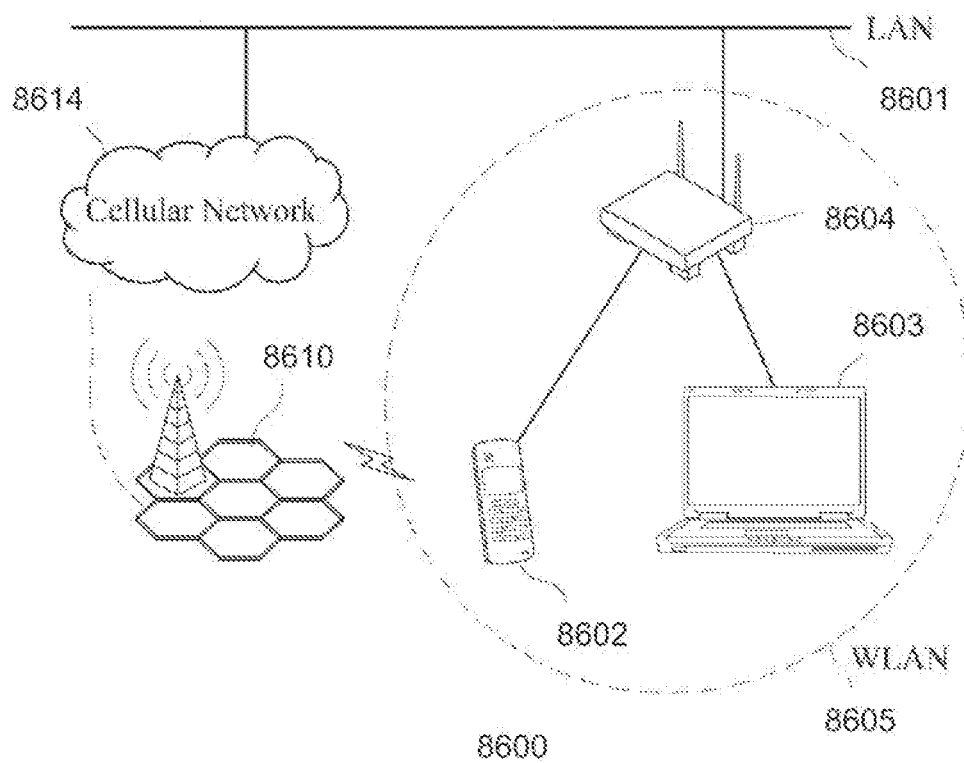

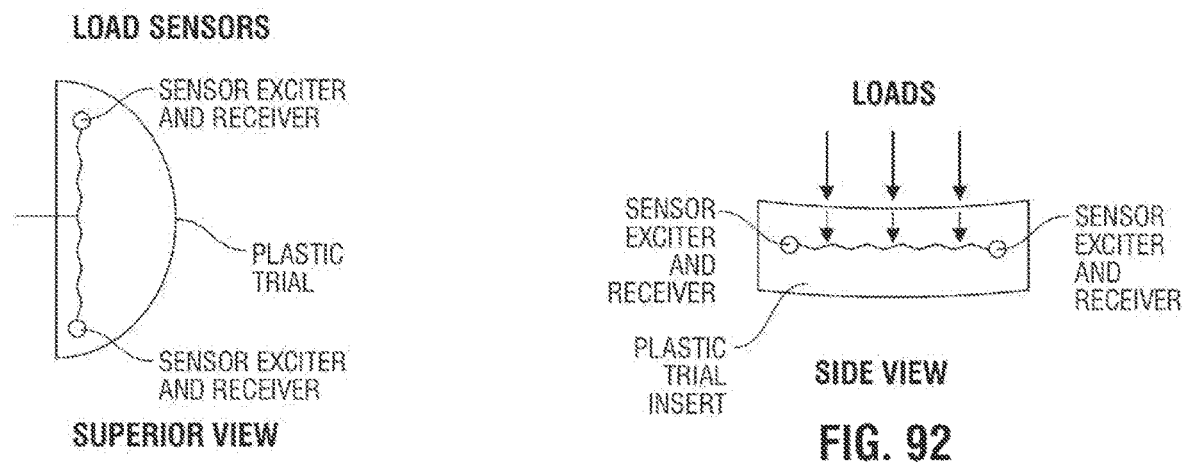
FIG. 91
FIG. 92
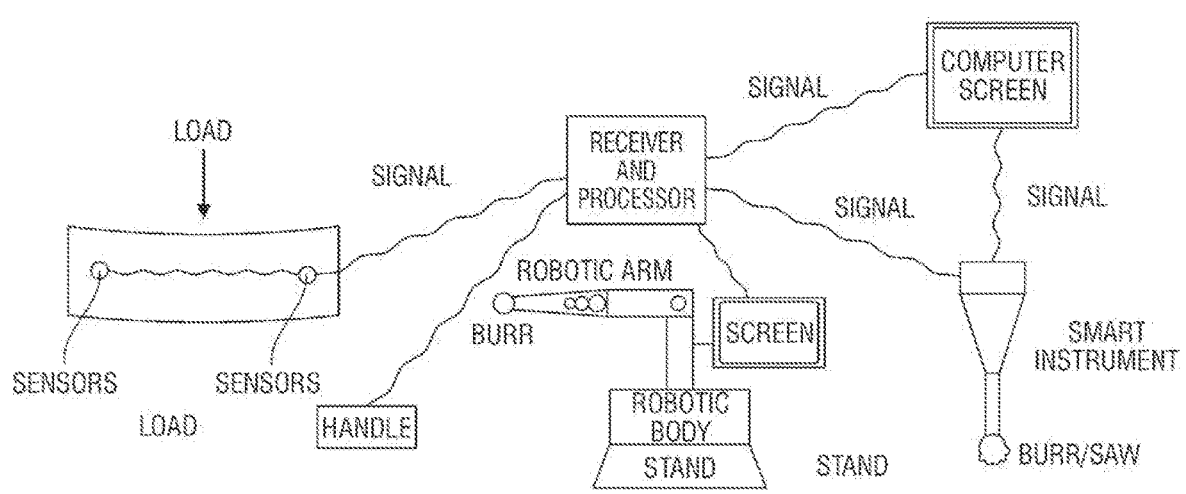
FIG. 93

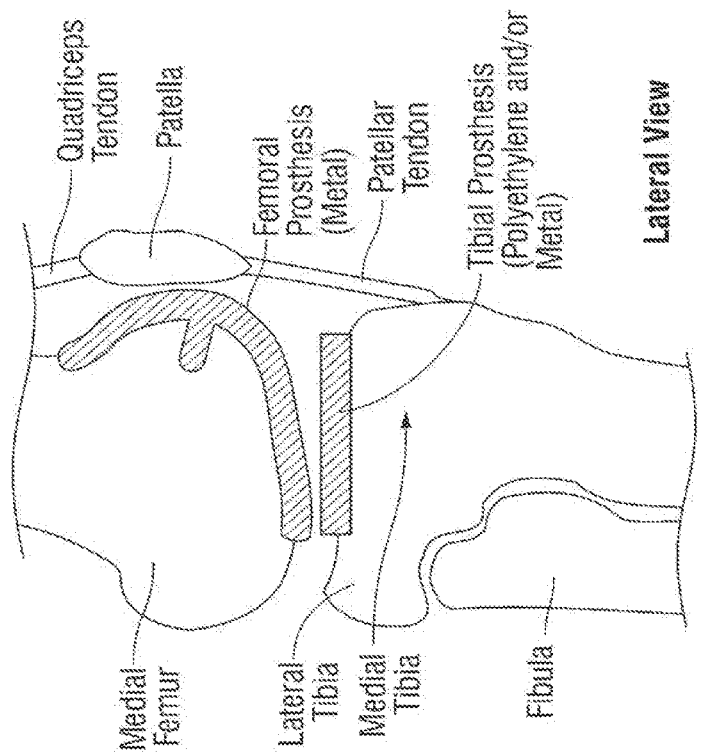
FIG. 98
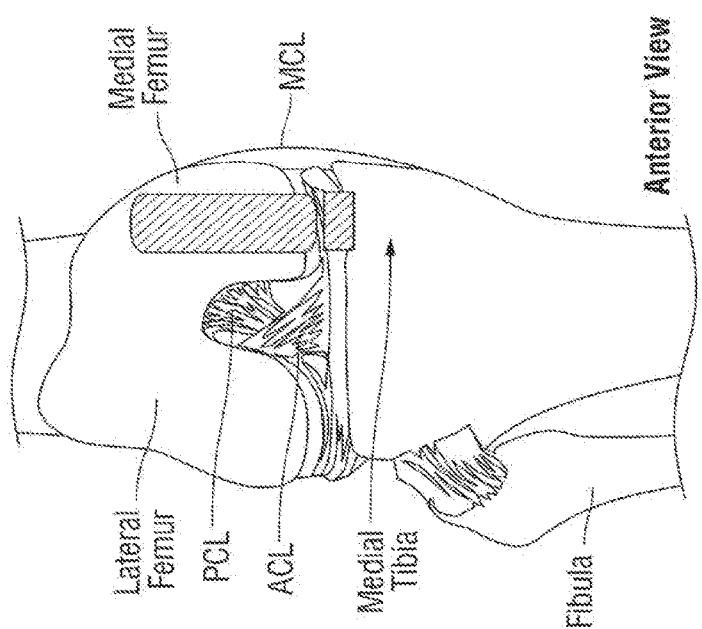
FIG. 97
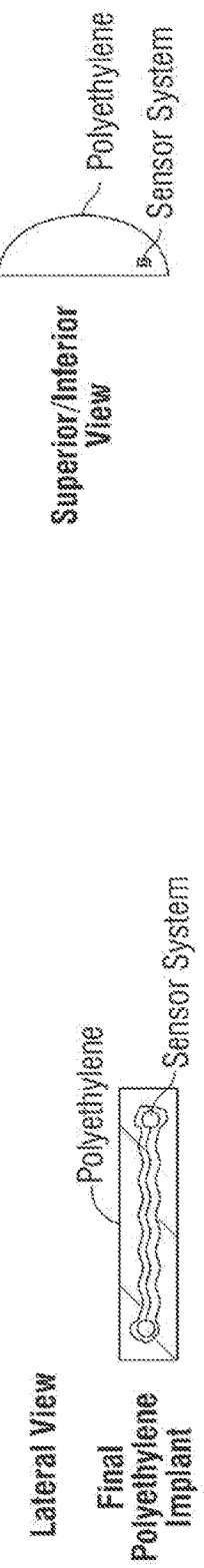
FIG. 100
FIG. 99

METHOD FOR DETECTING BODY PARAMETERS

CROSS-REFERENCE TO RELATED APPLICATIONS

This application is:
This application is a continuation of U.S. patent application Ser. No. 16/550,437, filed Aug. 26, 2019, which is a continuation of U.S. patent application Ser. No. 13/017,040, filed Jan. 30, 2011.
a continuation-in-part of U.S. patent application Ser. No. 11/391,988, filed on Mar. 29, 2006 (which application claims the priority of U.S. Provisional Patent Application No. 60/665,797, filed Mar. 29, 2005, and U.S. Provisional Patent Application Nos. 60/763,761 and 60/763,869, both filed Feb. 1, 2006);
a continuation-in-part of U.S. patent application Ser. No. 13/014,767, filed on Jan. 27, 2011;
a continuation-in-part of U.S. patent application Ser. No. 13/014,773, filed on Jan. 27, 2011;
a continuation-in-part of U.S. patent application Ser. No. 13/014,782, filed on Jan. 27, 2011;
a continuation-in-part of U.S. patent application Ser. No. 13/015,685, filed on Jan. 28, 2011;
a continuation-in-part of U.S. patent application Ser. No. 12/604,072, filed on Oct. 22, 2009 (which application claims the priority of U.S. Provisional Patent Application No. 61/196,914, filed Oct. 22, 2008);
a continuation-in-part of U.S. patent application Ser. No. 12/604,083, filed on Oct. 22, 2009 (which application claims the priority of U.S. Provisional Patent Application No. 61/196,915, filed Oct. 22, 2008);
a continuation-in-part of U.S. patent application Ser. No. 12/604,099, filed on Oct. 22, 2009 (which application claims the priority of U.S. Provisional Patent Application No. 61/196,916, filed Oct. 22, 2008);
a continuation-in-part of U.S. patent application Ser. No. 12/748,099, filed on Mar. 26, 2010 (which application claims the priority of U.S. Provisional Patent Application No. 61/211,023, filed Mar. 26, 2009);
a continuation-in-part of U.S. patent application Ser. No. 12/748,112, filed on Mar. 26, 2010 (which application claims the priority of U.S. Provisional Patent Application No. 61/211,023, filed Mar. 26, 2009);
a continuation-in-part of U.S. patent application Ser. No. 12/748,126, filed on Mar. 26, 2010 (which application claims the priority of U.S. Provisional Patent Application No. 61/211,023, filed Mar. 26, 2009);
a continuation-in-part of U.S. patent application Ser. No. 12/748,136, filed on Mar. 26, 2010 (which application claims the priority of U.S. Provisional Patent Application No. 61/211,023, filed Mar. 26, 2009);
a continuation-in-part of U.S. patent application Ser. No. 12/748,147, filed on Mar. 26, 2010 (which application claims the priority of U.S. Provisional Patent Application No. 61/211,023, filed Mar. 26, 2009),
the entire disclosures of which are hereby incorporated herein by reference in their entireties.

STATEMENT REGARDING FEDERALLY SPONSORED RESEARCH OR DEVELOPMENT n/a

FIELD OF THE INVENTION

The present invention lies in the field of medical devices, in particular, in the field of externally applied and embedded sensor systems for detecting specific parameters of a physiological (e.g., musculoskeletal) system and determining the exact anatomic site of activity, and methods for detecting parameters of anatomical sites.

BACKGROUND OF THE INVENTION

Sensor technology has been disclosed in U.S. Pat. Nos. 6,621,278, 6,856,141, 6,984,993, 7,080,554, 7,266,989, 7,313,491, 7,325,460, 7,520,179, 7,533,571, 7,710,124, and 7,716,988 and assigned to Nexense Ltd. (the "Nexense patents"). The entire disclosures of which are hereby incorporated herein by reference in their entireties.

It would be beneficial to apply existing sensor technology to biometric data sensing applications so that health care personnel can determine characteristics of anatomic sites.

BRIEF SUMMARY OF THE INVENTION

It is accordingly an object of the present invention to provide a sensor system that can detect specific parameters (e.g., of a musculoskeletal system) and determine the exact anatomic site of activity and methods for detecting parameters of anatomical sites that overcome the hereinafore-mentioned disadvantages of the heretofore-known devices and methods of this general type and that provides an externally applied and/or embedded sensor to give healthcare providers real time information regarding their patients. The information can include pathological processes as well as information regarding surgical procedures and implanted devices. The sensors can be activated by internal or external mechanisms, and the information relayed through wireless pathways. The sensor system will allow early intervention or modification of an implant system and can use existing sensors. For example, the sensors disclosed in Nexense patents can be used.

With the foregoing and other objects in view, there is provided, in accordance with the invention, a method for detecting biometric parameters including the steps of performing a surgical procedure on at least one bone, implanting at least one biometric transceiver at the at least one bone, transmitting a first energy wave from the transceiver into a procedure area including at least one of the bone and an area adjacent the bone, quantitatively assessing the behavior of the energy wave with the transceiver, after transmitting the first energy wave: transmitting a second energy wave from the transceiver into the procedure area; and quantitatively assessing the behavior of the second energy wave. At least one of the first and second energy waves are pulsed during transmission in a vibratory manner to stimulate the procedure area in accordance with at least one detected parameter of the procedure area. A current status is determined of the at least one parameter of the procedure area selected from the group consisting of pressure, tension, shear, relative position, bone density, fluid viscosity, temperature, strain, angular deformity, vibration, venous flow, lymphatic flow, load, torque, distance, tilt, shape, elasticity, motion, bearing wear, subsidence, bone integration, change in viscosity, particulate matter, kinematics, stability, and vascular flow with the transceiver based upon a comparison between the assessed behavior of the first and second energy waves.

In accordance with another mode of the invention, there are provided the steps of transmitting data relating to the at least one biometric parameter to an external source and analyzing the data to evaluate a biometric condition of the at least one bone.

In accordance with a further mode of the invention, a set of the transceivers is provided on the at least one bone.

In accordance with an added mode of the invention, based upon the evaluation of the biometric condition of the at least one bone, a currently ongoing interoperative procedure at the procedure area is changed.

In accordance with an additional mode of the invention, based upon the evaluation of the biometric condition of the at least one bone, the anatomic condition relating to the procedure area is chronically monitored.

In accordance with yet another mode of the invention, energy is provided from outside the procedure area to the transceiver to power the transceiver and, thereby, create the energy wave and quantitatively assess the behavior of the energy wave.

In accordance with yet a further mode of the invention, the energy is provided through at least one of an electromagnetic couple, a magnetic couple, a capacitive couple, an inductive couple, a sonic couple, an ultrasonic couple, a fiber optic couple, an optical couple, and an infrared couple.

In accordance with yet an added mode of the invention, a set of the biometric transceivers is provided at the procedure area, an energy wave is transmitted from the transceivers into the procedure area, the behavior of the energy wave is quantitatively assessed with at least one of the transceivers, and, based upon the assessed behavior, a current status of the at least one parameter is determined.

In accordance with yet an additional mode of the invention, a set of the biometric transceivers is provided at the procedure area, energy waves are transmitted from the transceivers into the procedure area, the behaviors of the energy waves are quantitatively assessed with the transceivers, and, based upon the assessed behaviors, a current status of the at least one parameter is determined.

In accordance with again another mode of the invention, the area adjacent the bone is a second bone different from the bone, and an energy wave is transmitted from the transceiver, into the second bone, and back to the transceiver.

In accordance with again a further mode of the invention, the status determining step is carried out by determining a current status of at least two of the group of parameters with the transceiver.

In accordance with a concomitant mode of the invention, the at least one biometric transceiver is embedded at the at least one bone.

Other features that are considered as characteristic for the invention are set forth in the appended claims.

Although the invention is illustrated and described herein as embodied in a sensor system that can detect specific body parameters and determine exact anatomic site of activity and methods for detection, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments the present invention will be apparent from the following detailed description of the preferred embodiments thereof, which description should be considered in conjunction with the accompanying drawings in which:

FIG. 20 is a diagrammatic, fragmentary perspective lateral view of an exemplary embodiment of a post-operative pain inhibitor system for post-operative pain treatment of a skeletal system of a leg according to the invention;

FIG. 21 is a diagrammatic, fragmentary perspective anteroposterior view of the post-operative pain inhibitor system for post-operative pain treatment of a skeletal system of a leg according to the invention;

FIG. 22 is a diagrammatic, fragmentary perspective anteroposterior view of an exemplary embodiment of a post-operative pain inhibitor system for post-operative pain treatment of a skeletal system of a leg according to the invention:

FIG. 23 is a diagrammatic, fragmentary perspective lateral view of the post-operative pain inhibitor system for post-operative pain treatment of a skeletal system of a leg according to the invention:

FIG. 26a is an anteroposterior view of an exemplary embodiment of a prosthetic component having integrated electrical leads to provide a signal to a peripheral nerve fiber to reduce post-operative pain according to the invention;

FIG. 26b is a lateral view of the prosthetic component of FIG. 26a;

FIG. 27 is a diagrammatic, fragmentary perspective anteroposterior view of an exemplary embodiment of components of the post-operative pain inhibitor system integrated into more than one prosthetic components according to the invention;

FIG. 30a is a diagrammatic, fragmentary, side elevational anteroposterior view of an exemplary embodiment of a tibial implant according to the invention:

FIG. 30b is a diagrammatic, fragmentary, side elevational lateral view of the tibial implant of FIG. 30a;

FIG. 35 is a diagrammatic, fragmentary front elevational view of an exemplary embodiment of a plurality of sensors placed on a lower leg according to the invention:

FIG. 36 is a diagrammatic, fragmentary lateral view of the plurality of sensors placed on the lower leg of FIG. 35;

FIG. 46 is a diagrammatic, enlarged, partially cross-sectional view of a handle connected to an implantable sensor body according to the invention:

FIG. 47 is a diagrammatic, enlarged, partially cross-sectional view of the handle of FIG. 46 disconnected from the sensor body:

FIG. 48 is a diagrammatic illustration of an exemplary embodiment of an infra-red visualization system according to the invention;

FIG. 49 is a diagrammatic illustration of an exemplary embodiment of an electromagnetic visualization system according to the invention:

FIG. 50 is a fragmentary, partially hidden, anterior view of a knee joint with an exemplary embodiment of sensors according to the invention;

FIG. 51 is a fragmentary, lateral view of the knee joint with an exemplary embodiment of sensors according to the invention;

FIG. 52 is a diagrammatic, fragmentary side elevational view of a ligament:

FIG. 53 is a diagrammatic fragmentary side elevational view of the ligament of FIG. 52 with a ligament sensor clamp according to the invention in an adjacent position:

FIG. 54 is a diagrammatic, fragmentary side elevational view of the ligament and ligament sensor clamp of FIG. 53 with the ligament sensor partially attached;

FIG. 55 is a diagrammatic, fragmentary side elevational view of the ligament and ligament sensor claim of FIG. 53 with the ligament sensor attached to the ligament;

FIG. 67 is a fragmentary, cross-sectional view of a portion of an ultrasonic cannula system according to the invention;

FIG. 68 is a fragmentary, cross-sectional view of a portion of a single sensor cannula deployment device according to the invention;

FIG. 69 is a fragmentary, cross-sectional view of a portion of a cannula deployment device with multiple sensors;

FIG. 70 is a fragmentary, cross-sectional view of a portion of a multi-sensor cannula deployment device according to the invention;

FIG. 71 is a fragmentary side elevational view of an open knee surgery with exclusion of soft tissue and cartilage and bone cuts with sensors according to the invention deployed;

FIG. 86 is a diagram of an exemplary embodiment of a communication network for measurement and reporting according to the invention;

FIG. 91 is a fragmentary superior elevational view of an exemplary embodiment of a trial plastic insert according to the invention:

FIG. 92 is a fragmentary side elevational view of the trial plastic insert of FIG. 91;

FIG. 93 is a diagram of an exemplary embodiment of a wireless communications system according to the invention;

FIG. 97 is a fragmentary front elevational view of an exemplary embodiment of a medial knee implant according to the invention in flexion:

FIG. 98 is a fragmentary side elevational view of the medial knee implant of FIG. 97;

FIG. 99 is an elevational view of an exemplary embodiment of a tibial insert with the embedded sensors; and FIG. 100 is an elevational view of the tibial insert of FIG. 99.

DETAILED DESCRIPTION OF THE PREFERRED EMBODIMENTS

Figure 1:
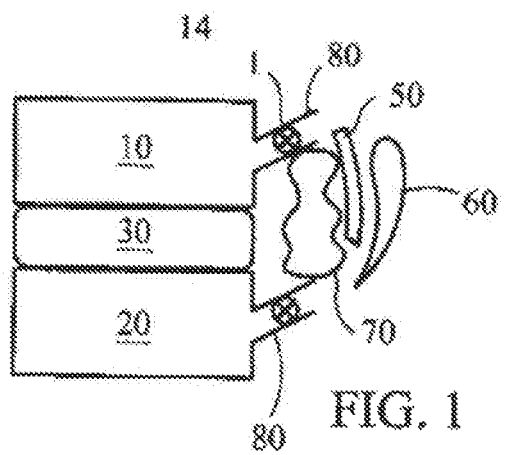
FIG. 1 is a diagrammatic, fragmentary, lateral view of a portion of a spine with a non-instrumented fusion of the spine and sensors according to the invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. It is noted that similar reference numerals and letters refer to similar items in the following figures, and thus once an item is defined in one figure, it may not be discussed or further defined in the following figures. The figures of the drawings are not drawn to scale.

An externally applied sensor system according to the present invention can be used to evaluate skin integrity and pathological pressure that can lead to skin ischemia and ultimately skin breakdown (Decubiti). It is important to detect certain parameters that can lead to skin breakdown. Elements such as pressure, time, shear, and vascular flow, for example, are important to detect. The specific anatomic location is needed.

The sensor system of the present invention can be embedded in a thin, adhesive, conforming material that is applied to specific areas of concern. Exemplary areas include the heel, hips, sacrum, and other areas of risk. These sensors map out the anatomic area. If threshold parameters are exceeded, the sensors inform a telemetric receiver that, in turn, activates an alarm to the nurse or other health care professional. In one exemplary application, the information is used to control the bed that the patient is lying upon to relieve the area of concern. In particular, adjustment of aircells in the mattress can be made to unload the affected area of concern.

The external sensor system can be configured in various ways. In an exemplary embodiment, a sensor is disposed within a thin, conformable adhesive that is applied directly to the patient's body and is powered by a thin lithium battery. This sensor(s) documents specific parameters such as pressure, time, shear, and vascular flow. The sensor telemetrically informs a receiving unit and sets an alarm if certain pre-programmed parameters are exceeded. In one embodiment where a visual aid is provided (such as a computer screen displaying the patient's body outline, the exact area of concern can be highlighted and, thereby, visualized by the health care professional.

Embedded sensors are needed to detect certain internal parameters that are not directly visible to the human eye. These sensors will be used in specific locations to detect specific parameters.

One way of embedding a sensor is through an open surgical procedure. During such a surgical procedure, the sensor is embedded by the surgeon directly into bone or soft tissue or is attached directly to a secured implant (e.g., a prosthesis (hip, knee)). The sensor system is used during the surgical procedure to inform the surgeon on the position and/or function of the implant and of soft tissue balance and/or alignment. The sensor is directly embedded with a penetrating instrument that releases the sensor at a predetermined depth. The sensor is attached to the secured implant with a specific locking system or adhesive. The sensor is activated prior to closure for validating the sensor.

Another way of embedding a sensor is through a percutaneous procedure. The ability to implant sensors in specific locations is important to evaluate internal systems. Sensors of varying diameters can be implanted into bone, soft tissue, and/or implants. The procedure is applied under visualization supplied, for example, by fluoroscopy, ultrasound imaging, and CAT scanning. Such a procedure can be performed under local or regional anesthesia. The parameters evaluated are as set forth herein. The percutaneous system includes a thin instrument with a sharp trocar that penetrates the necessary tissue plains and a deployment arm releases the sensor(s) at a predetermined depth(s). The instrument could also house the necessary navigation system to determine the specific anatomic location required.

The parameters to be evaluated and time factors determine the energy source required for the embedded sensor. Short time frames (up to 5 years) allow the use of a battery. Longer duration needs suggest use of external activation or powering systems or the use of the patient's kinetic energy to supply energy to the sensor system. These activation systems can be presently utilized. The sensors would also be activated at predetermined times to monitor implant cycles, abnormal motion and implant wear thresholds.

Information is received telemetrically. In one exemplary embodiment, the sensors are preprogrammed to "activate" and send required information if a specific threshold is exceeded. The sensors could also be activated and used to relay information to an external receiver. Further applications allow readjustment of a "smart implant" to release specific medications, biologics, or other substances, or to readjust alignment or modularity of the implant.

The sensor system is initially activated and read in a doctor's office and further activation can occur in the patient's house, with the patient having ability to send the information through Internet applications, for example, to the physician.

Software will be programmed to receive the information, process it, and, then, relay it to the healthcare provider.

The sensor system of the present invention has many different applications. For example, it can be used to treat osteoporosis. Osteoporosis is a pathological condition of bone that is characterized by decreased bone mass and increased risk of fracture. It is well accepted that bone-mineral content and bone-mineral density are associated with bone strength.

Bone density is an extremely important parameter of the musculoskeletal system to evaluate. Bone density measurements are used to quantify a person's bone strength and ultimately predict the increased risks associated with osteoporosis. Bone loss leads to fractures, spinal compression, and implant loosening. Presently, physicians use external methods such as specialized X-rays.

The unit of measurement for bone densitometry is bone-mineral content, expressed in grams. Bone density changes are important in the evaluation of osteoporosis, bone healing, and implant loosening from stress shielding. Another important evaluation is in regard to osteolysis. Osteolysis can destroy bone in a silent manner. It is a pathological reaction of the host to bearing wear, such as polyethylene. The polyethylene particles activate an immune granulomatous response that initially affects the bone surrounding the implant. Bone density changes will occur prior to cystic changes that lead to severe bone loss and implant failure.

There are multiple external systems that can evaluate bone density. The problems with such systems encountered are related to the various systems themselves, but also to the socio-economic constraints of getting the patient into the office to evaluate a painless disease; coupled with the constricted payment allocations that cause long intervals between evaluations.

Sensors used according to the present invention allow evaluation of changes in bone density, enabling health care providers to know real time internal data. Application of the sensors can assess osteoporosis and its progression and/or response to treatment. By evaluating changes in bone density, the sensors provide early information regarding fracture healing and early changes of osteolysis (bone changes relating to polyethylene wear in implants).

Although the instrumentation various with different modalities, all record the attenuation of a beam of energy as it passes through bone and soft tissue. Comparisons of results are necessarily limited to bones of equal shape, which assumes a constant relationship between the thickness of the bone and the area that is scanned. Moreover, the measurements are strictly skeletal-site-specific; thus, individuals can be compared only when identical locations in the skeleton are studied.

Dual-energy x-ray absorptiometry can be used to detect small changes in bone-mineral content at multiple anatomical sites. A major disadvantage of the technique is that it does not enable the examiner to differentiate between cortical and trabecular bone. Quantitative ultrasound, in contrast to other bone-densitometry methods that measure only bone-mineral content, can measure additional properties of bone such as mechanical integrity. Propagation of the ultrasound wave through bone is affected by bone mass, bone architecture, and the directionality of loading. Quantitative ultrasound measurements as measures for assessing the strength and stiffness of bone are based on the processing of the received ultrasound signals. The speed of sound and the ultrasound wave propagates through the bone and the soft tissue. Prosthetic loosening or subsidence, and fracture of the femur/tibia/acetabulum or the prosthesis, are associated with bone loss. Consequently, an accurate assessment of progressive quantifiable changes in periprosthetic bone-mineral content may help the treating surgeon to determine when to intervene in order to preserve bone stock for revision arthroplasty. This information helps in the development of implants for osteoporotic bone, and aids in the evaluation of medical treatment of osteoporosis and the effects of different implant coatings.

The sensor system of the present invention can be used to evaluate function of internal implants. Present knowledge of actual implant function is poor. Physicians continue to use external methods, including X-rays, bone scans, and patient evaluation. However, they are typically left only with open surgical exploration for actual investigation of function. Using sensors according to the present invention permits detection of an implant's early malfunction and impending catastrophic failure. As such, early intervention is made possible. This, in turn, decreases a patient's morbidity, decreases future medical care cost, and increases the patient's quality of life.

The sensors can be attached directly to implant surfaces (pre-operatively and/or intra-operatively) and/or directly to the implant-bone interface. Sensors can be implanted into the bone and soft tissue as well. In such an application, the physician could evaluate important parameters of the implant-host system. Exemplary parameters that could be measured include: implant stability, implant motion, implant wear, implant cycle times, implant identification, implant pressure/load, implant integration, joint fluid analysis, articulating surfaces information, ligament function, and many more.

Application of sensors according to the invention allows one to determine if the implant is unstable and/or if excessive motion or subsidence occurs. In an exemplary application, the sensor can be configured to release an orthobiologic from an activated implanted module to increase integration. Alternatively and/or additionally, the implant system with the sensors can be used to adjust the angle/offset/soft tissue tension to stabilize the implant if needed.

Sensors can be used to detect whether or not implant bearings are wearing out. Detectable bearing parameters include early wear, increased friction, etc. An early alarm warning from the sensor could enable early bearing exchange prior to catastrophic failure.

A joint implant sensor can detect an increase in heat, acid, or other physical property. Such knowledge would provide the physician with an early infection warning. In an exemplary infection treatment application, the sensor can activate an embedded module that releases an antibiotic.

The sensors can be used to analyze knee surgeries. Such sensors can be placed posteriorly in the knee to evaluate popliteal artery flow, pressure, and/or rhythm. A femoral implant sensor is placed anteriorly to monitor femoral artery/venous flow, pressure, and/or rhythm. An internal vascular monitor can be part of the implant and include devices to release antihypertensive or anti-arrhythmic modules to modify vascular changes when needed.

In one exemplary embodiment, the internal orthopedic implant is, itself, the sensor of the present invention. In a trauma situation, for example, the reduction screw can be both the implant and the sensor. Such a screw can detect abnormal motion at the fracture site and confirm increase in density (i.e., healing). Such an application allows percutaneous implantation of bone morphogenic protein (BMP) to aid in healing or a percutaneous adjustment of the hardware.

The sensor of the present invention can be used in spinal implants. A sensor placed in the spine/vertebrae can detect abnormal motion at a fusion site. The sensor evaluates spinal implant integration at the adjacent vertebral segments and/or detects adjacent vertebral segment instability. Implanted sensors can activate a transitioning stabilizing system or implant and determine the areas of excessive motion to enable percutaneous stability from hardware or an orthobiologic.

Figure 2:
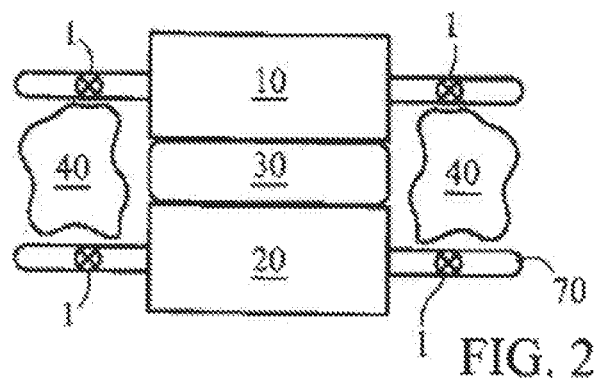
FIG. 2 is a diagrammatic, fragmentary, anterior-posterior view of the spine portion of FIG. 1.

Referring now to the figures of the drawings in detail and first, particularly to FIG. 1 thereof, there is shown a fragmentary lateral view of a fusion of a portion of the spine. An upper vertebra 10 is separated from a lower vertebra 20 by a disc 30. A bone graft 40 is covered first by an inferior facet 50 and second by a superior facet 60. FIG. 2 is an anterior-posterior view of the spine portion of FIG. 1 in which the bone graft 40 is shown on either side of the disc 30 with opposing transverse processes 70. Sensors 1 according to the present invention can detect and transmit information regarding motion and loads of the vertebra 10, 20 and are implanted in various spinal elements. The elements can include the spinal pedicles 80, transverse processes 70, facets, etc.

FIGS. 1 and 2 depict how sensors 1 of the present invention can be used in non-instrumented fusions of the spine. The sensors 1 are activated at variable times in the post-operative period. Abnormal or excessive motion around the fusion "mass" helps detect a non-union, for example.

Figure 3:
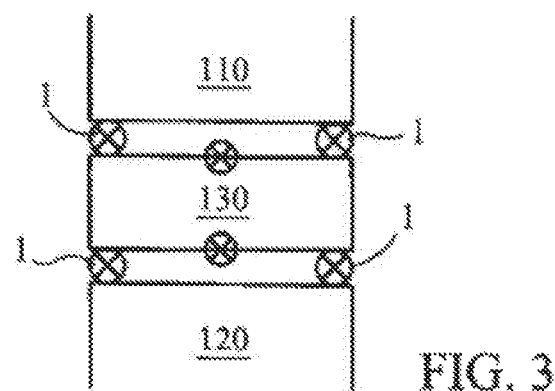
FIG. 3 is a diagrammatic, fragmentary, lateral view of a portion of a spine with an intervertebral cage and sensors according to the invention.

FIG. 3 depicts how sensors 1 of the present invention can be use in instrumented spinal fusions. More particularly, the sensors 1 are incorporated into the "cage" instrumentation 130 in between an inferior vertebral plate 110 and a superior vertebral plate 120. Such a sensor 1 detects motion and load and is activated to transmit information in the post-operative period to help determine if the fusion mass was solid.

Figure 4:
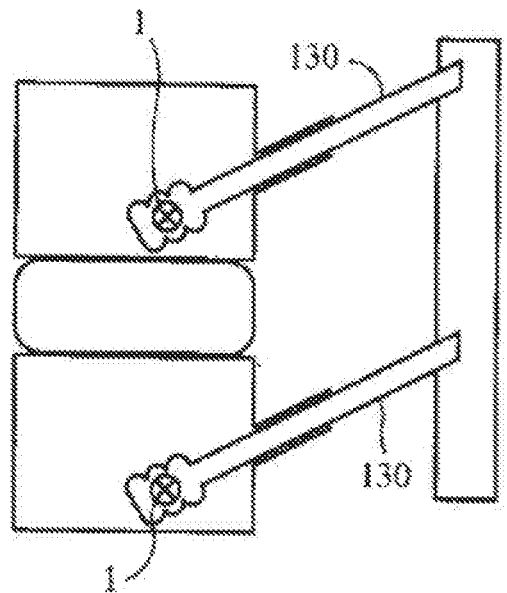
FIG. 4 is a diagrammatic, fragmentary, anterior-posterior view of the spine portion of FIG. 1 with sensors according to the invention in pedical screws

FIG. 4 depicts how sensors 1 of the present invention can be used in pedicle screws 130. More particularly, sensors 1 are incorporated into the pedicle screw 130 to help detect any abnormal motion between vertebrae in the fusion mass.

Figure 5:
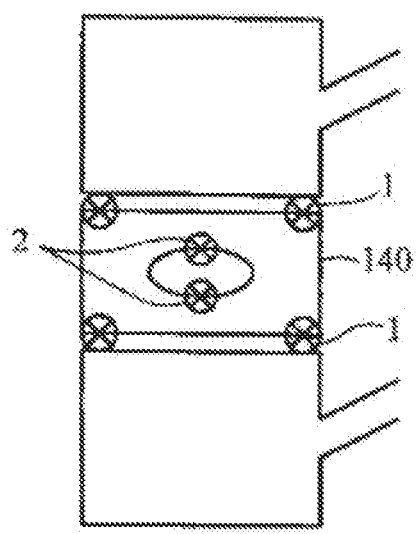
FIG. 5 is a diagrammatic, fragmentary, lateral view of a portion of a spine with an intervertebral disc implant and sensors according to the invention.

FIG. 5 depicts how sensors 1 of the present invention can be use in invertebral disc implants (replacements). More particularly, an artificial disc replacement 140 has sensors 1 placed on the metal-bone interface, for example. These sensors 1 detect loads as well as motion to help, intraoperatively, in the placement of the disc 140 and, postoperatively, determine stable integration of the disc-bone interface. Internal sensors to detect "normal" motion between the articulating disc and external interfaces help confirm, post-operatively, that the disc replacement is optimally functioning with variable loads and spinal motion.

Figure 6:
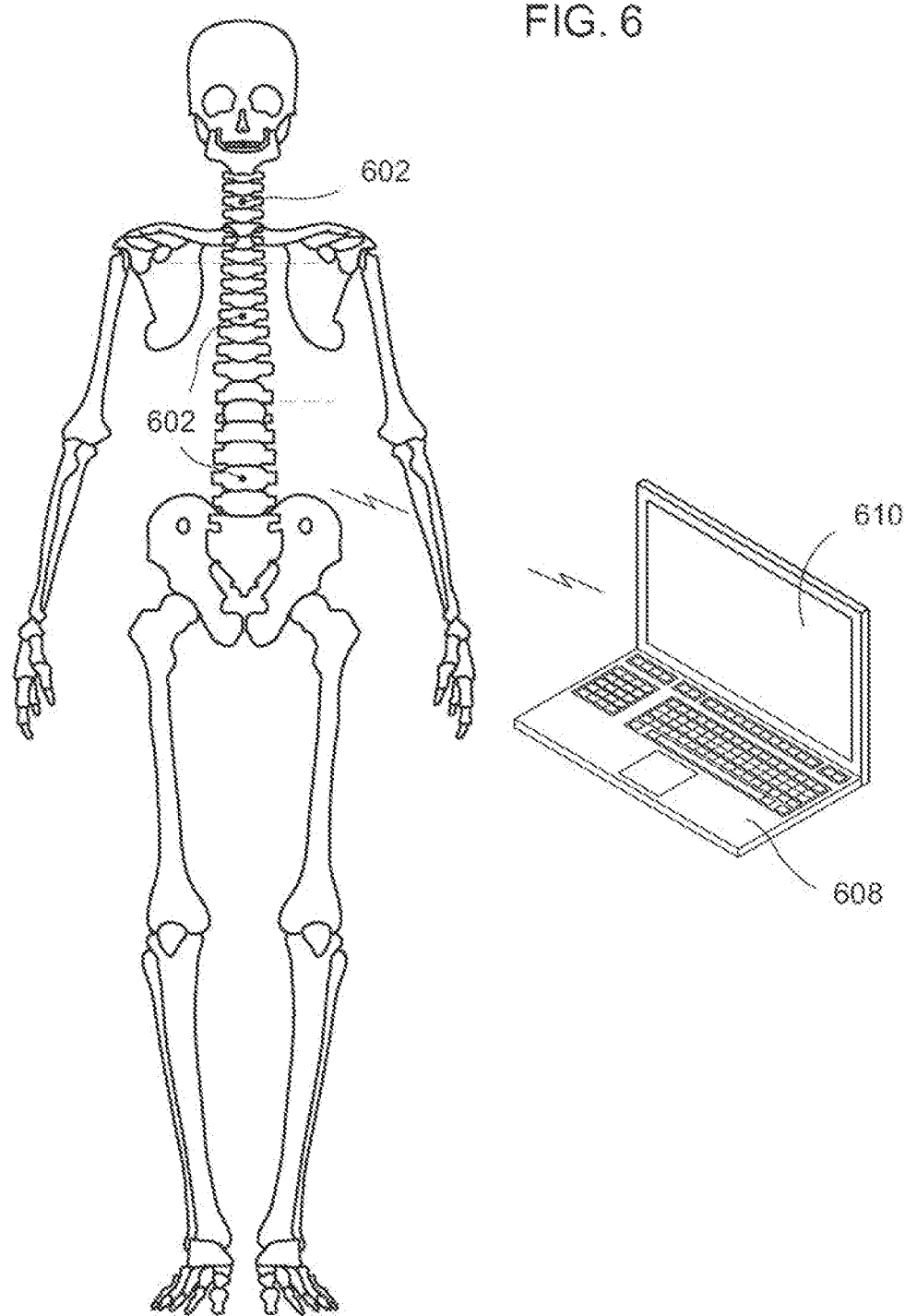
FIG. 6 is an illustration of an exemplary embodiment of spinal column and sensor arrays according to the invention.

FIG. 6 is an illustration of a spinal column and sensors in accordance with an exemplary embodiment of the invention. The human spine comprises cervical, thoracic, and lumbar regions respectively corresponding to C1-C7, T1-T12, and L1-L5. A healthy spinal column has a mechanical axis in an upright position that distributes loading that minimizes stress on each vertebrae. An example of a spinal deformity that can require correction is scoliosis, which is a curving of the spine. In general, spinal deformities can often be corrected using devices that place the spine or help the spine be in the most ideal mechanical situation. In any spinal correction, the position of the spine and each element of the spine needs to be in alignment and dimensionally correct (in all three dimensions). Thus, in spine surgery, alignment and stability are critical and often difficult to achieve. It is important for the surgeon to obtain data as he/she corrects the spinal deformity in a minimum of three planes. It is also helpful to identify the increasing and decreasing loads across spinal segments as this is performed.

A system to accomplish this includes more than one sensor array 602 according to the invention. In at least one exemplary embodiment, at least one sensor is placed on or in the cervical, thoracic, and lumbar regions of the spinal column, in a non-limiting example, sensor arrays 602 include accelerometers or other position sensing devices such as fiber-optics and RF/EM/US sensors that detect position in all three dimensions. In particular, the placement of sensor arrays 602 on vertebrae is done in a manner where the three-dimensional position data reflects the position of the vertebrae of the spinal column. Sensor arrays 602 are in communication with a computational unit 608 able to provide three dimensional positioning information of the vertebrae and the regions of the spine on screen 610. It is noted that sensors 602 provides positional information in relation to each sensor and can provide data corresponding to the rotation of a vertebrae within a region of the spine or from region to region. As shown, screen 610 can display (in varying views) that the vertebrae of the spinal column are aligned along a preferred mechanical axis or an axis corresponding to each spinal region in three dimensions and that each vertebrae are not rotated in the mechanical axis.

Figure 7:
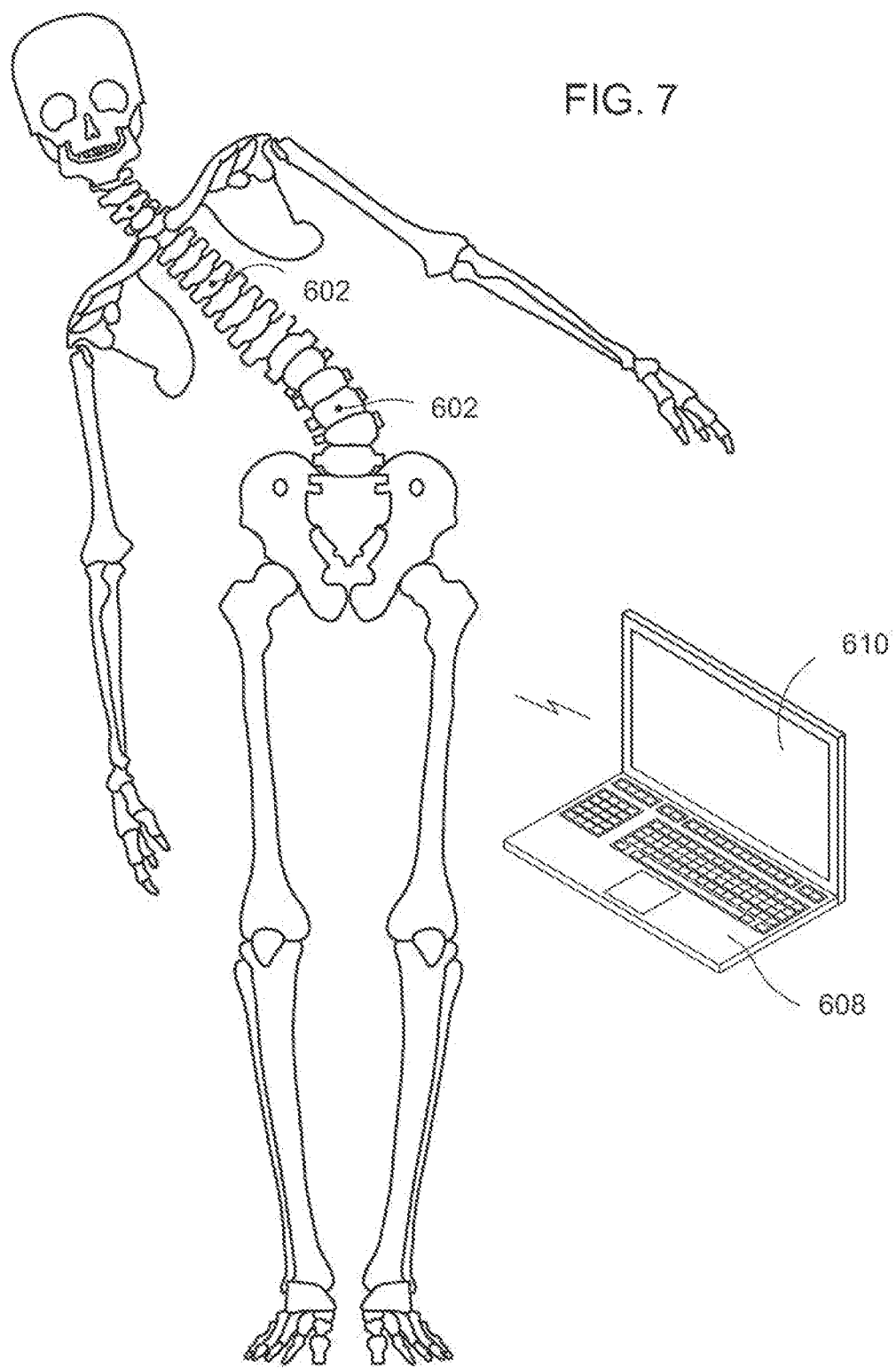
FIG. 7 is an illustration of an exemplary embodiment of spinal column and sensor arrays providing positional information according to the invention.

FIG. 7 is an illustration of a spinal column and sensors providing positional information in accordance with an exemplary embodiment of the invention. As illustrated, sensor arrays 602 are placed in predetermined locations of the spinal column. Sensor arrays 602 in communication with the computational unit 608 indicate, on the screen 610, curvature of the spine in more than one spinal region. The surgeon can view the definition of the pre-surgical alignment in all three planes on the screen 610. In at least one exemplary embodiment, the surgeon is able to rotate the image on the screen to see spine alignment from different perspectives.

The surgeon uses the system during surgery to further define the achievement of the overall spinal correction angle, and define that the cervical sacral angles are centralized. The surgeon adds bracing, adjusts tensioning, or utilizes other techniques known to one skilled in the art to maintain the spine in position. Adjusting one area of the spine may disrupt or change positions in other areas of the spinal column. The system provides information to these changes and allows the surgeon to compensate therefor while the surgery takes place.

Figure 8:
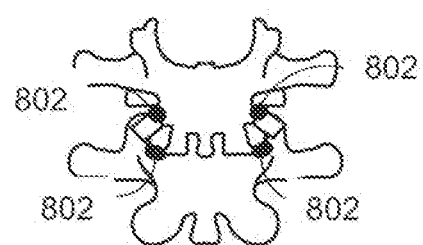
FIG. 8 is an illustration of an exemplary embodiment of vertebrae having sensor arrays according to the invention.

FIG. 8 is an illustration of vertebrae having one or more sensor arrays 802 in accordance with an exemplary embodiment of the invention. The illustration shows sensors 802 monitoring adjacent vertebrae. Sensor arrays 802 are placed in or on the vertebrae such that the force or loading between the two vertebrae can be measured. In at least one exemplary embodiment, the loading can be measured circumferentially to determine if unequal forces are applied to different areas of the vertebrae. Position measurements using sensors 802 can show whether adjacent major surfaces of the vertebrae are parallel to one another and perpendicular to the mechanical axis. Similarly, position data from sensors 802 can indicate if the vertebrae are rotated from an ideal alignment.

Although load is being measured in the example, sensors 802 can measure one or more of at least the following characteristics: load; weight; strain; pressure; wear; position; acceleration; temperature; vibration; density; and distance, to name a few. Thus, substantial benefit can be provided by the system that combines position, alignment, and relational positioning with measurement of one or more parameters in real time to aid in correct installation of an orthopedic device. The system also allows sensing of changes in vascular flow and neural element function (an example of which includes central and peripheral neuromodulation systems or sensors) that would aid in detecting changes at the operative site.

Figure 9:
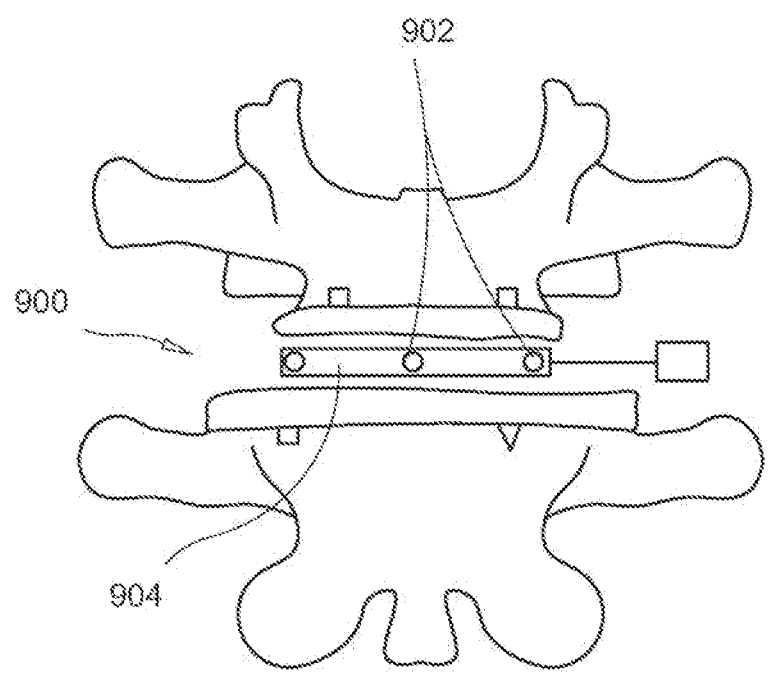
FIG. 9 is an illustration of an exemplary embodiment of a spinal implant and cage according to the invention.

FIG. 9 is an illustration of a spinal implant 900 and cage in accordance with an exemplary embodiment of the invention. In at least one exemplary embodiment, sensor arrays 902 can be used to define appropriate balance of the spinal implant 900 during surgery such as a disc implant or fusion cage. In a non-limiting example, sensor arrays 902 are placed in a trial insert 904 for measuring position and load. The load sensors can define the increased or decreased loads seen above an instrumented spinal segment. This allows motion preserving implants to be utilized without severely affecting the mechanics of adjacent joint segments. These sensors can be disposed of after surgery or left in to define post operative angles and loads.

Figure 10:
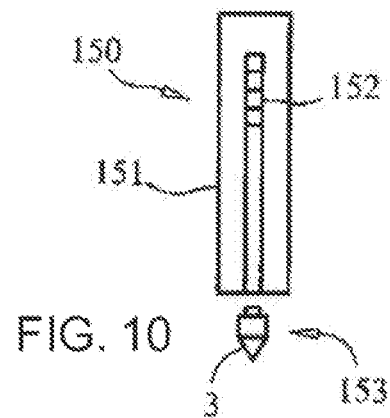
FIG. 10 is a diagrammatic, fragmentary, enlarged cross-sectional view of a sensor inserting instrument according to the invention.
Figure 11:
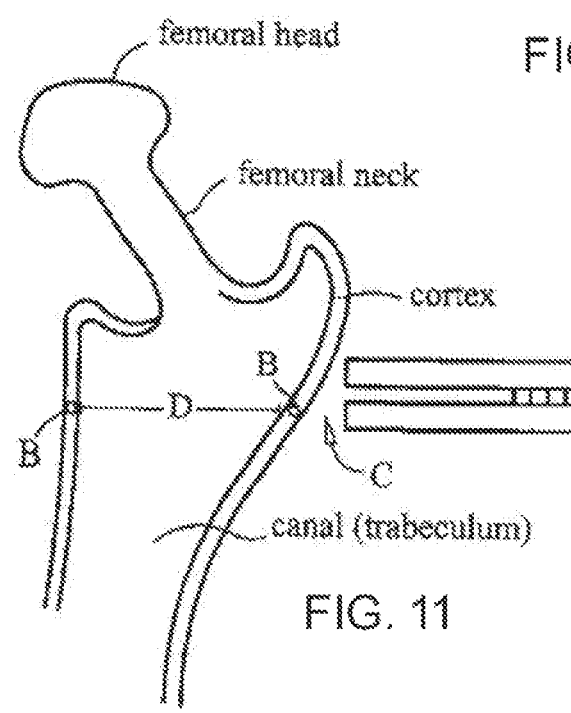
FIG. 11 is a diagrammatic, fragmentary cross-sectional view of an upper femur with sensors according to the invention implanted with the instrument of FIG. 10.

FIG. 10 depicts an example of a sensor deploying instrument 150 having a handle 151 and a plunger 152 according to the invention. The handle 151 and plunger 152 allow the insertion of the sensor 3 that is part of a trocar 153. The trocar 153 can penetrate the cortex and the sensor 3 can be deployed. FIG. 11 depicts the insertion of the sensor 3 in the femur and FIG. 70 depicts the insertion of the sensor 3 in a vertebra. The sensor 3 can, then, be decoupled with a coupling mechanism 154, for example, by an unscrewing or a derotating process. These body areas are used as examples because they are the most commonly affected area with regard to osteoporosis and trauma relating to osteoporosis. The sensor 3 can vary in size from several millimeters to over a centimeter. The sensor 3 can be implanted percutaneously or in an open surgical manner.

The sensor 3 can be part of hardware used in the hip and/or the spine. The sensor 3 can be placed at various depths to allow evaluation of the cortex as well as the travecular bone. With two deployed sensors 3, the distance between the sensors 3 can be determined at the area of concern and the power field that can be generated. The energy fields can be standard energy sources such as ultrasound, radiofrequency, and/or electromagnetic fields. The deflection of the energy wave over time, for example, will allow the detection of changes in the desired parameter that is being evaluated.

Figure 12:
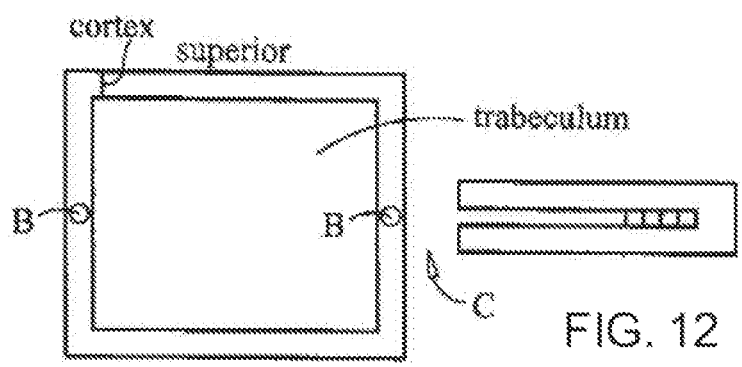
FIG. 12 is a diagrammatic, fragmentary cross-sectional view of a vertebra with sensors according to the invention implanted with the instrument of FIG. 10.

An exemplary external monitoring sensor system according to FIGS. 10 to 12 enables on-contact nightly reads on bone mineral content and density. The sensor system can also enables a transfer of energy waves in a vibratory pattern that can mimic load on the bone and lead to improved bone mineral content and density. The sensors can also send energy waves through or across an implant to, thus, aid in healing of a fracture.

Figure 13:
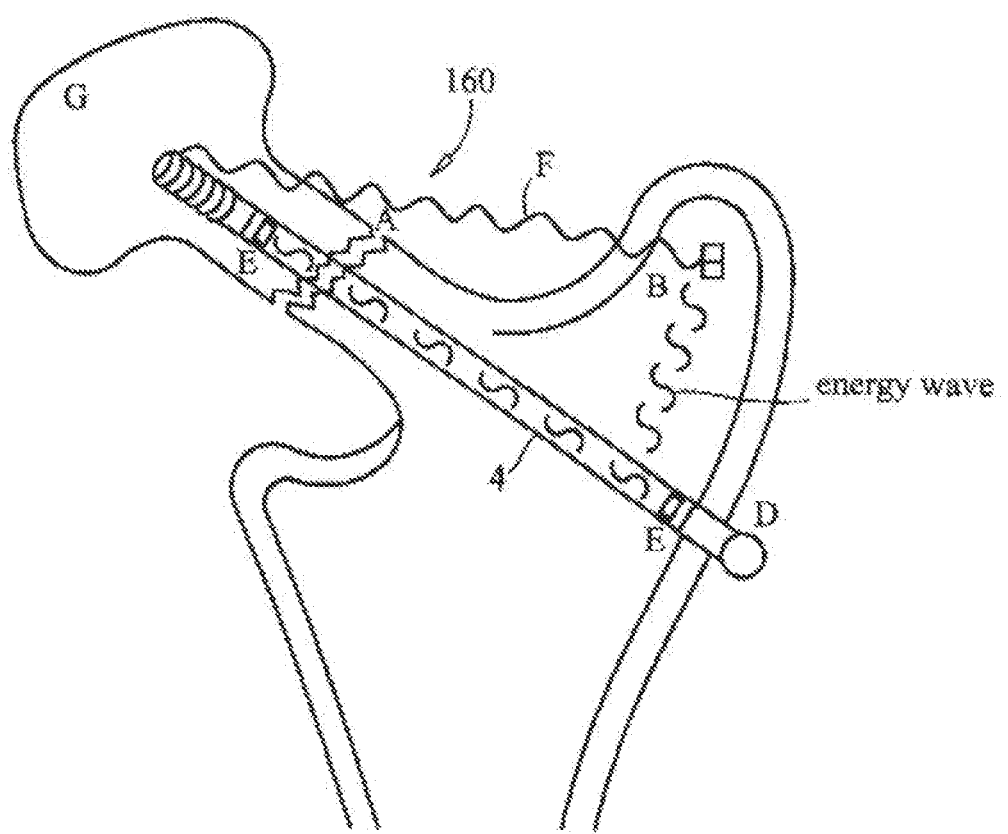
FIG. 13 is a diagrammatic, fragmentary cross-sectional view of a femur with sensors in a screw according to the invention.

Fracturing of a hip and a spinal vertebra is common with respect to osteoporosis and trauma. FIG. 13 depicts the use of a screw 4 as the internal sensor. The fracture 160 is spanned by a compression screw 4 and the sensors 4 are embedded in the screw 4. The sensors 4 in the screw 4 can send energy across the fracture site to obtain a baseline density reading and monitor the change in density over time to confirm healing. The sensors 4 can also be activated externally to send energy waves to the fracture itself to aid in healing. The sensors 4 can also detect the change in motion at the fracture site as well as the motion between the screw and bone. Such information aids in monitoring healing and gives the healthcare provider an ability to adjust weight bearing as indicated. Once the fracture is healed, the sensors 4 shown in FIGS. 14 and 15 within the greater trochanter can now be activated to send energy waves to the other two sensors 4. This will enable continued evaluation of bone density. The sensors 4 can be activated with a sensor bed system when the patient is asleep, for example. The energy source and receiver can be attached to the bed undersurface, for example. The received information can be evaluated every night if needed and sent by standard telephonic measures to the doctor. The activation of the sensors at night will enable specific interval readings during treatment of osteoporosis by various medications.

External and internal energy waves sent with sensors according to the invention can be used during the treatment of fractures and spinal fusions.

The use of ultrasound, pulsed electromagnetic fields, combined magnetic fields, capacitive coupling, and direct electrical current have been studied in their affects on the up regulation of growth factors. Pulsed Ultrasound has shown to activate "integrins." which are receptors on cell surfaces that, when activated, produce an intracellular cascade. Proteins involved in inflammation, angiogenesis, and bone healing are expressed. These proteins include bone morphogenic protein (BMP)-7, alkaline phosphatase, vascular endothelial growth factor and insulin growth factor (IGF)-1. The use of pulsed electromagnetic fields has shown increased bone healing times in animals. Various waveforms affect the bone in different ways.

Figure 14:
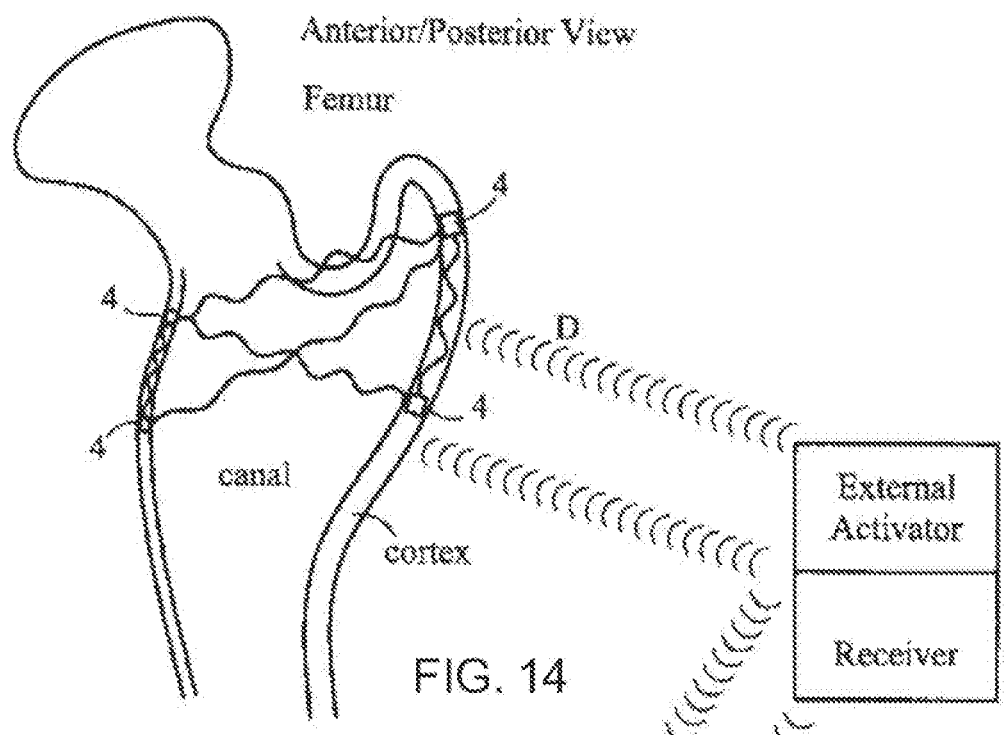
FIG. 14 is a diagrammatic, fragmentary cross-sectional view of a femur with implanted sensors according to the invention.
Figure 15:
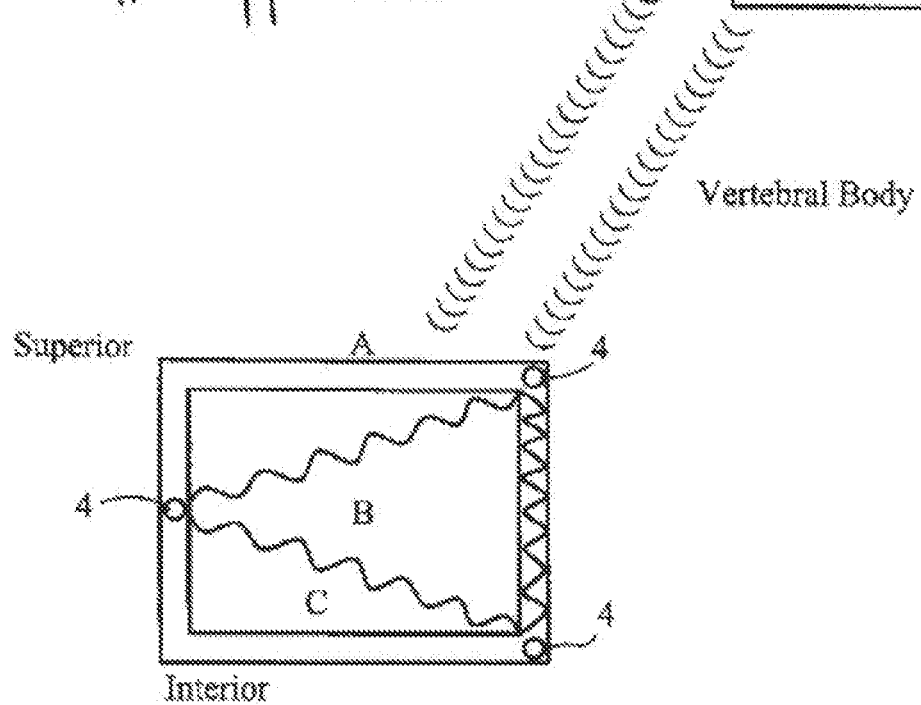
FIG. 15 is a diagrammatic, fragmentary cross-sectional view of a vertebra with sensors according to the invention.

A sensor system using quantitative ultrasound can be used to evaluate calcaneal bone density externally. The system according to the invention is attached to the patients' bed and, by using external ultrasound wave forms as shown in FIGS. 14 and 15, the bone density can be evaluated. The use of energy fields have been shown to stimulate the bone healing process. Stimulation can be effected with external measures, but use of internal sensor systems can change the waveforms and generate a vibratory signal that can effectively "load" the bone. This affect is known, by several orthopedic laws, to strengthen the bone cortex and effectively be use in the treatment of fractures and osteoporosis and is depicted in FIG. 14. The sensors in FIG. 14 are in the cortex or canal. The energy waveforms are sent to each other. They can be activated and received by an external system or be part of the sensor itself. Similarly. FIG. 15 depicts a vertebral segment in which sensors 4 send energy wave forms to each other and to an external receiver. Such a system/treatment can be used to treat fractures and osteoporosis.

In general, the successful implantation of a device in an organism and, more specifically, in a joint or spine depends on multiple factors. As disclosed above, the sensor system can be active for addressing post-operative complications. Discussed hereinbelow are sensor systems for addressing post orthopedic surgery issues with infection and pain and factor taken into account when addressing these issues. A first factor is the surgeon's desire to implant the device to obtain adequate alignment of the extremity or spine. A second factor is proper seating of the implant for stability. A third factor is that orthopedic implants typically comprise more than one component that are aligned in relation to one another. A fourth factor is balance of loading over a range motion. A fifth factor, and a more general factor that relates to all implanted devices, is to minimize infections that can occur post-operatively.

In a first exemplary embodiment of the invention, a system includes an implantable device and a biological sensor coupled to the implanted device. The biological sensor is exposed to the interior of the organism to detect a presence of bacteria and other infecting organisms in proximity to the implantable device post-operatively, for example, after the device is implanted. The system can identify potential medical problems early after surgical implantation of the implantable device and take appropriate measures upon identification of the problem. Benefits of this early diagnosis may reduce post operative re-work with substantial benefits in lowering invasive post-operative procedures, decreasing cost, freeing up operating rooms, and minimizing patient stress.

In a second exemplary embodiment, a system includes an implantable device having a major surface interior to an organism, a first and second electrode (a portion of the interior of the organism being between the first and second electrodes), and a pulsing circuit operatively coupled to the first and second electrode. Each pulse from the pulsing circuit generates an electric field between the first and second electrodes. The electric field electroporates one or more cells of bacteria or an infecting organism in proximity to the generated electric field. The system can control a level and a delivery of a pharmaceutical agent during the electroporation.

In a third exemplary embodiment, a system includes an orthopedic joint implant where a portion of the major surface has a plurality of nanostructures coupled thereto, a biosensor to detect a presence of bacteria or infecting organisms, and a control circuit operatively coupled to the at least one biosensor and the nanostructures to enable a release of the agents contained in the nanostructures. The nanostructures include agents, hydrogels, antibiotics, or cytoxins to reduce infection by bacteria or an infecting organism and prevent bacterial growth in a joint region.

Several implant devices were briefly described earlier, each of which can be configured in accordance with the embodiments herein above. More specifically, orthopedic devices are shown because they typically comprise multiple components that have multiple surfaces internal to a patient. It is noted that orthopedic devices are used herein for illustrative purposes. Various embodiments herein apply to devices implanted internal to an organism. Other examples of implantable devices are monitoring devices, drug delivery devices, pacemakers, defibrillators, to name but a few. A common factor in implanted devices is that post-operative infections can occur and that the device itself can enable the bacteria or infecting organism to thrive.

Figure 16:
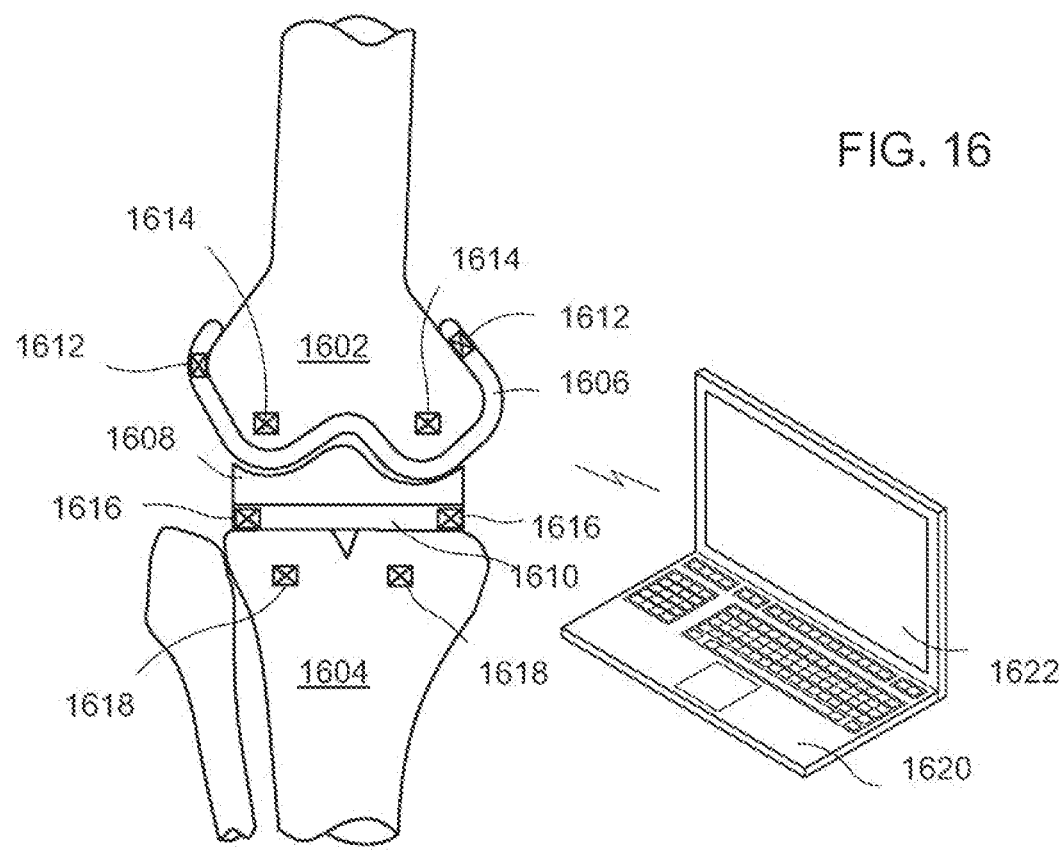
FIG. 16 is a diagrammatic, fragmentary perspective view of an exemplary embodiment of a system for preventing infection on an implanted device according to the invention.

FIG. 16 is an illustration of a system for preventing infection on an implanted device in accordance with an exemplary embodiment of the invention. The implantable device can be used in hip, knee, or spine prosthetics or other orthopedic joints as previously described and shown. A platform to monitor and react to an early or late infection is described hereinbelow. In particular, the platform can detect infections in an early stage when, if detected, can be treated effectively to eliminate the problem. Detection further eliminates an issue where the patient with an implant is often unaware of an infection and does not seek help until the bacteria or infecting organism is firmly established. The inventive system also addresses a problem associated with the implant itself. The implanted device in conjunction with the local biology can provide areas that can harbor, provide sustenance, and fuel growth of the infection.

In at least one exemplary embodiment, system includes one or more sensors that will identify an early infection before it becomes chronic, seeds the device, and prevents the penetration of antibiotics. Most device implants are made of metal or plastics that can be coated by the bacteria allowing them to multiply. In a non-limiting example, a knee implant is used to illustrate the system. The system can be applied to other implanted devices or systems.

The knee implant comprises a femoral implant 1606, an insert 1608, and a tibial implant 1610. Femoral implant 1606 is coupled to a distal end of femur 1602. Similarly, tibial implant 1610 is coupled to a proximal end of tibia 1604. The insert 1608 is coupled between femoral implant 1606 and tibial implant 1610. Insert 1608 provides a bearing surface on which the condyles of femoral implant 1606 contact, allowing rotation of the lower leg. In general, at least one biological sensor is coupled to the implanted device such as a knee implant. In a typical example of the invention, more than one biological sensor is used to detect bacteria or an infecting organism in a region in and around the implanted device. It is noted that infection has the highest probability of occurring within a relatively short period of time following the surgical procedure. Moreover, the highest concentration of bacteria will most likely occur in the vicinity of the implant for the reasons discussed above.

As shown, multiple sensors are used to determine if bacteria is present in proximity to the knee implants. In at least one exemplary embodiment, sensors for detecting the presence are placed in a variety of locations near the knee implant. Bacteria is detected in proximity to the distal end femur 1602 by sensors 1612 that are in and part of femoral implant 1606. Further coverage of the distal end of femur 1602 is obtained by sensors 1614 placed in or attached to the distal end of femur 1614. Similarly, bacteria is detected in proximity to the proximal end of tibia 1604 by sensors 1616 that are in and part of tibial implant 1610. Additional coverage is achieved by sensors 1618 placed in or attached to the proximal end of tibia 1604. Sensors 1612 and 1616 also detect a presence of bacteria between femoral implant 1606 and tibial implant 1610.

Different methods can be used to determine if an infection is present. The biological sensors 1612, 1614, 1616, and 1618 can detect bacteria or other infecting organism by measuring parameters in proximity to the implanted devices such as pH, temperature, viscosity, blood flow, a change in material property corresponding to a change in frequency, and by the detection of cell wall markers. For example, the most prevalent bacteria causing post-operative infections in an implanted joint are the *staphylococcus* bacteria. In the non-limiting example, synovial fluid around the joint can be monitored by sensors 1612, 1614, 1616, and 1618. Non-infected synovial fluid will be within predetermined ranges of pH, temperature, and viscosity. Measuring parameters outside the predetermined ranges can indicate the presence of an infection. A differential analysis can also be used. The synovial fluid can be monitored immediately after the orthopedic device is implanted. The measured parameters are then monitored for changes. A significant change in a measured parameter or a change in combination with the absolute measured value can be used to indicate the presence of an infection.

Sensors 1612, 1614, 1616, and 1618 can comprise more than one sensor type. A combination of sensors providing more than one measured parameter can be used in the determination of the presence of bacteria or an infecting organism. In at least one embodiment, multiple types of sensors are used in and around the implanted device. A sensor can be a sensor array comprising more than one type of sensor integrated into a common housing. Conversely, separate and different types of sensors can be placed where needed. Measuring more than one parameter can aid in the identification of the type of bacteria present or provide early detection of an onset of an infection. The pH of synovial fluid will turn increasingly acidic in the presence of bacteria such as the *Staphylococcus* bacteria. Thus, exceeding a predetermined pH threshold (e.g., equal to or lower than the predetermined threshold value) can trigger an infection event. Similarly, a change in pH above a predetermined differential value (e.g., a negative change in pH) could also be used to trigger the infection event. The temperature of the synovial fluid will rise with the increasing presence of bacteria in synovial fluid. Thus, exceeding a predetermined temperature or exceeding a predetermined positive differential change in temperature can be used to trigger the infection event. The viscosity of the synovial fluid will increase in turbidity, as more bacteria are present. Thus, exceeding a predetermined viscosity or exceeding a predetermined change in viscosity can be used to trigger the infection event. The detection of fluid color can also be applied to some applications. For example, synovial fluid is normally a yellow color that turns to a grey color as the bacteria count rises. Monitoring a change in color can be a useful indication of bacteria and start of an infection.

In at least one exemplary embodiment, a signal can be sent through the synovial fluid and the frequency of the signal is monitored over time. In general, a transmitter and receiver are a fixed distance apart. The synovial fluid passes between the transmitter and receiver. Post-operatively, the signal will have a characteristic frequency corresponding to the fluid properties. This characteristic frequency is indicative of a condition where little or no bacteria are present. A build up of bacteria in the synovial fluid will change how the frequency propagates through the fluid. In at least one exemplary embodiment, a change in propagation time results in a change in the frequency. Thus, a change in frequency can be used to determine the presence of bacteria.

Analysis of a bacterial cell wall is a direct method for determining the presence of bacteria and the type of bacteria. In particular, a sensor looks for one or more components of the bacterial cell wall that comprises an identifying marker. For example, resonance can be used to break apart bacterial cell walls. The components of the cell walls or cell wall fragments in the synovial fluid are detected by the sensor. Detecting the presence of the marker indicates an infection. The concentration of the marker can indicate the level of the infection.

A preventative measure can be a local release to the implanted device region of antibiotics, cytotoxins, or other elements to eliminate bacteria and infecting organisms near the joint. The release of the medicine could occur over a predetermined time period shortly after surgery to implant the device. This can be done during the critical post-surgical period when infection is likely to occur. Local release of medicine where the infection occurs allows a much lower dose to be used. The implementation will be discussed in more detail hereinbelow. Sensors 1612, 1614, 1616, and 1618 can then be used to monitor a region around the implanted device for bacteria although the preventative measures would greatly reduce the likelihood of an infection.

Alternatively, it may not be desirable to release medicine (even locally) unless an infection is imminent. Harmful bacteria are detected when a measured parameter exceeds the predetermined thresholds of sensors 1612, 1614, 1616, and 1618. Since bacteria are present, measures are undertaken to suppress or prevent an infection from occurring. One measure is to send a signal that can be transferred to the doctor or patient indicating a problem. The doctor can, then, prescribe medication to the patient that will eliminate the bacteria or infecting organism before a severe infection occurs. As mentioned above, the system can include a response such as antibiotics and cytotoxins that are released in proximity to the joint when infecting bacteria are found to be within range of the sensors.

In at least one exemplary embodiment, sensors 1612, 1614, 1616, and 1618 comprise a sensor for measuring a parameter, a control circuit, circuitry for wired or wireless communication, and a power source. The control circuit can be a mixed mode circuit having both analog and digital circuitry. The control circuit is configured operatively to the sensor and the communication circuitry to manage when measurements are taken, sending the data for appropriate review or triggering a local response. In one embodiment, each sensor has a control circuit, communication circuitry, and a power source. Each sensor can be powered by a battery or a temporary power source. Alternatively, a single control circuit can be coupled to sensors 1612, 1614, 1616, and 1618 for receiving information from each sensor (wired or wirelessly) and transmitting the measured data to an appropriate client.

In one embodiment, the control circuit includes circuitry to convert the data to a form that can be transmitted by wire or wirelessly. For example, the control circuit can have transmitter/receiver circuitry for transmitting digital or analog data in a standardized communication platform such as Bluetooth. UWB, or Zigbee. In one exemplary embodiment, each control circuit enables each sensor to measure data periodically or by command. Furthermore, the measured data can be stored in memory and sent when appropriate, thereby preventing information from being sent by all sensors simultaneously. A signal can also be generated by each control circuit and sent when a predetermined threshold of sensors 1612, 1614, 1616, and 1618 is exceeded.

The system further includes processing unit 1620 having a screen 1622. Processing unit 1620 is in communication with sensors 1612, 1614, 1616, and 1618. Processing unit 1620 can be a digital processing unit, microprocessor, logic circuit, notebook computer, personal computer, or other similar type device. Processing unit 1620 can control when sensors 1612, 1614, 1616, and 1618 take measurements and send data. Measured parameters from sensors 1612, 1614, 1616, and 1618 can be analyzed by processing unit 1620 and appropriate actions taken. For example, processing unit 1620 can notify the patient that a problem exists, notify the hospital/doctor that an infection has been detected, or take local action by enabling a release of medicine to eliminate the infecting organism (if the action was not already taken by the sensors). The data can be displayed on screen 1622 to show the parameters measured by each sensor such that the location, severity, and infection type is understood.

As shown, sensors 1614 and sensors 1618 can be inserted or attached respectively to femur 1602 and tibia 1604 of the lower leg. For example, sensors 1614 and 1618 can be placed in a housing that has external screw threads. The sensors in a screw type housing can then be attached in bone using tools common to an orthopedic surgeon. Alternatively, the sensors can be temporarily attached to the bone, an implant device, or a surgical tool so they can be removed or disposed of. For example, a sensor array can be pinned to bone for temporary or permanent use. The sensors can also be incorporated into the implanted device as described hereinabove.

Figure 17:
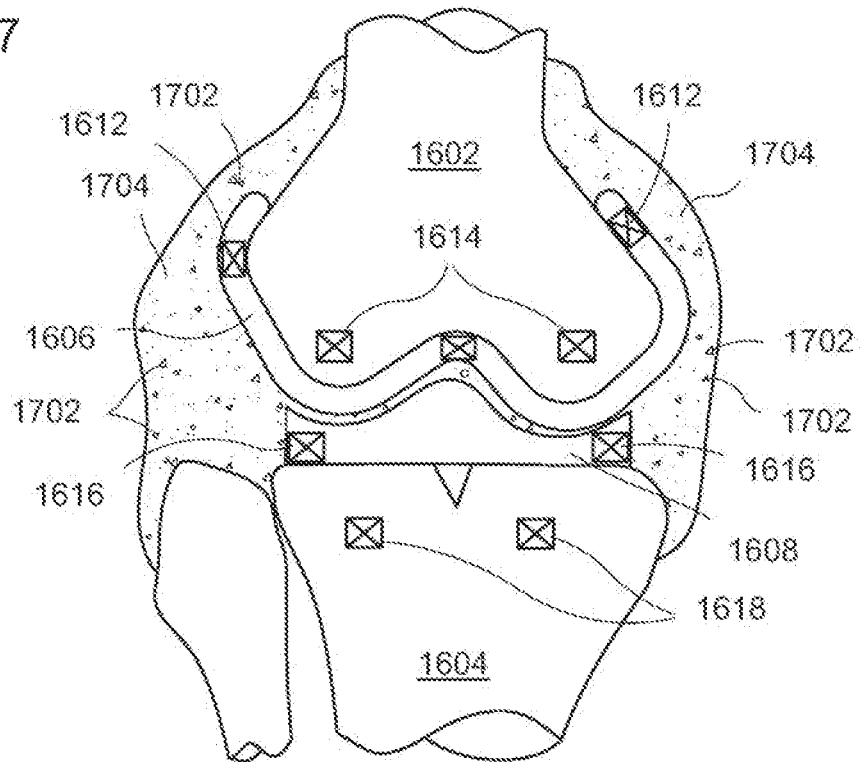
FIG. 17 is a diagrammatic, fragmentary perspective view of an exemplary embodiment of an implanted device having bacteria in synovial fluid around an artificial joint according to the invention.

FIG. 17 is an illustration of an implanted device having bacteria 1702 in synovial fluid 1704 around the artificial joint. A synovial membrane secretes synovial fluid 1704 into a joint space around the joint. Synovial fluid 1704 is a natural lubricant for the contacting surfaces of an articulating joint. The liquid in combination with the artificial joint create an environment that can sustain and fuel the growth of bacteria 1702. The synovial fluid 1704 contains glucose, which bacteria 1702 can feed on. The surfaces and interfaces of the artificial joint form areas in which the bacteria 1702 can have safe harbor as it multiplies and becomes established, which ultimately can lead to sepsis.

Figure 18:
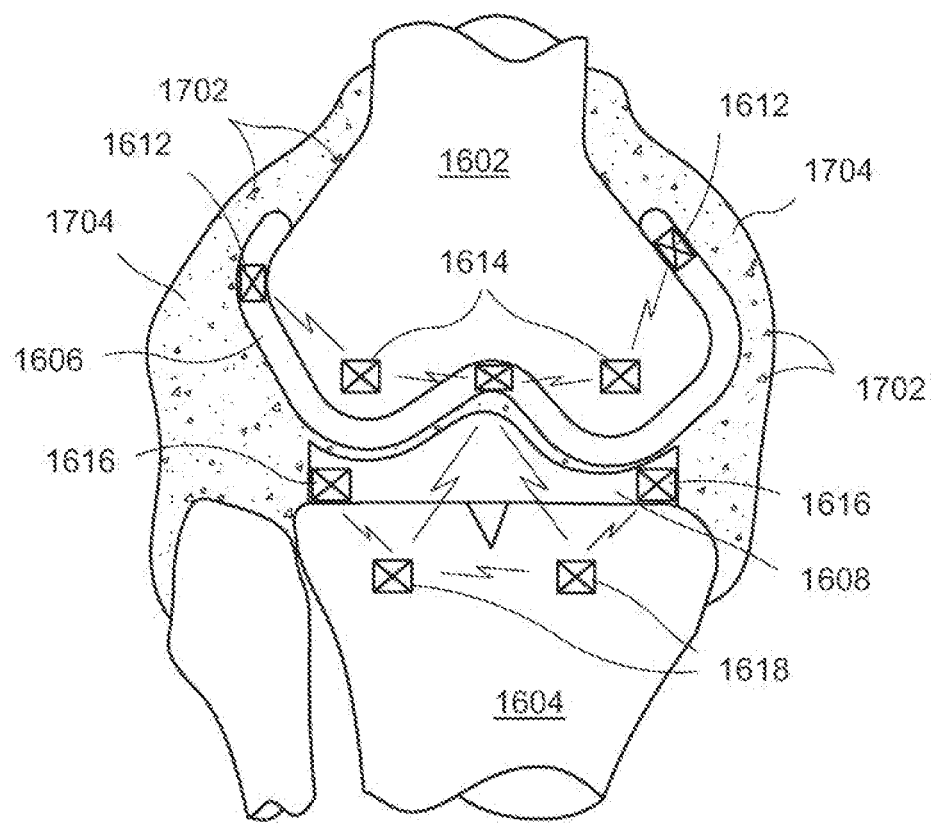
FIG. 18 is a diagrammatic, fragmentary perspective view of an exemplary embodiment of a pulsed electric field emitted in proximity to an implanted device according to the invention.

FIG. 18 is an illustration of a pulsed electric field emitted in proximity to an implanted device in accordance with an exemplary embodiment. In one embodiment, sensors comprising electrodes creating a field are placed in proximity to the implanted device. The sensors are activated to generate a pulsed electrical field in the presence of bacteria 1702 or an infecting organism. The pulsed electric field induces electroporation, which is the act of applying an electrical field to a cell membrane that raises electrical conductivity and increases the permeability of the cell plasma membrane. Sensor system 1800 will activate a pulsed electrical field between two or more of the elements to increase the permeability of bacteria 1702 within the field. Sensor system 1800 will allow modulation of the pulse electrical amplitude, duration, wave number, waveform, and inter-pulse intervals. The predetermined electrical field strength for a predetermined time period will generate a membrane potential that penetrates the cell wall to be activated. Temperature changes and cellular strength can be monitored during the electroporation process. The weakened cell membrane is made more permeable so that the bacteria 1702 can readily receive antibiotics, cytotoxins, or other medicine that can eliminate the bacteria 1702 or an early stage infection. In at least one exemplary embodiment, the medicine is released locally in proximity to the sensors and the implanted device.

In a non-limiting example, sensors 1612, 1614, 1616, and 1618 are electrodes strategically placed to apply an electric field in locations around an implanted knee joint and, more specifically, across volumes of synovial fluid 1704. Alternatively, a micromachined structure can be used to generate the pulsed electric field. One or more sensors detecting a presence of infecting bacteria 1702 can initiate an electroporation process. A doctor or health care professional could also initiate the process by sending a signal to the control circuits of each sensor. A control circuit can be used to sequence the pulsing of sensors 1612, 1614, 1616, and 1618 such that the synovial fluid 1704 and thereby the bacteria 1702 in proximity to the knee implant, distal end of femur 1602, and proximal end of tibia 1604 are subject to electroporation. The control circuit is operatively coupled to a pulsing circuit in each sensor for generating a pulsed voltage. A voltage multiplier can be used to provide a voltage not provided by the power source. In at least one exemplary embodiment, an electric field of between 0.2 kV/cm to 20 kV/cm is used to induce electroporation. Pulse duration is typically from microseconds to milliseconds in length. Pulse shape can also affect the amount of permeability achieved and can be tailored for the specific bacteria 1702 and application.

In at least one exemplary embodiment, two or more components of the implanted device can be electrodes for the electroporation process. For example, in a knee implant, a major surface (or portion thereof) of femoral implant 1606 can be a first electrode. Insert 1608 typically comprises a non-conductive material. A second electrode can be embedded in insert 1608. Similarly, tibial insert can be an electrode. Bacteria 1702 in synovial fluid 1704 between and around the implanted devices would be subject to a pulsed electric field.

Figure 19:
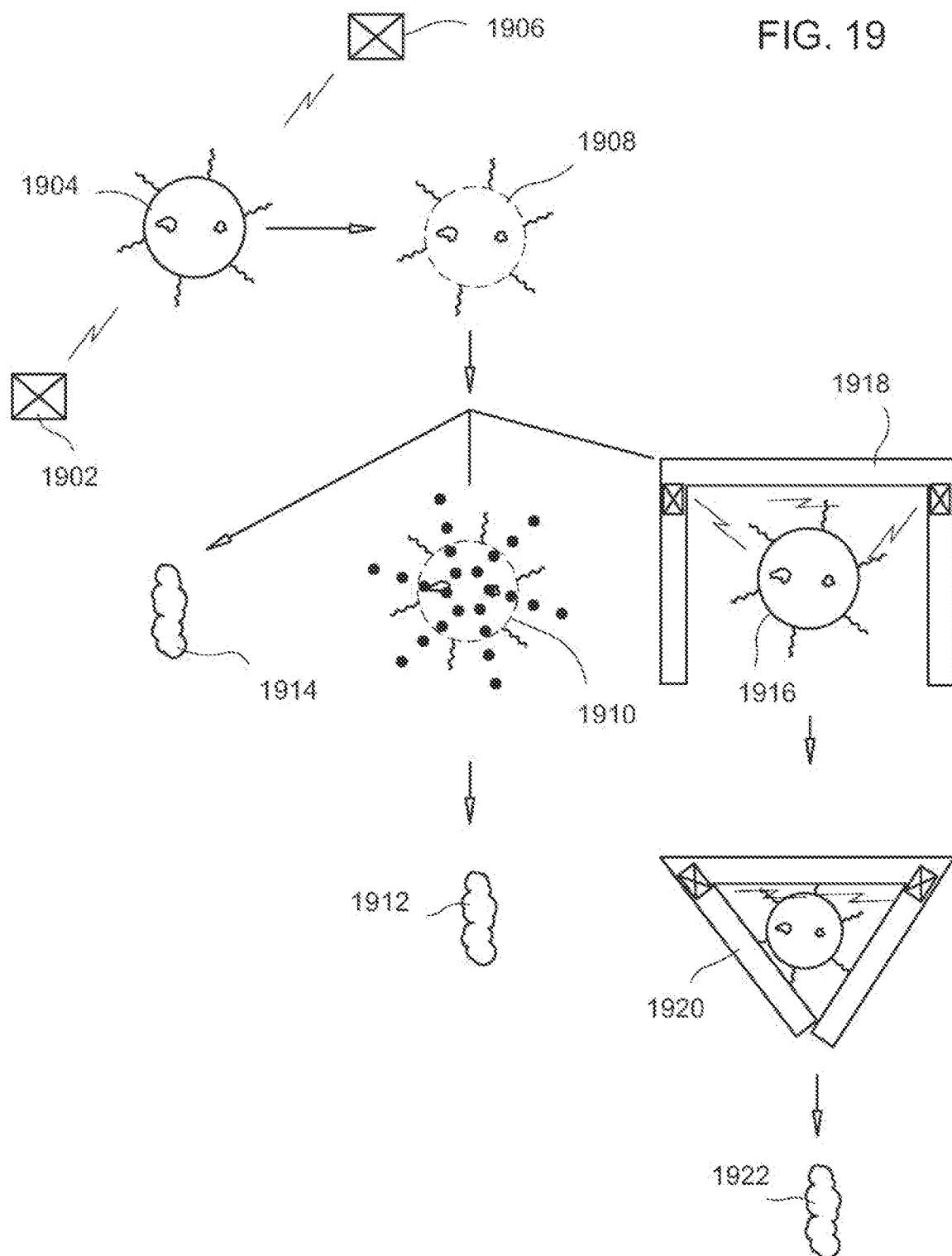
FIG. 19 is a diagrammatic illustration of bacterial response to a field in proximity to an exemplary embodiment of an implanted device according to the invention.

FIG. 19 is an illustration of bacterial response to a field in proximity to an implanted device in accordance with an exemplary embodiment. Sensors 1902 and 1906 are placed on or in proximity to the implanted device. A bacteria in a first state 1904 is between sensors 1902 and 1906. A pulsed voltage is applied across sensors 1902 and 1906 creating a momentary electric field. The pulsed electric field disrupts the cell membrane creating cracks or opening pores of the cell wall to result in a bacteria exhibiting a second state 1908. The openings in the cell membrane can be either temporary or permanent. The bacteria in the second state 1908 have increased permeability from the first state 1904.

The increased permeability of the bacteria in the second state 1908 allows the penetration of antibiotics, cytokines, or other medicines that can be absorbed through the cell wall to kill the bacteria. The medicine can be provided to the body by injection, pills, or other common measures. In at least one exemplary embodiment, a coating is applied to the implanted device or a portion of the implanted device is made of nanostructures that can house hydrogels, antibiotics, cytotoxins, and other elements that, by changing the medium in which the bacteria live, would cause damage to the organism cell wall. For example, the nanostructures can be attached to exposed surfaces of femoral implant 1606, insert 1608, and tibial insert 1610 in areas exposed to synovial fluid 1704. The nanostructures would be activated by a biosensor to release the anti-infective elements while the pulsed electrical field will potentiate uptake by the infecting organism in a third state 1910. Thus, a combination of increased cell wall permeability and local release of medicine to the infected region maximizes delivery into the bacterial cell internal structure. The efficient delivery of the medicine results in a cell death of the bacteria in a fourth state 1912. In at least one exemplary embodiment, the biosensor can target different regions of nanostructures to release medicine, thereby controlling the concentration over time.

A further application of the pulsed electrical field is to destroy the cell wall membrane resulting in the bacteria in a fifth state 1914. In at least one exemplary embodiment, the electric field is pulsed at a resonant frequency of the bacteria. In resonance, the energy applied to the cell walls of the bacteria is additive. Resonance destroys the cell wall membrane such that the organism is killed and/or prevented from multiplying. Reducing the level of the infection by resonant destruction of bacteria allow internal macrophages and lymphocytes to attack the remaining organisms.

As mentioned previously, nanostructures on a surface of the implanted device could contain or be formed from hydrogels. The hydrogel nanostructures can be formed as a compartment having an opening that can receive one or more bacteria. The hydrogel nanostructure can also be made to attract bacteria. For example, the hydrogel can include a chemical that attracts the bacteria. Alternatively, the nanostructure can be polarized or charged to attract the bacteria.

In at least one exemplary embodiment, a bacteria 1916 enters an opened nanostructure 1918 to trap the infective organism. The hydrogel wall of the nanostructure 1918 can be modulated by the biosensors (pH) and the sensors electrical impulses as well as other local mediators. The bacteria 1916 is, thus, identified in nanostructure 1918 and the hydrogel walls collapse to contain bacteria 1916 in a closed nanostructure 1920. Bacteria 1916 cannot multiply or obtain sustenance while contained in nanostructure 1920 and undergo cell death 1922.

It should be realized that a substantial benefit is achieved by having a smart implant that recognizes infection and activates the release of anti-infective elements that will, along with the generation of a pulsed electrical field, lead to cell wall penetration and ultimately death of the infecting organism The smart system utilizes bio-sensors, piezo-sensors, micromachined structures, and nanostructures having a small footprint that can be integrated into an implanted device as well as attached to parts of the body. This will allow the earliest response to infection and the potential to eradicate the infection without the need for surgical intervention or implant removal.

A post-operative pain inhibitor (PPI) is described below that integrates peripheral nerve inhibition in the local post-operative field of the implanted joint. The PPI is a pain modulation system that can be used in conjunction with the skeletal system and, more specifically, with an artificial joint implantation. For illustrative purposes, a knee implant and a hip implant are used to show the operation of the pain inhibitor system. A knee implant is known for being one of the more painful implant surgeries. In general, the PPI is used to alleviate pain related to the skeletal system and can be used for joint implants such as, but not limited to, knee, hip, shoulder, spine, ankle, wrist, prosthetic devices, articulating, and non-articulating bone structures.

FIG. 20 is an illustration of a post-operative pain inhibitor system 2000 for post-operative pain treatment of a skeletal system. In a non-limiting example, a lateral view of a leg is illustrated after a knee replacement surgery has been performed. At least one incision in skin 2001 is used to expose the joint region. The incision gives access to a femur 2002 and a tibia 2003. A knee prosthesis or joint implant 2010 typically comprises a femoral implant, an insert, and a tibial implant. A distal end of a femur 2002 is prepared and receives the femoral implant. In a full knee replacement, the femoral implant has two condyle surfaces that mimic a natural femur. The femoral implant is typically made of a metal or metal alloy. Similarly, a proximal end of tibia 2003 is prepared to receive the tibial implant. The tibial implant is a support structure that is fastened to the proximal end of tibia 2003 and is usually made of a metal or metal alloy. An insert is fitted between the femoral implant and tibial implant. In the full knee replacement, the insert has two bearing surfaces in contact with the two condyle surfaces of the femoral implant that allow rotation of the lower leg under load. The tibial implant retains the insert in place. The insert is typically made of a high wear polymer that minimizes friction.

Post-operative pain inhibitor system 2000 comprises a controller 2032 coupled to topical leads 2027 and percutaneous leads 2025. System 2000 can address pain control during and after joint replacement. Pain affects a patient's recovery and hinders early joint function. Common effects of pain following total knee replacements include depression, tachycardia, insomnia, reflex muscle spasm and sometimes chronic regional pain syndromes. Research has shown that pre-operative pain control has a positive effect on the severity of pain post-operatively. Intra-operative anesthetic control is critical. Narcotic medication is still needed for joint implants and especially for total knee replacements. Pain control is variable and the common side effects (nausea, vomiting, itching, ileus, confusion, respiratory depression)

often interfere with rapid recovery. Post-operative pain inhibitor system 2000 can reduce reliance on other pain control methods or be used in conjunction with the methods to deliver a more consistent and higher level of pain reduction.

In at least one exemplary embodiment, one or more leads are placed in proximity to the operative field of the implanted joint. Controller 2032 is shown connected by wire to topical lead 2027 and percutaneous leads 2025. Controller 2032 provides a signal to leads 2025 and 2027, which are used to transfer pulses of electrical energy to stimulate peripheral nerve fibers to inhibit or block a pain signal, thereby reducing the pain perceived by the patient. Either type of lead may be used, or both types may be used in combination, to achieve adequate pain control.

In general, low amplitude current is used to stimulate the peripheral nerve fibers. Topical lead 2027 and percutaneous leads 2025 are current injecting components that receive a signal from controller 2032. Topical leads 2027 are placed on a surface of skin 2001 to make electrical contact. Percutaneous leads 2025 include a contact region that punctures or couples through the outer skin layer to make contact. Leads 2025 and 2027 are attached to a predetermined position on the patient's body, which is typically in the vicinity, but is not limited to, the operative field where the orthopedic device was implanted and a peripheral nerve fiber.

The lateral view of the leg illustrates two embodiments of a wired electrical connection from neuro-stimulator circuitry of controller 2032 to stimulate peripheral nerves for the inhibition of pain. A first embodiment comprises a placement of topical leads 2027 with a wired connection to controller 2032. The second embodiment is the placement of a percutaneous lead 2025 with a wired connection to controller 2032. In both cases, the electrical pulses travel through external wires to terminate in the lead affixed to the patient's skin 2001. In the case of the knee implant, leads 2025 and 2027 are shown contacting skin 2001 in proximity to the implanted knee. Leads 2025 and 2027 provide an electrically conductive contact to the skin in which to direct the current to the peripheral nerve fiber. The low-amplitude pulsed current provided by the neuro-stimulator circuitry of controller 2032 blocks the propagation of body generated action potentials.

Pain signals are carried by small, slow conducting peripheral nerve fibers (C-fibers). The pain signals can be blocked by stimulation of the large diameter, rapidly conducting peripheral nerve fibers (A-fibers). The balance between A-fibers and C-fibers determines the degree of pain. Stimulation of A-fibers by a variety of stimuli (scratching, pressure, vibration, or electrical stimulation) with little or no stimulation of C-fibers will close the gate. Thus, controller 2032 in conjunction with leads 2025 and 2027 stimulate the A-fibers with a current pulse to close the gate and block the propagation of pain signals carried by the C-fibers, thereby reducing perceived pain by the patient.

In at least one exemplary embodiment, a bipolar electrode device can be used to electrically contact skin 2001 and deliver a signal to inhibit a body generated pain signal propagating in a peripheral nerve fiber. The bipolar electrode device corresponds to leads 2025 and 2027. The bipolar electrode device has an anode and a cathode. In a non-limiting example, the anode of the bipolar electrode device is placed in close proximity to the peripheral nerve fiber and the operative field. The cathode of the bipolar electrode device is placed away from the anode in a region of low sensitivity. Sufficient energy is provided by controller 2032 to hyperpolarize the peripheral nerve fiber.

Alternatively, a tri-polar electrode device can be used to selectively block the propagation of body generated action potentials traveling through a nerve bundle. The tri-polar electrode device corresponds to leads 2025 and 2027. The tri-polar electrode device comprises a first anode, a second anode, and a cathode. In a non-limiting example, the cathode is placed between the first and second anodes. A pulse is provided to the peripheral nerve fiber from both anodes. The cathode can be placed non-equidistant between the anodes. The signals provided by each anode can be different. The tri-polar electrode generates a uni-directional action potential to serve as collision block with body-generated action potentials representing pain sensations in the small-diameter sensory fibers of a peripheral nerve fiber.

In at least one exemplary embodiment, controller 2032 is accessible to the patient. It should be understood that each patient is different and each will have varying ability to cope with pain. Furthermore, placement of the leads 2025 and 2027 and the conducting distance will also vary. In a non-limiting example, controller 2032 couples to a belt that can be wrapped and held at the waist of the patient. Controller 2032 includes controls such as dials, switches, a keyboard, a touch panel, a touch screen, or a wireless interface. The controls on controller 2032 are used to modify the signal provided to leads 2025 and 2027. The controls of controller 2032 are coupled to a logic unit, a signal generator, a power source, and communication circuitry to generate electrical impulses tailored to an individual's need for appropriate pain relief in terms of pulse frequency, pulse width, and pulse amplitude. Thus, a signal provided by system 2000 can be tailored for the individual. Controller 2032 can include a digital signal processor, a microprocessor, a microcontroller, logic circuitry, and analog circuitry to generate the appropriate signal. The post-operative pain inhibitor (PPI) comprising controller 2032 and leads 2025 and 2027 integrates electrically mediated pain relief and can be controlled by the patient and modify the pulse amplitude, width, wave shape, repetition rate, and zone migration frequency as it relates to their pain threshold. In at least one embodiment, leads 2025 or 2027, or other sensing structures in contact with the patient's body, can be a device to monitor perspiration, monitor heat, modify impulses to affect swelling, monitor EMG integration, and monitor inflammatory markers.

FIG. 21 is an anteroposterior view of a leg in accordance with an exemplary embodiment. The anteroposterior view illustrates positioning of the post-operative pain inhibitor system 2000 in relation to the leg, the operative field, and the joint implant 2010. Controller 2032 is attached by a belt to the patient. Controls of controller 2032 are easily accessible to the patient to modify the signals output by neuro-stimulator circuitry residing therein. Topical leads 2027 and percutaneous leads 2025 are electrically coupled to skin 2001 to provide a signal to peripheral nerve fibers. Topical lead leads 2027 are attached and positioned in proximity to femoral implant 2012 on both the medial and lateral sides of the knee. Percutaneous leads 2025 includes a point that punctures the skin 2001 (for better contact) and are positioned in proximity to tibial implant 2014 on both the medial and lateral sides of the knee. Topical leads 2027 and percutaneous leads 2025 are within the operative field of the implanted joint. Both types of leads 2025 and 2027 can be used to transfer pulses of electrical energy and stimulate peripheral nerve fibers to inhibit propagation of body generated action potentials related to pain. As shown, leads 2025 and 2027 are connected to controller 2032 by a wire. Controller 2032 outputs electrical pulses that travel through the external wires to an attachment point on each of leads 2025 and 2027. Controller 2032 is portable and can be powered by a wired-power supply, a battery, a rechargeable battery, or other powering scheme. The portability allows the patient to actively use post-operative pain inhibitor system 2000 during a rehabilitation process.

FIG. 22 illustrates an anteroposterior view of a post-operative pain inhibitor system 2000 for post-operative pain treatment of the skeletal system in accordance with an exemplary embodiment. The anteroposterior view illustrates positioning of the post-operative pain inhibitor system 2000 in relation to the leg, the operative field, and the joint implant 2010. Controller 2032 is attached by a belt to the waist of the patient. Controls of controller 2032 are easily accessible to the patient to modify the signals output by neuro-stimulator circuitry residing therein. Subcutaneous leads 2026 underlie skin 2001 and can be positioned close to peripheral nerve fibers to enhance the efficacy of pain modulation. Subcutaneous leads 2026 can be placed in the tissue during the implantation of femoral implant 2012 and tibial implant 2014 respectively to femur 2002 and tibia 2003. The surgeon can view the operative field and map the region for optimal placement of subcutaneous leads 2026 resulting in lower power utilization and better pain control. In a non-limiting example, leads 2026 are shown positioned in proximity to femoral implant 2012 on both the medial and lateral sides of the knee and in proximity to tibial implant 2014 on both the medial and lateral sides of the knee.

In at least one exemplary embodiment, a transmitter/receiver 2043 is used to communicate to controller 2032 and subcutaneous leads 2026. Transmitter/receiver 2043 is in a housing affixed to skin 2001 in proximity to leads 2026. Transmitter/receiver 2043 can include neuro-stimulator circuitry to generate a signal for blocking propagation of body-generated action potentials. In at least one exemplary embodiment, controller 2032 is in wireless communication with transmitter/receiver 2043. Controller 2032 includes an interface to allow the patient to adjust the pulse amplitude, width, wave shape, repetition rate, and zone migration frequency in conjunction with transmitter/receiver 2043. Alternatively, transmitter/receiver 2043 can be wired to controller 2032. Transmitter/receiver 2043 radiates pulses of electrical energy to an implanted conductor with one or more subcutaneous leads 2026 positioned in the vicinity of femoral implant 2012 and tibial implant 2014 to provide effective peripheral nerve stimulation. In an alternate embodiment, a hub 2045 can be affixed to the patient's skin 2001. Hub 2045 is directly connected to an implanted conductor with one or more subcutaneous leads 2026 positioned in the vicinity of femoral implant 2012 and tibial implant 2014 to provide effective peripheral nerve stimulation.

Figure 24:
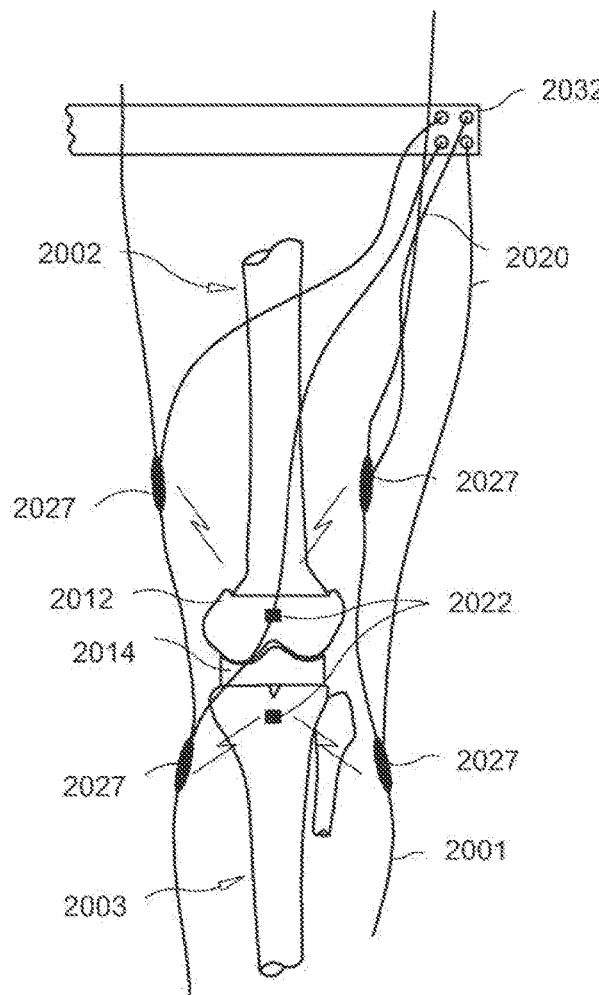
FIG. 24 is a diagrammatic, fragmentary perspective anteroposterior view of an exemplary embodiment of a post-operative pain inhibitor system for post-operative pain treatment of the skeletal system according to the invention.

FIG. 23 is a lateral view of post-operative pain inhibitor system 2000 in accordance with an exemplary embodiment. The lateral view illustrates positioning of the post-operative pain inhibitor system 2000 in relation to the leg, operative field, and joint implant 2010. Controller 2032 is attached by a belt to the patient, e.g., at the waist. Controls of controller 2032 are easily accessible to the patient to modify the signals output by neuro-stimulator circuitry residing therein. Subcutaneous leads 2026 underlie skin 2001 and can be positioned close to peripheral nerve fibers to enhance the efficacy of pain modulation. In a non-limiting example, leads 2026 are shown positioned in proximity to femoral implant 2012 on both the medial and lateral sides of the knee and in proximity to tibial implant 2014 on both the medial and lateral sides of the knee. In a non-limiting example, leads 2026 are shown positioned in proximity to femoral implant 2012 on both the medial and lateral sides of the knee and in proximity to tibial implant 2014 on both the medial and lateral sides of the knee, FIG. 24 illustrates an anteroposterior view of a post-operative pain inhibitor system 2000 for post-operative pain treatment of the skeletal system in accordance with an exemplary embodiment. Controller 2032 is attached by a belt to the patient, e.g., at the waist. Controls of controller 2032 are easily accessible to the patient to modify the signals output by neuro-stimulator circuitry residing therein. In at least one exemplary embodiment, system 2000 includes an addition of intraosseous leads 2022 to enhance the efficacy of pain modulation. Intraosseous leads 2022 are respectively coupled to femur 2002 and tibia 2003. In a non-limiting example, intraosseous leads 2022 can be attached to or inserted in bone during the implantation of an orthopedic joint. In general, intraosseous leads 2022 are attached to bone of the skeletal system in proximity to a peripheral nerve fiber.

In at least one exemplary embodiment, topical leads 2027 can include transmitters to radiate pulses of electrical energy to implanted intraosseous leads 2022. Topical leads are connected by wire to controller 2032. Topical leads 2027 are placed in proximity to intraosseous leads 2022. More specifically, one or more topical leads 2027 having transmitters are positioned on skin 2001 of the patient in proximity to the distal end of the femur 2002 where a first intraosseous lead 2022 resides. Similarly, two additional topical leads 2027 having transmitters are positioned on the skin 2001 of the patient in proximity proximal end of tibia 2003 where a second intraosseous lead 2022 resides. Each topical lead 2027 radiates pulses of electrical energy to an implanted conductor within intraosseous leads 2022. The pulsed electrical energy is received by intraosseous leads 2022 and conducted within the bone to create an operative field stimulating the peripheral nerve fiber to block propagation of body generated action potentials corresponding to pain. The patient can change or modify the signal provided to intraosseous leads 2022 by modifying pulse amplitude, pulse width, wave shape, repetition rate, and zone migration frequency using controller 2032 thereby affecting perceived pain to the patient and tailoring the signal for the individual.

Alternatively, intraosseous leads 2022 can include a transmitter/receiver and a power source such as a battery. An external powering coil could also be used to energize intraosseous leads 2022 or to recharge the battery. Intraosseous leads 2022 can be in wireless communication with topical leads 2027 or controller 2032. Using low amplitude current pulses to block the body generated action potentials system 2000 could be operated over a significant period of time.

Figure 25:
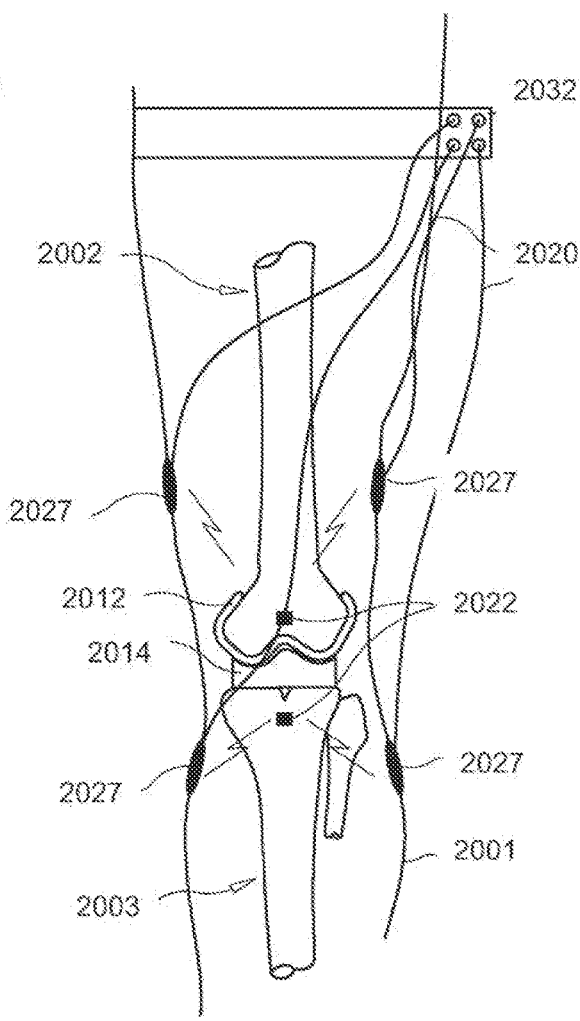
FIG. 25 is a diagrammatic, fragmentary perspective lateral view of an exemplary embodiment of a post-operative pain inhibitor system for post-operative pain treatment of the skeletal system according to the invention.

FIG. 25 is a lateral view of post-operative pain inhibitor system 2000 in accordance with an exemplary embodiment. The lateral view illustrates positioning of the post-operative pain inhibitor system 2000 in relation to the leg, operative field, and joint implant 2010. Controller 2032 is attached by a belt to the patient, e.g., at the waist. Controls of controller 2032 are easily accessible to the patient to modify the signals output by neuro-stimulator circuitry residing therein. Intraosseous leads 2022 are attached to femur 2002 and tibia 2003 close to peripheral nerve fibers to enhance the efficacy of pain modulation. In a non-limiting example, leads 2027 are shown positioned in proximity to the distal end of femur 2002 and proximal end of tibia 2003 on both the medial and lateral sides of the knee. Controller 2032 is in wired communication with topical leads 2027 while topical leads are in wireless communication with intraosseous leads 2022 as described hereinabove.

FIGS. 26a and 26b are illustrations of a prosthetic component having integrated electrical leads to provide a signal to a peripheral nerve fiber to reduce post-operative pain, in a non-limiting example, the prosthetic component is a femoral implant. In general, a distal end of a femur is prepared and shaped to receive a femoral implant. In at least one exemplary embodiment, a profile of the femoral implant is shaped similar to existing implants being offered such that the device can be installed using procedures and practices known to the surgeon. Although shown as femoral implant, the principles and structures described herein can be applied to a wide range of orthopedic prosthesis as well as other implanted medical devices.

An antereoposterior view of the femoral implant is shown. The illustration is viewed towards the condyle surfaces of the femoral implant. Circuitry 2044, within or underlying peg lugs 2019 is coupled with leads 2020 through an electrical interconnect. In a non-limiting example, the interconnect can be wire, flex interconnect, or other suitable electrically conducting material. The interconnect connects from peg lugs 2019 to leads 2020. Leads 2020 are exposed on the surface of the prosthetic component. Leads 2020 are positioned around a peripheral surface at a distal end of the femoral implant. The location is such that leads 2020 are exposed through most or all of a lower leg rotation. In at least one exemplary embodiment, peg lugs 2019 extend into an interior surface of the femoral implant. The lateral view of femoral implant illustrates peg lugs 2019 extending from the surface of the femoral implant. The femoral implant is C-shaped having an outer surface that mimics a natural condyle surface. The interconnect is placed overlying or interior to the internal surface of the femoral implant connecting peg lugs 2019 to leads 2020.

Many neuro-stimulation procedures require precise positioning of electrical leads. Similarly, an orthopedic joint implant requires precise positioning of the prosthesis components to the skeletal system corresponding to location, distance, relational bone-to-bone positioning, balance, and alignment. Integration of leads 2020 into a prosthesis component takes advantage of this precise positioning within the body that is a very repeatable and consistent procedure. Thus, integration of leads 2020 on the surface of a prosthetic component, or components, or within prosthetic components, enables accurate placement of the leads 2020 automatically with the same high level of accuracy as the placement of the prosthesis itself. There is no added surgical time to incorporate the post-operative pain inhibitor because the inhibitor is incorporated in the implant thereby minimizing stress on the patient. Moreover, this reduces cost because the device can be implemented without requiring the assistance of a neurosurgeon. Ultimately, patient benefits including less post operative pain (under user control) and faster recovery are achieved with minimal impact to the complexity, cost, and length of the surgery.

Circuitry 2044 can further comprise additional circuitry that is placed in femoral implant 2012, for example, sensors and circuitry as described herein. Circuitry 2044 can process a received signal from a controller as described herein to support driving leads 2020 to output a pulsed signal appropriate to stimulate a peripheral nerve fiber in proximity to leads 2020 to block a body generated pain signal. The pulsed signal output by leads 2020 can be processed or modified in different ways. In a first embodiment, processing by circuitry 2044 is minimal with leads 2020 directly connected to neuro-stimulator circuitry external to the patient through a transcutaneous lead. The neuro-stimulator circuitry can be located in the controller or on or near the transcutaneous lead. In a second exemplary embodiment, one or more topical leads having a transmitter is connected to neuro-stimulator circuitry external to the patient. The topical leads are affixed to the skin of the patient in proximity to femoral implant 2012. Pulses of electrical energy corresponding to a signal provided to the peripheral nerve fiber are coupled wirelessly to circuitry 2044 integrated into the femoral component 2012. In a third exemplary embodiment, circuitry 2044 can further comprise a power source and neuro-stimulator circuitry to control pain under control of the patient controller. The neuro-stimulator circuitry is located in the femoral implant and can generate appropriate waveforms under patient control to stimulate the peripheral nerve fibers to reduce pain.

In at least one exemplary embodiment, circuitry 2044 is integrated within the femoral component and positioned within or underlying peg lugs 2019. A receiver circuit of circuitry 2044 can be embedded within the femoral component to wirelessly couple electrical energy radiated by an external source, such as, but not limited to, an induction loop or antenna. The energy received by the induction loop or antenna can be coupled directly to transmitter circuitry of circuitry 2044 that is provided to leads 2020 to be radiated to the peripheral nerve fiber. Circuitry 2044 can further comprise an energy storage capacity that includes, but is not limited to, a battery, a capacitor, a supercapacitor, an ultracapacitor, or other measures for continuous reception of external energy. The embedded receiver can be coupled to the energy storage capacity to power circuitry 2044 and more specifically neuro-stimulation circuitry in the femoral implant. The output of the neuro-stimulation circuitry is coupled to the leads 2020 to provide the pain blocking waveform to the peripheral nerve fiber.

Another variation is the integration of an intraosseous lead or leads into the tip or tips of the peg lugs 2019. The intraosseous leads can be included in addition to the leads on the perimeter of the femoral implant to supplement coupling of the stimulation signal to the peripheral nerve fiber. Intraosseous leads can also be used in place of the leads 2020 to output a signal that stimulates the peripheral nerve fiber. The intraosseous leads are under the control of the controller as are leads 2020.

FIG. 27 is an illustration of components of a post-operative pain inhibitor system 2000 integrated into a number of prosthetic components. As mentioned previously, incorporating leads into an orthopedic implant component to stimulate peripheral nerve fibers for reducing pain is beneficial because of proximity to the operative field and peripheral nerve fibers as well as the precise positioning of the component. There may be situations where patients require multiple joint prostheses to raise their quality of life. In such instances, post-operative pain inhibitor system can be used in conjunction with each implanted component. In at least one exemplary embodiment, a single patient controller 2032 can control each implanted component having integrated leads to affect body generated potentials in proximity to each implanted region.

A leg is illustrated having both a hip implant 2017 and a knee implant 2014. The knee implant 2014 has been described in detail hereinabove. A hip replacement typically comprises a cup 2011, a bearing 2711, and a femoral implant 2013. In at least one exemplary embodiment, cup 2011 comprises metal or other material of high strength. The surgeon reams out the acetabulum area of the pelvis to fit cup 2011. The fitting of cup 2011 requires precise positioning in the reamed out acetabulum and is typically a compression fitting. The bearing 2711 is then fitted into cup 2011 for providing a low friction low wear surface in which a femoral head of femoral implant 2013 is fitted. The bearing 2711 typically comprises a polymer material such as ultra high molecular weight polyethylene. In general, a predetermined amount of surface area of femoral head is in contact with the surface of bearing 2711 to minimize loading and wear on the material. The surgeon prepares femur 2002 to receive and retain femoral implant 2013. Femoral implant 2013 is fastened into a proximal end of femur 2002. Femoral implant 2013 comprises a strong lightweight material and typically comprises a metal or metal alloy. The hip and knee replacement components are selected to be formed of biologically compatible materials.

Femoral implant 2012 and tibial implant 2014 of the knee implant include circuitry and leads to stimulate peripheral nerve fibers in proximity to the operative field of the knee. Similarly, femoral implant 2013 includes circuitry and leads to stimulate peripheral nerve fibers in proximity to the operative field of the hip. As disclosed above, controller 2032 is operatively coupled to provide a signal to the leads of femoral implant 2013, femoral implant 2012, and tibial implant 2014. Controller 2032 further provides patient control of the signal provided to each implant thereby allowing the patient to tailor the signal waveform to minimize perceived pain in the knee and hip regions. The anteroposterior view illustrates the relative positions of cup 2011, femoral implant 2013, femoral implant 2012, and tibial implant 2014. The example illustrates post-operative pain inhibitor system 2000 having more than one active component but is not limited to multiple device applications.

Figure 28:
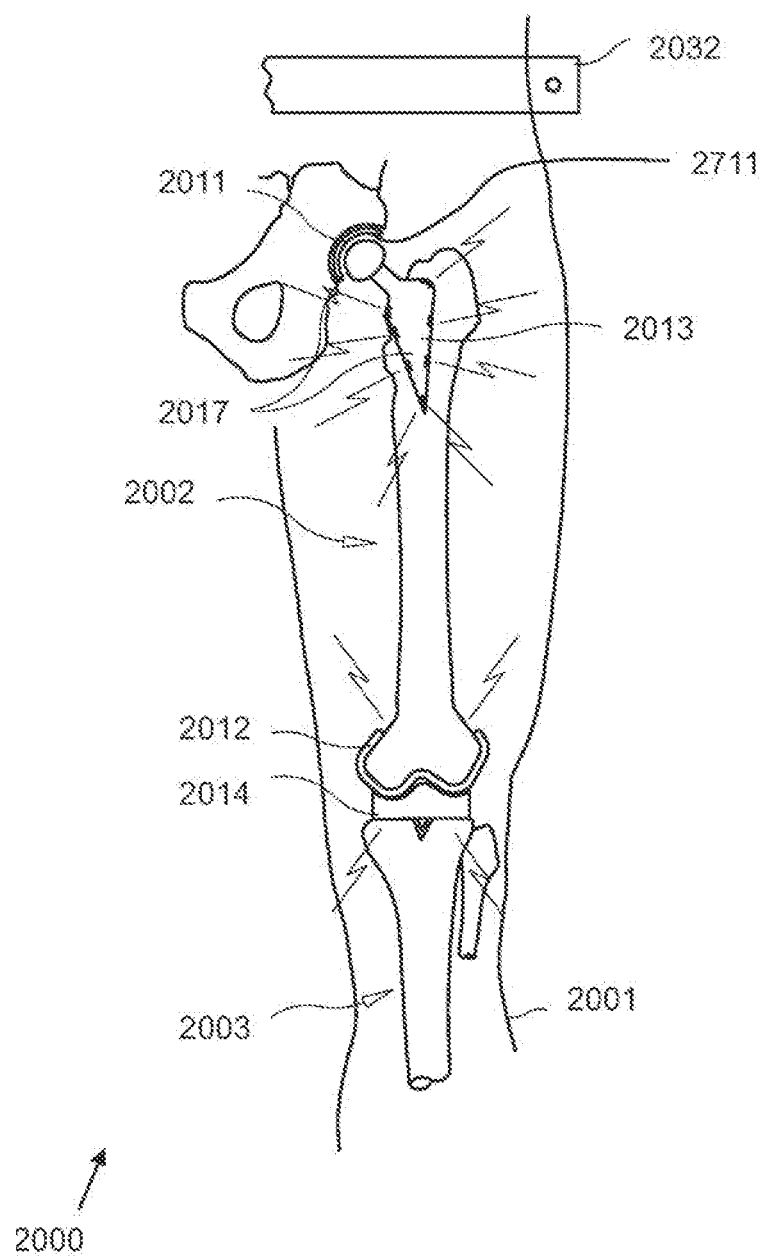
FIG. 28 is a diagrammatic, fragmentary perspective lateral view of an exemplary embodiment of components of the post-operative pain inhibitor system integrated into more than one prosthetic components according to the invention.

FIG. 28 is a lateral view of post-operative pain inhibitor system 2000 in accordance with an exemplary embodiment. The lateral view illustrates positioning of the post-operative pain inhibitor system 2000 in relation to the leg, operative field, and joint implant. Controller 2032 is attached by a belt to the waist of the patient. Controls of controller 2032 are easily accessible to the patient to modify the signals output by neuro-stimulator circuitry residing therein. The lateral view illustrates femoral implant 2013 in a hip region. It also illustrates femoral implant 2012 and tibial implant 2014 in the knee region. The implants have leads that are exposed in periodic spacing circumferentially around the implant to maximize signal coverage. Alternatively, the leads can be placed in specific locations that are in proximity to a peripheral nerve.

Figure 29:
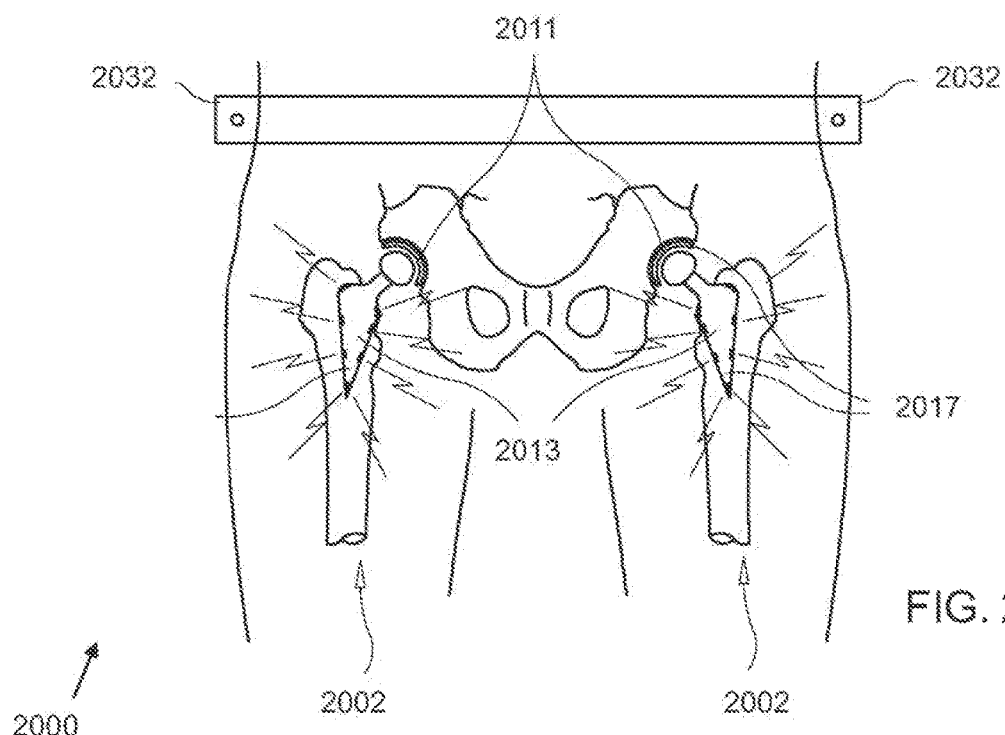
FIG. 29 is a diagrammatic, fragmentary perspective anteroposterior view of an exemplary embodiment of a hip prosthesis according to the invention.

FIG. 29 is an illustration of hip prosthesis 2017 in accordance with an exemplary embodiment. Each leg has femoral implant 2013 coupled to a proximal end of femur 2002. Each femoral implant 2013 includes leads for coupling to a peripheral nerve fiber in proximity to the joint implant. As disclosed hereinabove, femoral implant 2013 can house circuitry and a power supply. Controller 2032 is coupled to the leads of each femoral implant for providing a signal. The signal can be controlled by the patient. The leads of each implant output the signal to block body generated action potential in the peripheral nerve corresponding to a pain signal. Controller 2032 can modify the signal under user control to each femoral implant 2013 to a waveform that minimizes perceived pain for each leg in proximity to the hip region.

In general, an invasive procedure such as hip surgery causes chemicals in the body to be released due to the incision and subsequent damage to the surrounding tissue as the bone is modified and the implants are put in place. The bodily generated chemicals greatly sensitize the local nociceptors causing substantial pain to the patient. Gate theory implies that the bodily generated action potentials propagating to the peripheral nerve fibers can be opened or closed. Post-operative pain inhibitor system 2000 reduces the propagation of the signals by stimulating the peripheral nerve fibers to close the gate. As mentioned previously, the signal coupled to the peripheral nerve fibers are low current pulses. In general, a typical frequency of the pulses is in the range of 200 Hz to 20,100 Hz. One exemplary beneficial frequency is approximately 10,000 Hz.

The circuitry placed in femoral implant 2013 comprises a power source, such as a battery and electronic circuitry to energize electrical leads or to radiate electrical stimuli into the field of stimulation. The latter circuitry is referred to as a transmitter. Wireless nerve stimulators can be powered by receiving externally generated electrical energy as input to the transmitter. This receiving circuitry is referred to as a receiver. The provided energy can be continuous or intermittent. If the energy is provided intermittently, a capacity for storing electrical energy can be used such as a battery, a capacitor, or an inductor.

Figures 30A, 30B:
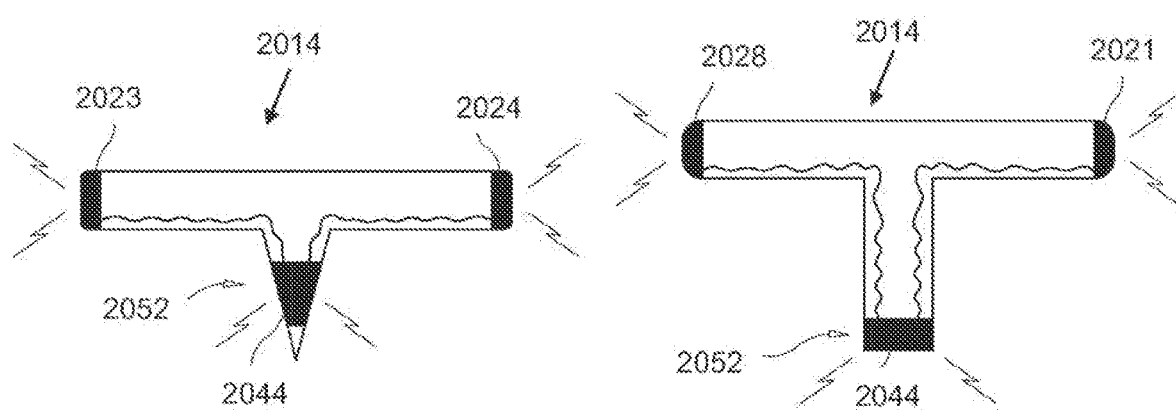

FIGS. 30a and 30b are illustrations of a tibial implant 2014 in accordance with an exemplary embodiment. The tibial implant 2014 is a support and retaining structure for the insert of the prosthetic system. Leads 2021, 2023, 2024, and 2028 are integrated into tibial implant 2014. The anteroposterior and lateral views of the tibial component illustrate the placement of the leads 2021, 2023, 2024, and 2028 that are exposed on the perimeter of the tibial component 2014. The leads couple to neuro-stimulation circuitry in one of the tibial implant 2014, a housing attached to skin, or in a controller. Leads 2021, 2023, 2024, and 2028 provide signals to peripheral nerve fibers to block body generated action potentials under patient control via the controller as described hereinabove. Circuitry 2044 can be integrated in many locations within the tibial implant 2014. In one exemplary embodiment, circuitry 2044 is housed in stem 2052 of tibial implant 2014.

In at least one exemplary embodiment, an intraosseous lead or leads are positioned on or integrated within the tip (not shown) of the stem 2052 of the tibial implant 2014. In one exemplary embodiment, the intraosseous leads are in addition to leads 2021, 2023, 2024, 2028 on the perimeter of the tibial component 2014. In a second exemplary embodiment, the intraosseous leads can be used in place of one or more leads 2021, 2023, 2024, and 2028. The intraosseous leads provide a conductive field of operation that provides effective peripheral nerve stimulation.

Figure 31A:
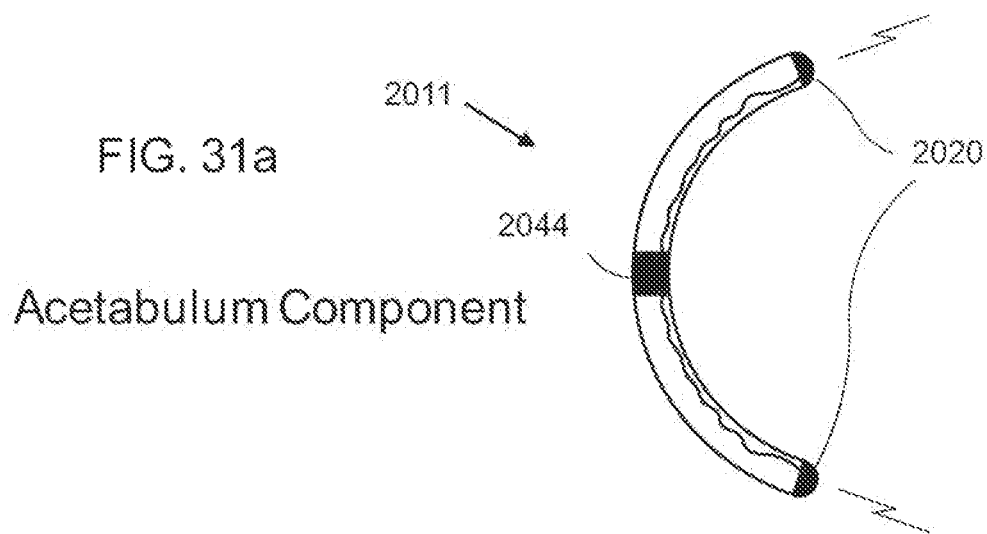
FIG. 31a a diagrammatic, fragmentary, lateral view of an exemplary embodiment of a cup implant according to the invention.
Figure 31B:
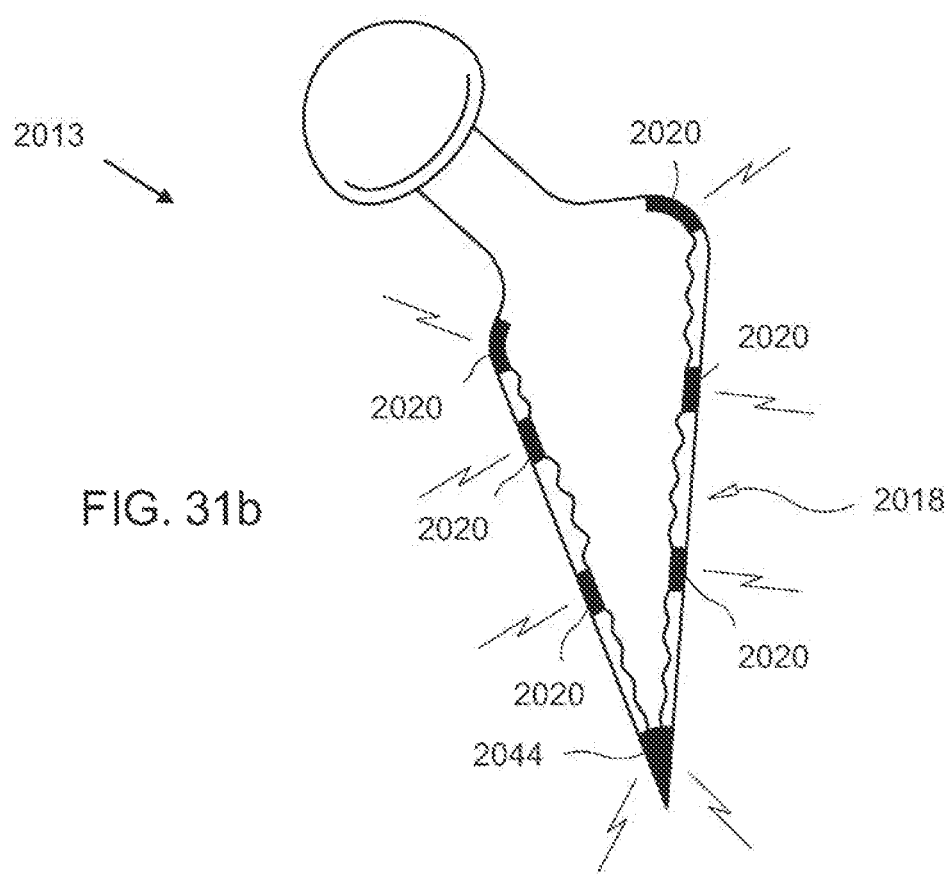
FIG. 31b a diagrammatic, fragmentary, anteroposterior view of an exemplary embodiment of a femoral implant according to the invention.

FIGS. 31a and 31b are illustrations of a cup implant 2011 and a femoral implant 2013, respectively, in accordance with an exemplary embodiment. Cup implant 2011 is also known as an acetabulum component. The anteroposterior view of femoral implant 2013 illustrates exposed leads positioned circumferentially and in different areas of implant 2013. The leads are connected by wire to circuitry 2044 that can be formed in, internal to, or external to femoral implant 2013. As shown, wires are placed along the sides of the stem 2018 of the femoral implant 2013 or integrated within the perimeter of the stem 2018 of the femoral implant 2013 of the hip prosthesis. In a non-limiting example, circuitry 2044 can be placed in a tip region of femoral implant 2013. Circuitry 2044 can include a power source and a transmitter/receiver. Circuitry 2044 in conjunction with the exposed leads generates a field of operation that provides effective peripheral nerve stimulation. The nerve stimulation can be modified using patient controller 2032.

The lateral view of cup 2011 illustrates the placement of leads 2020 positioned on or integrated into the perimeter of the cup 2011. Circuitry 2044 can be integrated in many locations within the cup 2011. In a non-limiting example, circuitry 2044 is shown in a central region of cup 2011.

A further variation includes intraosseous lead or leads positioned on or integrated within the tip of stem 2018 of the femoral component 2013. In a first exemplary embodiment, the intraosseous lead or leads are addition to the leads on the perimeter of femoral implant 2013. In a second exemplary embodiment, intraosseous leads are used solely to create an operative field that provides effective peripheral nerve fiber stimulation in conjunction with external patient controller 2032.

While the above exemplary embodiments of pain inhibitor systems describes leads and sensors related to pain inhibition, these systems are not limited to pain inhibition and likewise can include, in addition to the pain inhibition leads, all sensor systems described hereinabove and hereinbelow.

Another exemplary sensor system according to the present invention depicts mainly the hip and spine, but can be applied to all skeletal segments of the body. FIGS. 32, 33, and 41-45 depict various orientations of sensors according to the invention for treating the knee, hip, and vertebrae.

By way of the device contemplated herein, the surgeon receives measured data during surgery and post-operatively on the factors listed above. As one example, accurate measurements can be made during joint implant surgery to determine if an implant is optimally balanced and aligned. This can reduce operating time and surgical stress for both the surgeon and patient. The data generated by direct measurement of the implanted joint can be further processed to assess joint integrity, operation, and joint wear, thereby leading to improved design and materials.

As one example, load balance adjustment can be achieved by soft tissue release in response to the assessment. The surgeon or device can reduce tension on one or more ligaments to modify loading to a more optimal situation. In this scenario, the surgeon receives measured data by way of the device during surgery and post-operatively on the factors listed above. Consequently, the surgical outcome is a function of the device as complemented with the surgeon's abilities but not so highly dependent alone on the surgeon's skill. The device captures the "feel" of how an implanted device should properly operate to improve precision and minimize variation, including haptic and visual cues.

The surgeon utilizes surgical tools to obtain appropriate bony cuts to the skeletal system and alignment of the implanted device to the bone. The surgical tools are often mechanical devices used to achieve gross alignment of the skeletal system prior to or during an implant surgery. In a non-limiting example, mechanical alignment aids are commonly used to align the femur, tibia, and ankle optimally. The mechanical alignment aids are not integrated, take time to deploy, and have limited accuracy.

In at least one exemplary embodiment, a single system comprising one or more sensors is used intra-operatively, to define implant positioning, achieve appropriate implant orientation, and limb alignment. In particular, the system combines the ability to provide position information and measure one or more other parameters (e.g., load, blood flow, distance, etc.) that provides quantitative data to a surgeon that allows an implant to be adjusted within predetermined values or ranges based on the measured data and a database of other similar procedures. The system is designed broadly for use on the skeletal system including but not limited to the spinal column, knee, hip, ankle, shoulder, wrist, articulating, and non-articulating structures. For example, the sensors will enable the surgeon to measure joint loading while utilizing soft tissue tensioning to adjust balance and maximize stability of an implanted joint. Similarly, measured data in conjunction with positioning can be collected before and during surgery to aid the surgeon in ensuring that the implanted device has an equivalent geometry and range of motion.

It is noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data on each installation as well as generating post-operative and long-term measured data gives significant insight on the operation of a device under widely varying conditions. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device. In a non-limiting example, the system disclosed herein can be used by surgeons to measure the roughed-in implant device (or trial) and then make measurements that are used to dictate further bony cuts and alignments to fine tune the implanted device to meet the optimal settings. Furthermore, one or more sensors can be implanted to monitor the joint post-operatively and long term. The one or more sensors can monitor wear or other parameter that indicates failure or degradation of the orthopedic device. Thus, the one or more sensors can indicate a problem or suggest an optimal time to replace components of the orthopedic device such that only a minimally invasive procedure is required, thereby saving cost and stress on the patient. A further benefit of the system is the use of the measured data to improve materials and orthopedic implant designs based on measured parameters such as alignment, loading, balance, wear, temperature, and position.

Figure 34:
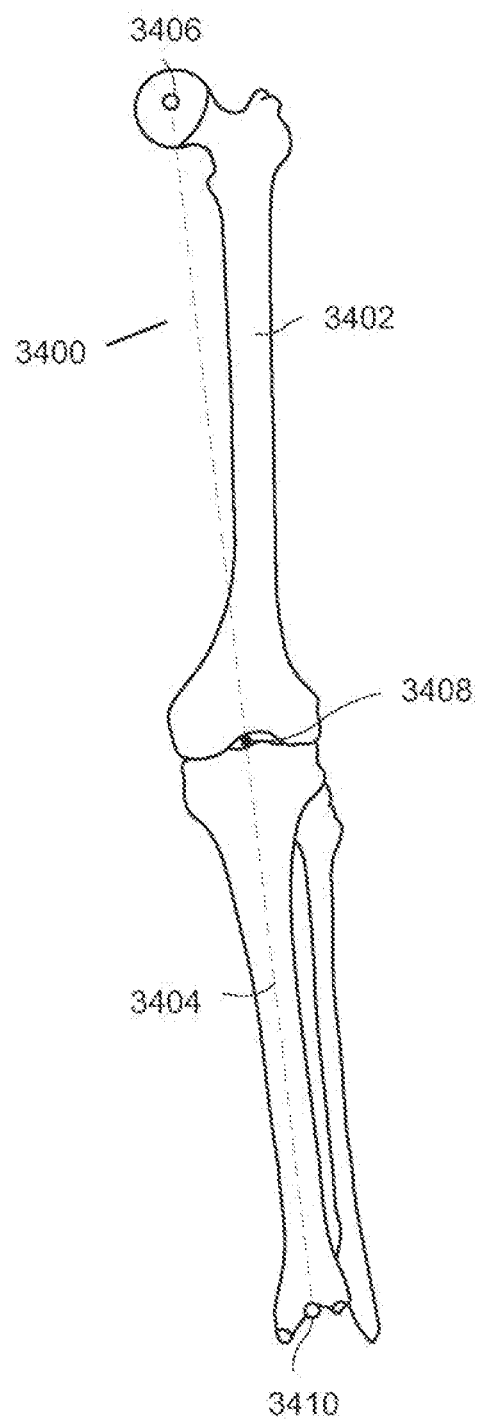
FIG. 34 is a diagrammatic, front elevational view of leg bones in extension and a mechanical axis of the leg according to the invention.

FIG. 34 is an illustration of a mechanical axis 3400 of a leg in accordance with an exemplary embodiment. The lower leg comprises a femur 3402 and a tibia 3404. Mechanical axis 3400 is typically defined with the leg in extension. The mechanical axis 3400 of the lower leg corresponds to a straight line drawn from a center of the femoral head 3406, through the medial tibial spine 3408, and through a center of an ankle 3410. In an optimal mechanical alignment, mechanical axis 3400 will pass through the anatomical center of the knee in all three dimensions. This is useful as it can define an alignment in every plane of the knee.

FIG. 35 is an illustration of a plurality of sensors placed on a lower leg in accordance with an exemplary embodiment. In at least one exemplary embodiment, the sensors are a component of a system that identifies position, relational positioning and measures parameters of the knee to aid in fitting of an orthopedic device. In a non-limiting example, some of sensors can be inserted in bone of the lower leg. For example, the sensors can be placed in a housing that has external screw threads. In at least one exemplary embodiment, the sensors comprise a control circuit, circuitry for wired or wireless communication, and a power source (temporary or rechargeable). In a non-limiting example, a position sensor can include one or more micro electromechanical systems (MEMS) accelerometers for measuring spatial orientation and position in three dimensions. A measurement sensor can include a device for measuring a parameter such as a strain gauge for measuring load or temperature sensor. The sensors in a screw-type housing can then be easily attached in bone using tools common to an orthopedic surgeon. Alternatively, the sensors can be temporarily attached to the bone, an implant device, or a surgical tool so they can be removed or disposed of. The sensors can also be included in the orthopedic implant.

In a non-limiting example, the system comprises positional sensor arrays 3502, 3504, 3506, 3508, 3510, and 3512 attached to the skeletal system. The system measures the position of each bone in which a sensor is attached as well as the relational positioning/spatial orientation in three dimensions. In an accelerometer position sensor system, a reference position can be identified and used to determine the location of other points. Ultrasonic, infra-red, electromagnetic, and fiber optic sensors can be used as well. Sensor array 3502 is coupled to femur 3402. Sensor array 3504 is coupled to tibia 3404. Sensor arrays 3506 and 3508 are respectively coupled to the medial malleoulus and lateral malleoulus of the ankle. In at least one exemplary embodiment, sensor array 3506 and 3508 are formed in a sensor pad that can be attached to the ankle. The center of ankle 3410 is determined from sensor arrays 3506 and 3508. The center of the femoral head can be determined by pre-operative scans or identified prior to alignment using a technique such as ultrasonic definition. Alternatively, one or more identification points can be registered using electro-magnetic, ultrasonic or infra-red sensors, and used in an alignment procedure to align skeletal structure. Sensor arrays 3510 and 3512 are coupled to a patella 3514 to monitor the position of patella 3514 in relation to distal end of the femur and proximal end of the tibia 3404.

FIG. 36 is a lateral view illustrating the plurality of sensors placed on the lower leg in accordance with an exemplary embodiment. Sensor array 3502 provides position information of femur 3402. Sensor array 3504 provides position information of tibia 3404. Relational positioning information of femur 3402 to tibia 3404 can be indicated on a display screen of the system and used in real time during orthopedic implant surgery. In general, accurate relational positioning can be used to identify a mechanical axis, to initiate cuts in a predetermined position, to check that an installed device is aligned correctly, or to verify a range of motion. Similarly, sensor arrays 3510 and 3512 can provide relational positioning information of patella 3514 to femur 3402 and tibia 3404. Sensor arrays 3510 and 3512 can also include force-measuring sensors to determine the loading on patella 3514 such that patellar tracking and tension can be adjusted through soft tissue tensioning (and the adjustments measured and viewed). Although not shown, sensor arrays 3502, 3504, 3506, 3508, 3510, and 3512 are in communication with a processing unit that receives the positional and measurement information and displays the information in a format useful to a surgeon on a screen or display. It is noted that sensors disclosed herein can be temporarily attached. In a non-limiting example, a sensor array can be taped, glued, or pinned to a location internal or external to the body. This allows additional flexibility to the placement of the sensors. The sensors can then be removed for reuse or disposed of after measurements have been taken, thereby being out of the way for subsequent surgical steps if desired.

Figure 37A:
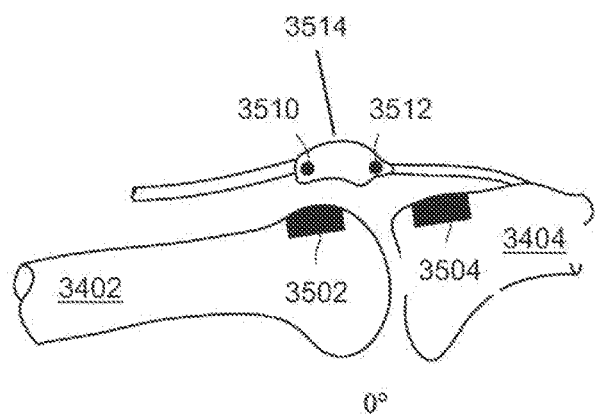
FIG. 37a is a diagrammatic, fragmentary lateral view of a lower leg with an exemplary embodiment of a plurality of sensor arrays in extension according to the invention.
Figure 37B:
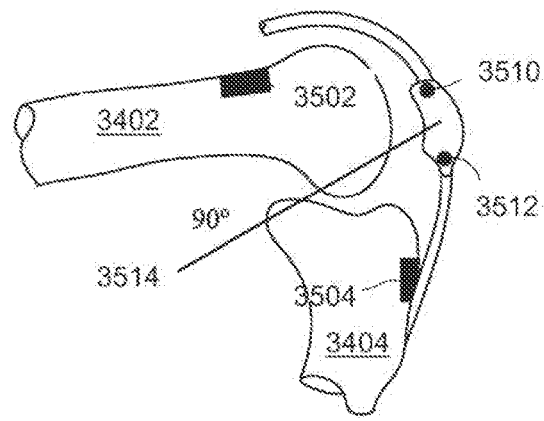
FIG. 37b is a diagrammatic, fragmentary lateral view of the lower leg of FIG. 37a in flexion.

FIGS. 37*a* and 37*b* are lateral views illustrating the lower leg with a plurality of sensor arrays in extension and flexion in accordance with an exemplary embodiment. In at least one exemplary embodiment, accelerometers in sensors 3502 and 3504 provide positional information and relational positioning, in at least one exemplary embodiment, accelerometers are in integrated circuit form such that a small form factor can be achieved. Furthermore, accelerometers can be provided that measure all three dimensions. The accelerometers can be integrated with the control circuit to further reduce sensor array footprint.

The lower leg can be positioned in extension by the surgeon. A screen displays the relative positioning such that femur 3402 and tibia 3404 are positioned corresponding to an actual position of the leg. For example, the surgeon places femur 3402 and tibia 3404 in extension such that they are both in the same plane. The display of the system indicates the position of femur 3402 in relation to tibia 3404 and shows an angle of zero degrees (0°) indicating that the leg is in extension.

Figure 38:
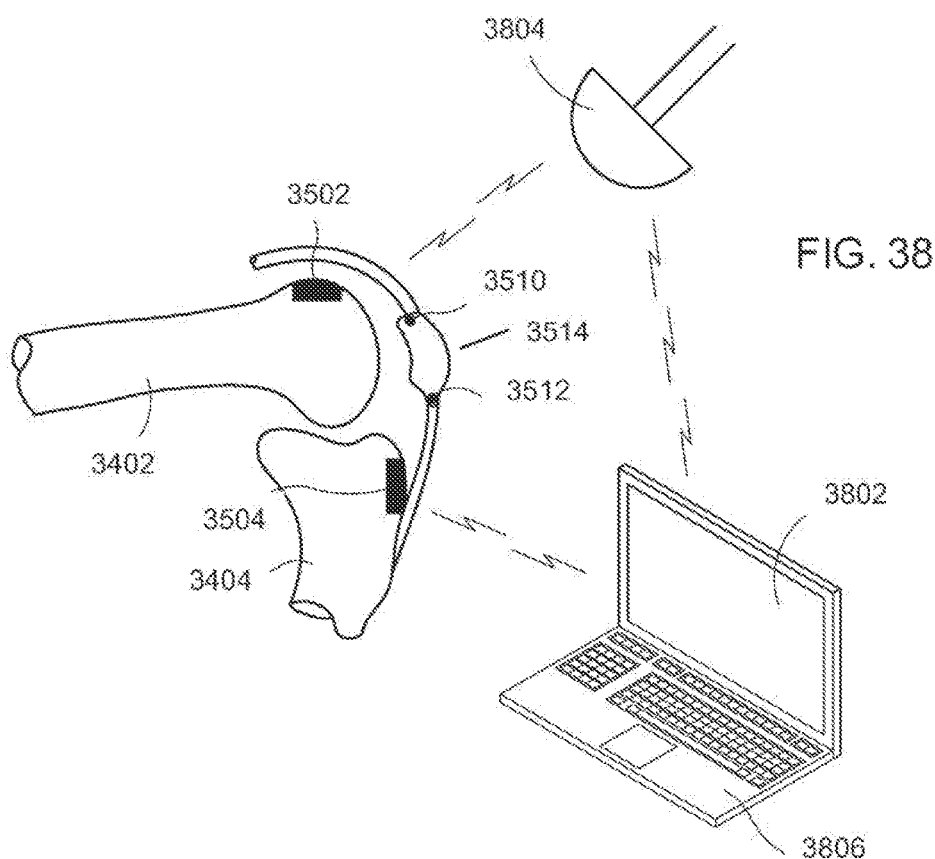
FIG. 38 is a diagrammatic, fragmentary lateral view of an exemplary embodiment of the plurality of sensor arrays in communication with a processing unit and a screen for providing information according to the invention.

A measurement of zero degrees describes femur 3402 and tibia 3404 in the same plane. The lower leg can be aligned to an optimal mechanical axis using position data from sensor arrays 3502, 3504, 3506, 3508 and a location of femoral head center 3406. Alternatively, femoral head center 3406 can be identified by rotating femur 3402 and using sensor arrays 3502 to track the motion. The tracked motion can be use to interpret the location of femoral center 3406. The knee center can be defined in the incision. Thus, the mechanical axis of the lower leg can then be defined very accurately using the sensors by aligning femoral head center 3406, the knee center, and the ankle center 3410. The surgeon then has the benefit of knowing proper alignment during the course of the implant surgery. Moreover, the positional relationship can be tracked throughout surgery. For example, in an orthopedic device implant, measurements can be taken over a range of motion to determine and ensure proper fit over the operational bounds of the device. As shown, sensor arrays 3502 and 3504 respectively coupled to femur 3402 and tibia 3404 can indicate the lower leg in flexion. More specifically, sensors 3502 and 3504 indicate that tibia 3404 is positioned ninety degrees (90°) from a position of femur 3402. Thus, the surgeon can make cuts and adjustments knowing the alignment and the positional relationships of bones of a skeletal structure are correct, FIG. 38 is a lateral view of the plurality of sensor arrays in communication with a processing unit 3806 and a screen 3802 for providing information in accordance with an exemplary embodiment. In at least one exemplary embodiment, sensor arrays 3502, 3504, 3506, 3508, 3510 and 3512 are in communication with a computer or computational device having processing unit 3806 for processing information from the sensors. For example, processing unit 3806 can be a microprocessor, a microcontroller, a digital signal processing chip, a mixed signal analog/digital chip, a logic circuit, a notebook computer, and/or a personal computer to name but a few. Screen 3802 is coupled to the computer for displaying sensor array measurement and position information. In a non-limiting example, screen 3802 and the computational device are outside of the surgical zone (or sterile box) in an operating room. In one exemplary embodiment, processing unit 3806 and screen 3802 comprises a notebook computer for reasons of portability, lower cost, and minimizing footprint in the operating room. The notebook computer incorporates a user interface for use by the surgeon or medical professionals that allow real-time interaction with the sensor position and measurement information. For example, as an aid to the surgeon, the portion of the skeletal structure having sensor arrays placed thereon can be displayed on screen 3802 to show alignment, position, and relational positioning in real-time as the surgical procedure progresses. Thus, the surgeon has a tool that combines both position and parameter measurement to aid in ensuring correct positioning of an implanted device and that the implanted device parametrics measure within reason and to allow adjustments to be made and measured, thereby allowing a surgeon to subsidize qualitative information with quantitative data.

In at least one exemplary embodiment, element 3804 facilitates communication between the sensor arrays and processing unit 3806. Element 3804 comprises receive and send circuitry and is in communication with processor unit 3806 and sensor arrays 3502, 3504, 3506, 3508, 3510, and 3512. Element 3804 can be placed in proximity to the sensors to ensure pick up of the signal. For example, component 3804 can be incorporated into a lighting system of the operating room where it has a direct and unblocked communication path. Alternatively, the element 3804 can be incorporated into the housing for the computational device or screen 3802 to provide the sensor information to the processor. Element 3804 can be directly connected to sensors 3502, 3504, 3506, 3508, 3510, and 3512 by wires or fiber optics, for example. Similarly, element 3804 can be connected to processing unit 3806 by wire or fiber-optics, for example. Element 3804 can also be wirelessly connected to sensors 3502, 3504, 3506, 3508, 3510, and 3512 and the processor using radio frequency, ultrasonic, infra-red, magnetic or other wireless communication methodology.

As mentioned previously, each sensor array is coupled to a control circuit. The control circuit includes circuitry to convert the data to a form that can be transmitted by wire or wirelessly. For example, the control circuit can have transmitter/receiver circuitry for transmitting data in a known format such as Bluetooth, UWB, or Zigbee. In one embodiment, position and measurement data is taken periodically or by command. The data can be stored in memory. The control circuit can be enabled by a received signal from processing unit 3806 to send the information stored in memory. Similarly, the control circuit can be enabled to take position and measurement data by processing unit 3806. This enables multiple sensor arrays to be enabled and an orderly process for collecting data, sending data, analyzing processing the information (using processing unit 3806), and displaying the data on screen 3802 for use by the surgeon or medical team during surgery.

Figure 39:
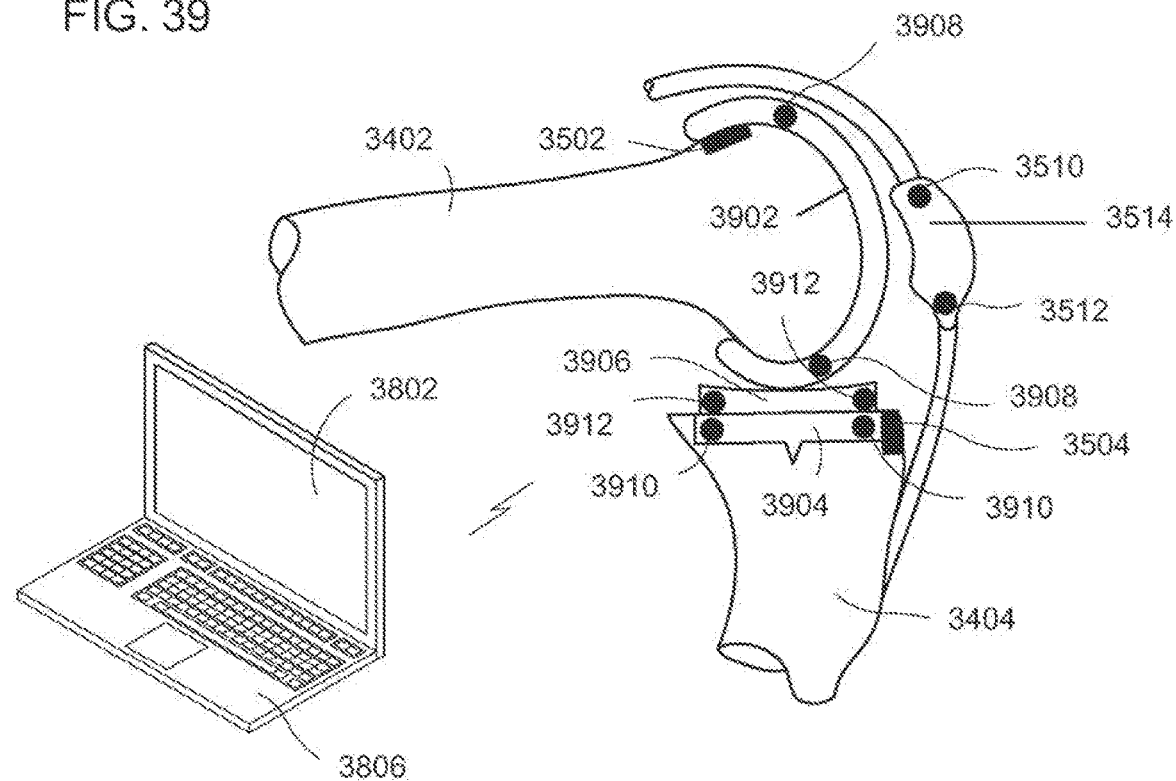
FIG. 39 is a diagrammatic, fragmentary lateral view of a knee and an exemplary embodiment of joint implant and a sensor system according to the invention.

FIG. 39 is a lateral view of the knee illustrating a knee with a joint implant and sensors in accordance with an exemplary embodiment. The knee is used as an example of the system for orthopedic implants to lower cost, reduce stress on the patient, have a small spatial footprint in the operating room, collect data, aid in tuning the device implant for optimal geometry, and reduce short term/long term post-operative rework. The system is adaptable for use in all areas of the skeletal system. More specifically, a single system is disclosed for orthopedic surgery, which can provide alignment, positioning, relational positioning, initial conditions, loading, and balance information over the entire range of motion. Integration into a single system greatly simplifies the procedure and ensures consistency of results because both qualitative (e.g., surgeon) and measured (quantitative) data can be used to assess each step of the procedure. Moreover, the data collected can be used to identify issues before they become problems for the patient and provide information for improving the orthopedic device.

There is a general trend to implement solutions that lower health care operating costs without compromising patient care. One benefit of the systems according to the invention is that they can be easily incorporated into orthopedic surgeries because of low cost. The single system does not require a significant capital expense. For example, the computational device that houses processing unit 3806 can be a laptop computer that can be purchased at low cost instead of a fully customized system. Software corresponding to this application is downloaded to and stored on the laptop computer. Element 3804 can also be coupled to the laptop computer either wired or wirelessly to support communication if needed. In at least one exemplary embodiment, the system is made as a disposable device. In other words, there is almost no capital expense required by the hospital or clinic to implement the system, thereby eliminating typical barriers to adopting new technology. Some of the system components are incorporated in orthopedic implant trials or temporarily attached to the skeletal system, these parts can be disposed of after measurements are made or prior to the final implant device installation. Alternatively, the sensors can be permanently incorporated into the skeletal structure and final implant device for post-operative monitoring and for long term device monitoring.

In a non-limiting example, the implanted device is shown with a trial insert used to measure and tune the knee joint prior to a final insert being installed. The single system comprises any of the sensors or sensor arrays disclosed herein. The single system further comprises a femoral implant 3902, a tibial implant 3904, and a trial insert 3906. Trial insert 3906 measures a parameter such as load over a range of motion. In at least one exemplary embodiment, the knee joint is exposed by incision. Alignment of the mechanical axis of the lower leg is achieved as disclosed above with the leg in extension such that the femoral head center, medial tibial spine, and ankle center are aligned in a straight line using the single system to aid the surgeon. Bony cuts are made utilizing the alignment whereby the distal end of femur 3402 and the proximal end of tibia 3404 are shaped for receiving orthopedic joint implants. Jigs and other orthopedic devices can be used to shape and aid in the bony cuts. The sensors of the invention can be attached to the cutting jigs or devices to aid the surgeon in optimizing the depth and angles of their cuts.

In a non-limiting example, a rectangle is formed by the bony cuts. The imaginary rectangle is formed between the cut distal end of femur 3402 and the cut proximal end of tibia 3404 in extension and in conjunction with the mechanical axis of the lower leg. A predetermined width of the rectangle is the spacing between the planar surface cuts on femur 3402 and tibia 3404. The predetermined width corresponds to the thickness of the combined orthopedic implant device comprising femoral implant 3902, trial insert 3906, and tibial implant 3904. Trial insert 3906 is inserted between the installed femoral implant 3902 and tibial implant 3904. Trial insert 3906 can have a surface comprising the same or similar material as a final insert.

In at least one exemplary embodiment, trial insert 3906 comprises load, accelerometer, and other types of sensors 3912. The sensors 3912 are in communication with processing unit 3806. Sensors can be placed in femoral implant 3902, trial insert 3906, and tibial implant 3904 that work in conjunction with the sensors described herein to define limb alignment, implant-to-implant alignment, and joint kinematics. In general, the sensors of femoral implant 3902, trial insert 3906, and tibial implant 3904 can measure parameters such as weight, strain, pressure, wear, position, acceleration, temperature, vibration, density, and distance. Trial insert 3906 is used to measure the load on either condyle surface of femoral implant 3902 while in extension. In a non-limiting example, the screen of the system (e.g., display 3802) can show the location of the point of contact for both condyle surfaces on trial insert 3906 and the load.

Trial insert 3906 can indicate that the loading measurement on both condyles is either high, within an acceptable predetermined range, or low. A loading that measures above a predetermined specification can be adjusted using a thinner final insert. Conversely, a loading that measures below a predetermined specification can be adjusted using a thicker final insert. The system can provide an appropriate solution from a look up table (changes in thickness versus measurement to get within a predetermined range). Alternatively, trial insert 3906 can be removed and another trial insert of a different thickness can be used to take a measurement such that a loading in the predetermined range is measured. The surgeon can also make a soft tissue adjustment in the case where the tension is too high but close to the predetermined range. As mentioned previously, the system is in communication with processing unit 3806 to record measurements during the surgical procedure.

Balance is a comparison of the load measurement of each condyle surface. Balance correction is performed when the measurements exceed a predetermined difference value. Soft tissue balancing is achieved by loosening ligaments on the side that measures a higher loading. The system provides the benefit of allowing the surgeon to read the reduced loading on screen 3802 of the system with each soft tissue release until the difference in loading between condyles is within the predetermined difference value. Another factor is that the difference in loading can be due to surface preparation of the bony cuts on either femoral implant 3902 or tibial implant 3904. The surgeon has the option of removing bone on either surface underlying the implant to reduce the loading difference. In a further exemplary embodiment, trial insert 3906 provides position data indicating where each condyle contacts a surface of trial insert 3906. Similar to above, the surgeon has the option of altering the surface of the distal end of femur 3402 or the proximal end of tibia 3404 to move the contact regions in conjunction with the mechanical axis.

As shown in FIG. 39, the lower leg is in flexion with tibia 3404 at a right angle to femur 3402. In general, one or more bony cuts to the distal end of femur 3402 are made. In particular, a prepared surface at the distal end of femur 3402 is parallel to the prepared surface of tibia 3404 in this position. Similar to that described above, an imaginary rectangle is formed by the parallel surfaces of femur 3402 and tibia 3404 in the ninety-degree flexion position. A predetermined width of the imaginary rectangle is the spacing between the planar surface cuts on femur 3402 and tibia 3404 in the flexion position (ninety degrees). The predetermined width corresponds to the thickness of the combined orthopedic implant device comprising femoral implant 3902, trial insert 3906, and tibial implant 3904. Ideally, the measured width is similar or equal to the width of the imaginary rectangle in extension. Load measurements are made with the leg in flexion. Adjustments to the load value and the balance between condyles can be made by soft tissue release and femoral cuts/implant rotation. Once adjusted, tibia 3404 can be moved in relation to femur 3402 over the range of motion. The loading can be monitored on the screen over the range of motion to show that the absolute loading on the knee is within a predetermined load range and that the difference in loading between the two condyles is within a predetermined differential value. Should an out-of-range-value condition occur, the surgeon can view the position where it occurs on screen 3802 of the system and can take steps to bring the condition within specifications. It is noted that, presently, a surgeon does not have the capability of performing such corrections. Finally, as the leg is rotated through the range of motion, a plot of the movement of the contact region of either condyle can be displayed on the screen 3802. The contact region should be within a predetermined area. Movement outside the predetermined area can indicate a misalignment or rotation issue, which the surgeon can correct at this time. The trial insert is removed if the surgeon is satisfied by the measured data. Femoral implant 3902, a final insert, and tibial implant 3904 are then permanently attached to the knee. In at least one exemplary embodiment, the final insert can have sensors for post-operative monitoring and long-term monitoring of the implanted device.

Sensor arrays 3510 and 3512 on patella 3514 can be used to track position and measure a parameter (such as load). Sensor arrays 3510 and 3512 work with sensor arrays 3908 in femoral implant 3902. Moving the leg through a range of motion will track patella 3514 in relation to femoral implant 3902. The system will show patellar movement and loading on the screen. The surgeon can then use soft tissue adjustments and/or a change in the implant rotation positioning to ensure the patella tracks correctly (alignment) and that the loading stays within a predetermined range (over the range of motion). With each correction, the surgeon can view on the screen how the correction affected patellar tracking and loading until satisfactory results are achieved. It is noted that, presently, surgeons do not have this kind of feedback to make adjustments.

Figure 40:
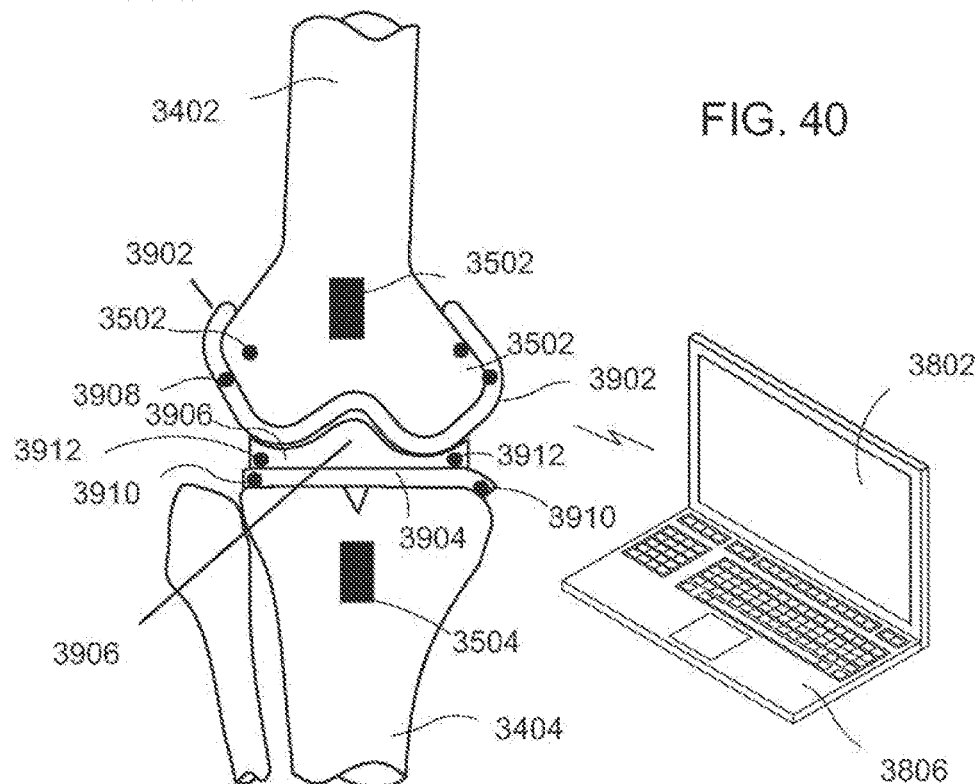
FIG. 40 is a diagrammatic, fragmentary anteroposterior view of a knee and an exemplary embodiment of a joint implant and a sensor system with sensor arrays according to the invention.

FIG. 40 is an anteroposterior view of a knee and sensor arrays in accordance with an exemplary embodiment. The sensor arrays are incorporated for long term monitoring. Femur 3402 is shown having sensor arrays 3502. Femoral implant 3902 is coupled to the distal end of femur 3402. Femoral implant 3902 includes sensors 3908. Tibia 3404 is shown having sensor arrays 3504. Tibial implant 3904 is coupled to the proximal end of tibia 3404. Tibial implant 3904 includes sensor array 3910. An insert 3906 is coupled between tibial implant 3904 and femoral implant 3902. Two condyles of femoral implant 3902 ride on a bearing surface of insert 3906. Sensor arrays 3912 of insert 3906 underlying the bearing surface can be used to take measurements as disclosed hereinabove. The sensors of the system work in conjunction with processing unit 3806 and communication circuitry to provide data that can be used to determine the working status of the implant and to minimize short-term and long-term problems after surgery. In at least one exemplary embodiment, the patient can return for outpatient review of the implant. The sensor arrays of the system can be placed in communication with processing unit 3806 or another system loaded with enabling software. An analysis of the status of the orthopedic device and patient health can be provided and displayed on screen 3802.

Sensors according to the invention are used in multiple orthopedic applications, including intra-operative joint implant alignment. Sensors and monitoring devices/systems that can be used include any of those well known in the art, such as those described in the Nexense patents and incorporated herein by reference. Computer assisted surgery is also commonplace.

Presently, the use of pins in the femur and tibia, allow arrays to be attached to the bones. Such attachment helps in spatial orientation of the knee/hip joint during the operation. These arrays are recognized by infrared optics or by electromagnetic devices (see, e.g., FIGS. 48 and 49) to replay the information into a recognized software system that allows the surgeon to visualize the joint in a three-dimensional manner while overlaying the implant of choice on the bones. Problems encountered with the application of such pins are many:

the need to penetrate bones outside the field of surgery;
  post-operative pain that might require peripheral nerve blocks and neuro-modulation and drainage from the pin sites;
  the possibility of pin loosening during the surgery as well as blocking the arrays and infra-red light;
  the pins require the surgeons to change the present positioning during the procedure, which can be difficult; and
  the electromagnetic field can be affected by various metals and instruments that are used in the surgery.

The time associated with inserting the pins, locking the arrays, and registering the joint topography contributes to a significantly long procedure duration. There is still a need to individually touch multiple points on the femur and tibia to allow the computer to visualize the topography of the knee. The time for transmission of information from the sensors to the receiver also causes a potential delay. Therefore, it would be desirable to reduce or eliminate each of these problems.

Methods according to the invention include implanting the sensors in the field of surgery, using the sensors during surgery, and using the implanted sensors post-operatively to evaluate various desired parameters.

Moving now to FIGS. 46 and 47, these figures depict one exemplary embodiment of a handle 170 that can be releasably connected to an implantable sensor body 5. In this embodiment, the handle has an exterior thread that screws into an interior correspondingly threaded bore of the body 5.

FIG. 50 illustrates embedded sensors 6 in the femur and the tibia, and FIG. 51 illustrates sensors 6 in the patella. The ligaments shown include the medial collateral ligament, the lateral collateral ligament, the anterior cruciate ligament, and the posterior cruciate ligament. The sensors 6 are implanted prior to surgery percutaneously and/or arthroscopically or intra-operatively through open surgery. FIG. 52 depicts a ligament or tendon. FIG. 53 depicts a sensor clamp with a compressive and release handle, FIG. 54 depicts the partial deployment of the sensor, and FIG. 55 reveals the deployed sensor in the ligament. As shown in the steps depicted by FIGS. 52 to 55, the sensors can be embedded into the ligaments (FIG. 52 illustrates an exemplary ligament) by providing a sensor clamp (FIG. 53) that is placed around the ligament (FIG. 54) and secured thereto (FIG. 55). The sensor clamp (FIG. 53) above has sensors, a handle, and applies a compressive force to the muscular-skeletal system. The sensors can also be embedded into bone as shown later in FIG. 71, for example. Standard radiograph techniques can be used to guide deployment angle and depth.

The exemplary embodiments of sensors and sensor systems described herein have been associated with the dynamic adjustment of trial implants to improve the implant surgery in a way that maximizes success when the final implant is installed. To assist with the dynamic adjustment of the implants (for example, femoral implant 3902, tibial implant 3904, and insert 3906) inter-operatively, a distractor tool can be utilized. This distractor tool can be equipped with any of the sensors disclosed herein.

By way of the exemplary distractor device contemplated hereinbelow, the surgeon receives measured data during surgery, and post-operatively on the factors listed above. As one example, accurate measurements can be made during orthopedic surgery to determine if bones or an implant are optimally balanced and aligned. This can reduce operating time and surgical stress for both the surgeon and patient. The data generated by direct measurement can be further processed to assess long-term integrity based on maintaining surgical parameters within predetermined ranges. The measured data in conjunction with patient information can lead to improved design and materials.

Figure 56:
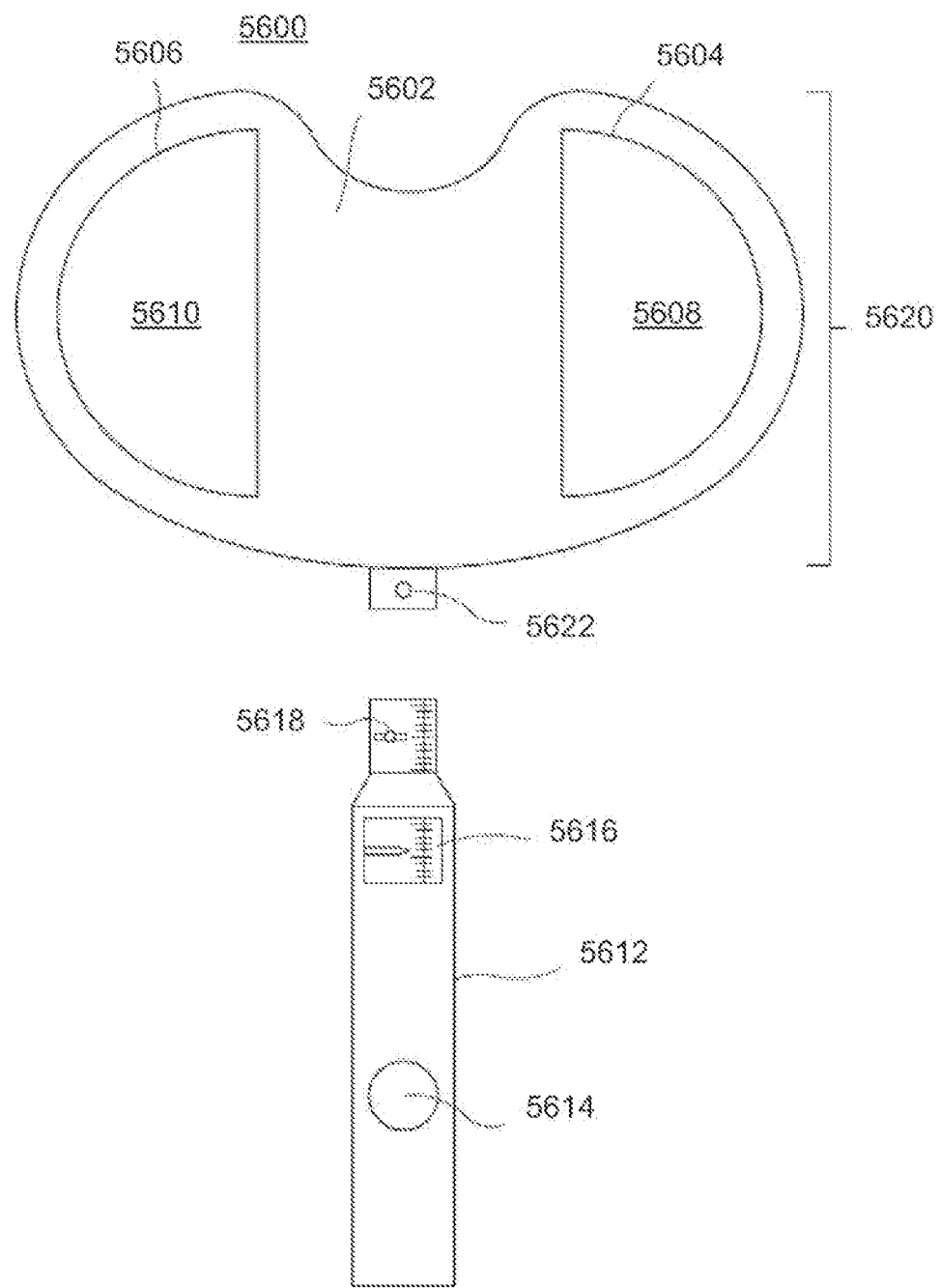
FIG. 56 is a top plan view of an exemplary embodiment of a dynamic distractor according to the invention.

FIG. 56 is a top view of a dynamic distractor 5600 in accordance with an exemplary embodiment. Dynamic distractor 5600 is also known as a dynamic spacer block. Dynamic distractor 5600 is a sensored device that is used during surgery of a muscular-skeletal system. Dynamic distractor 5600 can be used in conjunction with other tools common to orthopedic surgery as will be disclosed in more detail hereinbelow. This distractor 5600 for example can be used as a ligament tensioning device and/or a dynamic insert trial to mimic variable thicknesses. In at least one exemplary embodiment, the system is used during orthopedic joint surgery and, more specifically, during implantation of an artificial joint. The system uses one or more sensors intra-operatively to define implant loading and positioning and to achieve appropriate implant orientation, balance, and limb alignment. In particular, dynamic distractor combines the ability to align and measure one or more other parameters (e.g., load, blood flow, distance, etc.) that provides quantitative data to a surgeon, allowing the orthopedic surgery to be measured and adjusted within predetermined values or ranges based on the measured data and a database of other similar procedures. The system is designed broadly for use on the skeletal system including, but not limited to, the spinal column, knee, hip, ankle, shoulder, wrist, articulating structures, and non-articulating structures.

Dynamic distractor 5600 comprises an upper support structure 5702 and a lower support structure 5704. An active or dynamic spacer portion 5620 of dynamic spacer block comprises the upper and lower support structures 5702, 5704. A lift mechanism 5802 (see, e.g, FIG. 58) couples to an interior surface of upper support structure 5702 and an interior surface of the lower support structure 5704. A handle 5612 couples to the lift mechanism 5802. In one embodiment, handle 5612 is operatively coupled to the lift mechanism 5802 to change a gap of the spacer block. Handle 5612 can also be used to guide dynamic distractor 5600 between regions of the muscular-skeletal system. In general, the upper support structure has a superior surface 5602 that interfaces with a surface of the muscular-skeletal system. Similarly, the lower support structure has an inferior surface 5706 that interfaces with a surface of the muscular-skeletal system.

In one exemplary embodiment, handle 5612 can be rotated to adjust the lift mechanism 5802 to increase or decrease a gap between the superior and inferior surfaces of the active spacer block, thereby modifying the height or thickness of dynamic distractor 5600. In a non-limiting example to illustrate a disposable aspect of the invention, superior surface 5602, the inferior surface 5706, or both surfaces include at least one cavity or recess 5604, 5606 for housing at least one sensor module 5608, 5610. The sensor module 5608, 5610 includes at least one sensor for measuring a parameter of the muscular-skeletal system. For example, the sensor can measure a force or pressure. As will be disclosed hereinbelow, the sensor can be disabled so it cannot be reused and disposed of after the procedure has been performed. In a further example, dynamic distractor 5600 can be placed between two or more bone surfaces such that the superior surface 5602 and the inferior surface 5706 contact surfaces of the muscular-skeletal system related to a joint. In one embodiment, the sensor is coupled to a surface of the muscular-skeletal system for measuring a parameter when positioned between surfaces. Handle 5612 can be rotated to different gap heights allowing pressure measurements at the different gap heights to generate data of gap versus pressure.

Handle 5612 further includes an opening 5614, a decoupling mechanism 5618, and a display 5616. Opening 5614 is used to receive additional components of the system that will be described in more detail hereinbelow. Decoupling mechanism 5618 allows removal of the handle during parts of a surgery to allow access to the muscular-skeletal system. Decoupling mechanism 5618 couples to a locking mechanism that locks handle 5612 to a shaft of the lift mechanism 5802. Decoupling mechanism 5618 releases the locking mechanism, thereby allowing handle 5612 to be removed from dynamic distractor 5600. In one exemplary embodiment, the locking mechanism is a pin or ball that fits into a corresponding feature 5622 on the shaft of the lift mechanism 5802. Decoupling mechanism 5618 releases or frees the pin or ball from feature 5622, thereby allowing removal of handle 5612. Alternatively, decoupling mechanism 5618 can be a hinge or joint that allows handle 5612 to move in a direction that allows greater access by the surgeon to an area where the spacer block portion of dynamic distractor 5600 has been placed. The display 5616 on handle 5612 can provide a readout of the gap between the superior surface 5602 and the inferior surface as handle 5612 is rotated to adjust spacing.

In a non-limiting example, dynamic distractor 5600 is adapted for use in artificial knee implant surgery. It should be noted that dynamic distractor 5600 can be similarly adapted for other orthopedic surgery where both distraction and parameter measurement is beneficial. A knee implant is used merely as an example to illustrate how dynamic distractor 5600 can be used in a surgical environment. In at least one exemplary embodiment, the superior surface 5602 of dynamic distractor 5600 includes a first recess or cavity 5604 and a second recess or cavity 5606. In one embodiment, sensor 5608 and 5610 are pre-sterilized in one or more packages. The packaging is opened prior to or during surgery within the surgical zone to maintain sterility. Sensors 5608 and 5610 are shown respectively placed in cavities 5604 and 5606 for measuring a parameter that aids in the surgical procedure. In the knee example, sensors 5608 and 5610 include pressure sensors such as strain gauges, mechanical-electrical-machined (MEMS) sensors, diaphragm structures, mechanical sensors, or other pressure measuring devices. In one exemplary embodiment, a major exposed surface of sensors 5608 and 5610 is in contact with the muscular-skeletal system after insertion. Alternatively, one or more layers of material or portions of the muscular-skeletal system can be disposed between sensors 5608 and 5610 such that the parameter can be measured or transferred through the intervening layers. A force or pressure applied to the exposed surfaces is measured by sensors 5608 and 5610 while the gap of the dynamic distractor is adjusted. Alternatively, the lift mechanism 5802 in conjunction with sensors 5608 and 5610 can be set to a predetermined pressure. The lift mechanism gap increases until the predetermine pressure is reached. From this, a gap height or thickness of dynamic distractor 5600 is identified to achieve the predetermined pressure.

In at least one exemplary embodiment, sensors 5608 and 5610 are disposable devices. After measurements have been taken, sensors 5608 and 5610 can be removed and disposed of in an appropriate manner. Alternatively, the sensors 5608 and 5610 can be a permanent or integral part of the superior surface of dynamic distractor 5600. The housing can be designed to be reused and to withstand a sterilization process after each use. The main body of dynamic distractor 5600 as well as sensors 5608 and 5610 are cleaned and sterilized before each surgical usage.

Dynamic distractor 5600 in a zero gap (or closed condition) is less than 8 millimeters in total thickness for the knee application and can expand using the lift mechanism 5802 to greater than 25 millimeters. This range is sufficient for the majority of artificial knee implant surgeries being performed presently. The spacer portion 5620 of dynamic distractor 5600 contains the superior and inferior surfaces 5602, 5706 that articulate to at least two bone ends of the muscular-skeletal system. In the knee example, the dynamic distractor 5600 is placed between the distal end of the femur and the proximal end of the tibia. As mentioned previously, sensors 5608 and 5610 are in a housing. In one embodiment, the housing includes sensor elements to define the loads on the medial and lateral compartments. The sensored elements can comprise load displacement sensors, accelerometers, GPS locators, telemetry, power management circuitry, a power source and an ASIC, to name a few.

As disclosed above, the spacer portion 5620 of dynamic distractor 5600 is placed between the femur and tibia in extension. The dynamic distractor 5600 is configured with no gap (i.e., minimum height or thickness) or having a gap that can be inserted and removed without tissue damage. In general, the gap can be increased by rotating handle 5612 after insertion, so that the inferior surface of dynamic distractor 5600 contacts a prepared surface of a proximal end of a tibia and the superior surface contacts the prepared distal end of the femur. In general, the femoral and tibial cuts in extension are made parallel to one another. Similarly, the femoral cut in flexion is made parallel to the prepared end of the tibia. The gap is measured to determine a combined thickness of the implants with the leg in extension. The prepared ends of the tibia and femur can be checked for alignment with the mechanical axis at this time as will be disclosed in detail below.

Typically, the surgeon selects the artificial components based on the cross-sectional size of the prepared bones. The variable component of the implant surgery is the final insert. The final insert has one or more bearing surfaces for interfacing with a femoral implant. In one embodiment, the measured gap height created by dynamic distractor 5600 is used to define an insert thickness or height. The thickness of a final insert can change during surgery as further bone cuts or tissue tensioning occurs. Dynamic distractor 5600 can be used during surgery to measure loading and gap height after each bone modification or after an orthopedic component has been implanted.

Dynamic distractor 5600 can also be used to obtain an optimal balance. Balance is related to the measured loading between two or more areas. The measured values can than be adjusted to a predetermined relationship and within a predetermined value range. In the knee example, balance is associated with the differential pressure applied by each condyle on the bearing surfaces of the implant. Ideally, a predetermined surface area of the femoral implant condyle contacts the bearing surface to distribute the load and minimize wear. In a non-limiting example, a predetermined relationship between measured values by sensors 5608 and 5610 of dynamic distractor 5600 is maintained after implantation of the artificial components. In one embodiment, the balance of the knee is maintained by having the measured load in each compartment approximately equal. A method to balance the loading of the compartments is through ligament release on the side having the larger loading value. Ligament release reduces loading primarily on the adjacent compartment. The loading can be read off a display on dynamic distractor 5600, allowing the surgeon to view the change in loading and the differential value with each release. The lift mechanism 5802 provides sufficient room between the superior and inferior surfaces of dynamic distractor 5600 for a surgeon to perform a release procedure without removing the device. A next greater thickness of an insert can be selected should the absolute loading value on each condyle fall outside the predetermined range due to the soft tissue release. Handle 5612 can be rotated to increase the gap height to the next larger insert value to ensure the measured loading falls within the predetermined range and the differential loading falls within a predetermined range (after the soft tissue release).

The loading and balance of an implanted joint should be maintained within the predetermined values throughout the range of motion. In at least one exemplary embodiment, measurements are taken when the tibia is at a ninety-degree angle to the femur. Handle 5612 is used to position the spacer block portion of distractor 5600 between the femur and the tibia. The inferior surface 5706 of dynamic distractor 5600 is in contact with the prepared surface of the tibia. In one embodiment, the superior surface 5602 is in contact with the remaining portion of the condyles of the femur. Thus, the condyle surfaces of the femur are in contact with sensors 5608 and 5610 on the superior surface of dynamic distractor 5600. In this example, a gap height of dynamic distractor 5600 is reduced to accommodate the condyles that remain on the distal end of the femur in flexion. The gap height of dynamic distractor 5600 can then be adjusted to a height corresponding to the gap height in extension less the thickness of the femoral implant, whereby the leg in flexion is similar to the leg in extension. This can be achieved by specific ligament releases in flexion and/or rotation of the femoral implant to achieve a parallel levels between the posterior femoral condyles and proximal tibia. A femoral sizer can be attached to the distractor to allow sizing of the femur, coupled with rotation of the femur. This allows dynamic rotation to obtain equally balanced flexion compartments.

The loading on sensors 5608 and 5610 with the leg in flexion can be measured. The measurement is of value if the condyles are not damaged or degraded. In one exemplary embodiment, soft tissue release is used to adjust the balance between compartments with the leg in flexion. The soft tissue release can also be performed later in the procedure after the femoral implant has been implanted. Similar to the leg in extension, soft tissue release is performed to reduce the tension on the side having the higher compartment reading with dynamic distractor 5600 in place. After soft tissue release, the readings in each compartment should be within a predetermined differential range. The distal end of the femur can then be prepared for receiving the femoral implant, which removes the remaining portion of the condyles. As disclosed, the surface of the femur is prepared to be parallel to the prepared tibial surface in flexion.

In a non-limiting example, the femoral implant component can be temporarily attached to the distal end of the femur. Measurements can be taken throughout the entire three-dimensional range of motion using dynamic distractor 5600 to ensure that the implanted knee operates similarly in all positions. A gap provided by dynamic distractor 5600 would be adjusted to a combined thickness of the final insert thickness and the tibial implant thickness. Dynamic distractor 5600 can incrementally increase or decrease the gap to allow the surgeon to determine how different insert thicknesses affect load and balance measurements. In one exemplary embodiment, accelerometers are used to provide position and relational positioning information. The data can be stored in memory for later use or displayed to provide instant feedback to the surgeon on the implant status. Further adjustments to load and balance can be made with dynamic distractor in place if desired over different positions within the range of motion. Although one implant sequence is disclosed, it is well known that surgeons have different approaches, methodologies, and procedure sequences. The use of dynamic distractor 5600 would be applied similarly to distract and measure in different relational positions with the device in place. Furthermore, the device can be used or modified for use on different parts of the anatomy of the muscular-skeletal system.

Figure 57:
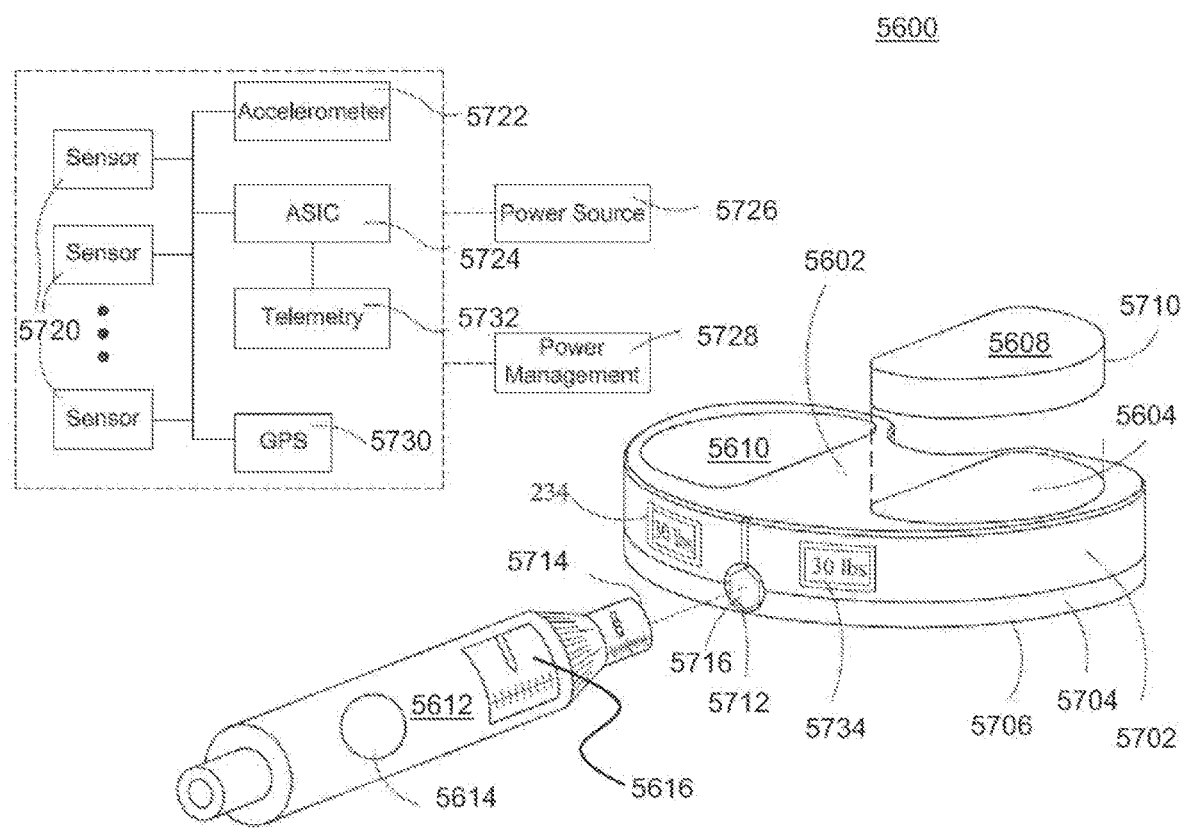
FIG. 57 is a perspective view of the dynamic distractor of FIG. 56 in a minimum height state.

FIG. 57 shows the dynamic distractor 5600 having a minimum height in accordance with an exemplary embodiment. Dynamic distractor comprises an upper support structure 5702 having superior surface 5602 and a lower support structure 5704 having an inferior surface 5706. In the example, upper support structure 5702, the lift mechanism 5802, and lower support structure 5704 supports loading typical for a joint of the muscular-skeletal system. Upper and lower support structures 5702 and 5704 comprise rigid and load bearing materials such as metals, composite materials, and plastics that will not flex under loading. In one exemplary embodiment, stainless steel is used in the manufacture of the lift mechanism 5802 and upper and lower support structures 5702 and 5704.

Dynamic distractor 5600 is used to distract surfaces of the muscular-skeletal system. Dynamic distractor 5600 can be used in an invasive procedure such as orthopedic surgery. In the non-limiting example, dynamic distractor 5600 can distract surfaces of the muscular-skeletal system in a range of approximately 8 millimeters to approximately 25 millimeters. The support surfaces of dynamic distractor 5600 do not flex under loading of the muscular-skeletal system. In one exemplary embodiment, dynamic distractor 5600 has a minimum height or thickness between support surfaces of less than 8 millimeters. In at least one application, a space between support structures 5702 and 5704 is provided when dynamic distractor 5600 is opened to a height greater than the minimum height. The space between support structures 5702 and 5704 when opened allows a surgeon to perform soft tissue release with the device in place.

One cavity 5604 is illustrated in superior surface 5602 of upper support structure 5702. The cavity 5604 is shaped similarly to a housing 5710 of sensor 5608. Housing 5710 is placed within cavity 5604 for measuring a compressive force applied across superior surface 5602 and inferior surface 5706. In the knee example, a condyle (implanted or natural) couples to an exposed surface of sensor 5608. A pressure or force applied to sensor 5608 is measured and displayed by dynamic distractor 5600. Sensor 5610 is shown placed in its corresponding cavity 5606 in superior surface 5602. In one embodiment, the exposed surfaces of sensors 5608 and 5610 are approximately planar to the superior surface 5602. The exposed surface of sensor 5608 and 5610 can be flat or contoured. Sensors 5608 and 5610 can be removed from upper support structure 5702 and disposed after the surgery has been performed. In one exemplary removal embodiment, a push rod is exposed in the interior surface of upper support structure 5702 that, when pressed, can apply a force to housing 5710 that removes sensor 5608 from cavity 5604.

In one exemplary embodiment, housing 5710 is formed of a plastic material. The sensor and electronic circuitry is fitted in housing 5710. The electronic circuitry comprises any combination of one or more sensors 5720, one or more accelerometers 5722, an ASIC integrated circuit 5724, a power source 5726, power management circuitry 5728. GIPS circuitry 5730, and telemetry 5732. The power source 5726 can be a battery or other temporary power source that is coupled to the electronic circuitry prior to surgery. The power source 5726 has sufficient power to enable the circuitry for a period of time that will cover the vast majority of surgeries. The power management circuitry 5728 works in conjunction with the power source to maximize the life of the power source by disabling system components when they are not being used. In general, an ASIC circuit controls and coordinates when sensing occurs, can store data to memory (e.g., non-volatile), and can transmit data in real time or collect and send data at a more appropriate time to a remote system for further processing. The ASIC includes multiple ports that couple to one or more sensors 5720. The ASIC couples to at least one of the following: at least one sensor 5720; at least one accelerometer 5722; a GPS 5730; and telemetry circuitry 5732. The ASIC 5724 can include the integration of telemetry circuitry 5732, power management circuitry 5728. GPS circuitry 5730, memory, and sensors 5720 to further reduce the form factor of the sensing system. In the example, the at least one sensor 5720 is a pressure sensor that is coupled to the exposed surface of the housing. The pressure sensor converts the pressure to an electrical signal that is received by the ASIC. The at least one accelerometer 5722 and GPS 5730 provide positioning information at the time of sensing. Telemetry circuitry 5732 communicates through a wired or wireless path. In one exemplary embodiment, the data is sent to a remote processing unit that can process and display information for use by the surgeon or medical staff. One or more displays 5734 can be placed on dynamic distractor 5600 to simplify viewing of any measurement by sensors 5608 and 5610 (e.g., pressure or force) thereby allowing real time loading and balance differential to be seen at a glance. The information can be stored in memory on the sensor or transmitted to a database for long-term storage and processing.

In a zero gap or minimum height condition, the lift mechanism 5802 is enclosed within the device. An opening 5712 exposes a lift control mechanism 5716 (e.g., a threaded rod) that is a component of the lift mechanism 5802. The exposed end portion of lift control mechanism 5716 is shaped for receiving handle 5612. For example, a proximal end 5714 of handle 5612 has a hexagonal shaped opening that operatively couples to a hexagonal shaped end of lift control mechanism 5716. The surfaces of the hexagonal surface mate with the surfaces of the proximal end 5714 of handle 5612 for distributing the torque required to rotate the lift control mechanism 5716 when increasing a gap between superior surface 5602 and inferior surface 5706 to distract surfaces of the muscular-skeletal system. Distributing the torque over a large surface area prevents stripping of either the hexagonal shaped opening of handle 5612 or the hexagonal shaped exposed end of lift control mechanism 5716 when the device is under load. In one exemplary embodiment, a release and locking mechanism fastens handle 5612 to the lift control mechanism 5716. Pressing or sliding unlocking button 5618 releases the locking mechanism to allow removal of handle 5612.

Figure 58:
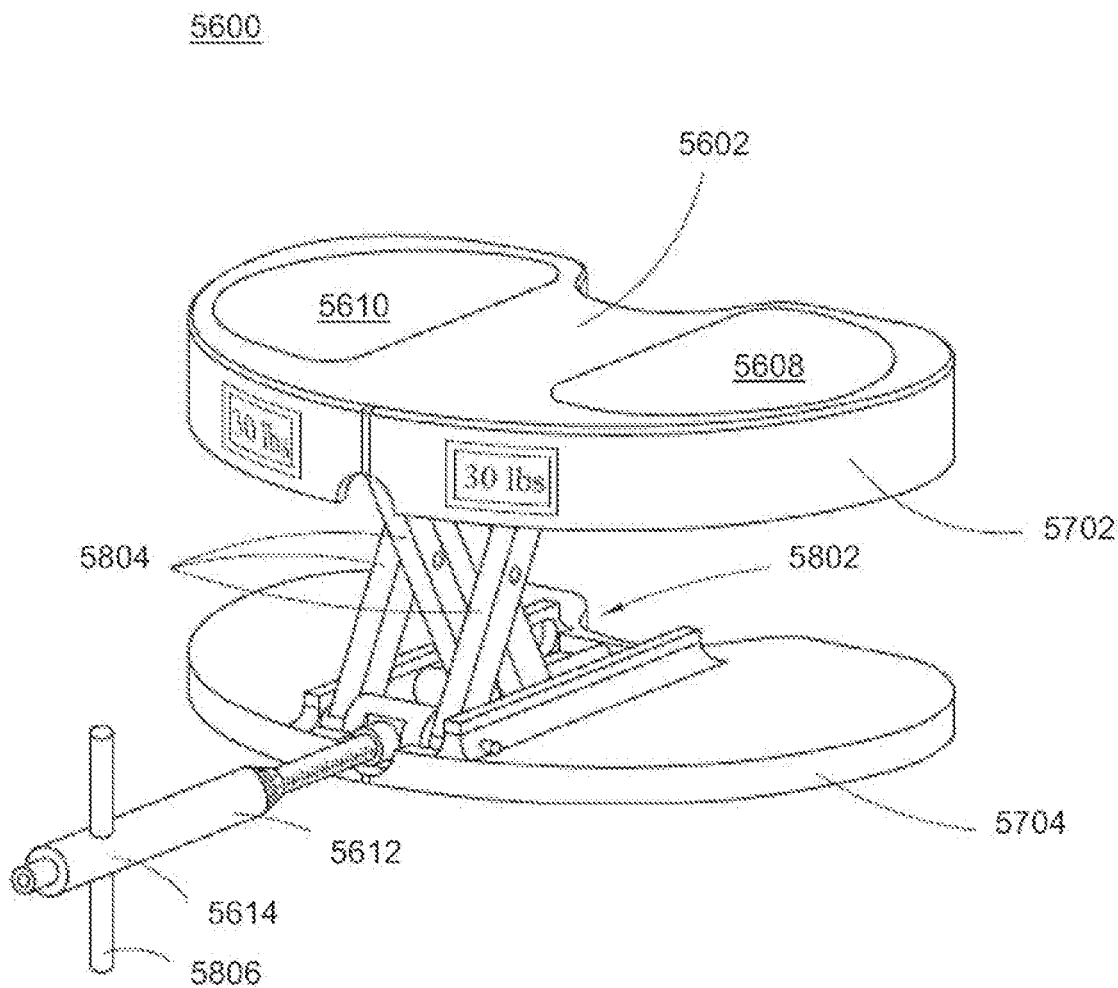
FIG. 58 is a perspective view of the dynamic distractor of FIG. 56 opened for distracting two surfaces of the muscular-skeletal system.

FIG. 58 is a view of dynamic distractor 5600 opened for distracting two surfaces of the muscular-skeletal system in accordance with an exemplary embodiment. The lift mechanism 5802 comprises in this example a scissor mechanism 5804 for raising and lowering upper support structure 5702 with respect to lower support structure 5704. In one exemplary embodiment, scissor mechanism 5804 comprises more than one support structure each having a pivot. Scissor mechanism 5804 is operatively coupled to an interior surface of upper support structure 5702 and an interior surface of lower support structure 5704. The structural beams are pinned to allow pivoting around the axis of attachment. The remaining beam-ends rest on the interior surfaces of either the upper and lower support structures 5702 and 5704. The beam-ends not fastened to the interior surfaces support upper and lower support structures 5702 and 5704 under load. Threaded rod 5716 is operatively coupled between the beam-ends of scissor mechanism 5804 corresponding to lower support structure 5704. Rotating rod 5716 can increase or decrease distance between beam ends of the scissor mechanism 5804.

Figure 59:
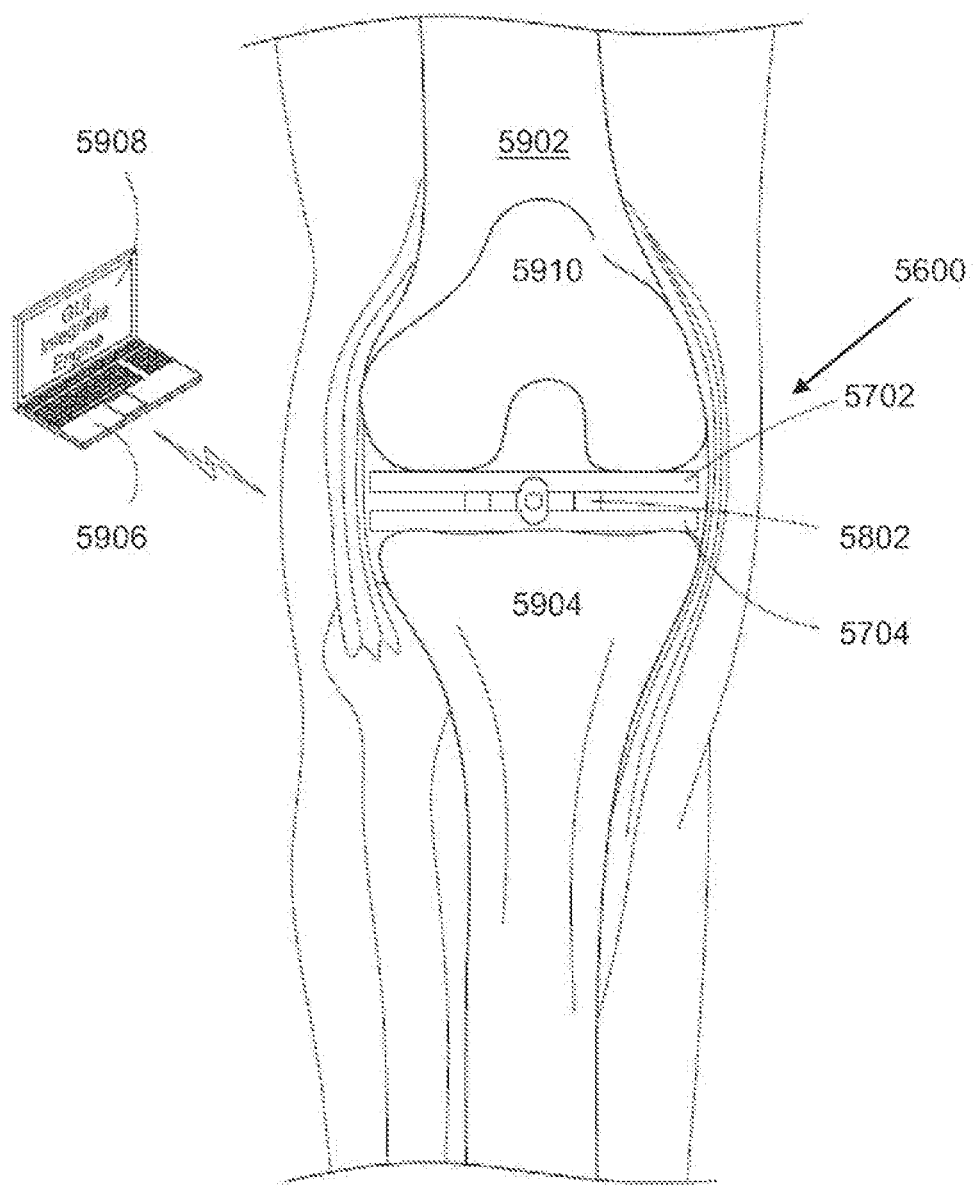
FIG. 59 is a fragmentary anterior view of an exemplary embodiment of a dynamic distractor placed in a knee joint according to the invention.

A rod 5806 can be coupled to opening 5614 of handle 5612. The rod 5806 can be used to reduce torque needed to rotate threaded rod 5716 in either direction under load. Increasing a distance between beam-ends of scissor mechanism 5804 reduces the gap between superior surface 5602 and inferior surface 5706 as the two or more beams pivot around a centrally located axis. Conversely, decreasing a distance between beam-ends of scissor mechanism 5804 increases the gap between superior surface 5602 and inferior surface 5706, FIG. 59 is an anterior view of a dynamic distractor 5600 placed in a knee joint in accordance with an exemplary embodiment. In the non-limiting example, a distal end 5910 of a femur 5902 is shown having a femoral implant. The femoral implant has artificial condyles that contact sensors 5608 and 5610. The proximal end of a tibia 5904 has been initially shaped for receiving a tibial implant. As is well known by one skilled in the art, a complete knee implant comprises the tibial implant, the femoral implant, and an insert that includes bearing surfaces that mate with the artificial condyle surfaces of the femoral implant. In one exemplary embodiment, dynamic distractor 5600 includes an adjustable handle 5612 that aids in the insertion of the spacer portion into a joint region of the muscular-skeletal system. For example, the spacer portion of dynamic distractor 5600 is inserted into the knee joint using handle 5612 but then is rotated away from the patellar tendon, collapsed into the trail, or removed to allow the reduction of the patella to depict loads on the instrument. The thickness or height of the three components is contemplated for the bone surface preparation when using dynamic distractor 5600. In one exemplary embodiment, the combined thickness of the femoral implant, final insert, and tibial implant is approximately 20 millimeters thick. Adjustments to the prepared bone surfaces and thickness of the insert are made during surgery using data provided by dynamic distractor 5600 to ensure correct loading, balance, and alignment.

Sensors 5608 and 5610 include circuitry for communication with a processing unit 5906. In one embodiment, data is sent wirelessly using a radio frequency communication standard such as Bluetooth, UWB, or Zigbee. The data can be encrypted to securely transmit the patient information and maintain patient privacy. In one exemplary embodiment, external processing unit 5906 is in a notebook computer, a personal computer, or custom equipment. For illustration purposes, external processing unit 5906 is shown in a notebook computer that includes software and a GUI designed for the surgical application. The notebook computer has a display 5908 that can be used by the medical staff during the operation to display real time measurement from dynamic distractor 5600. The notebook computer is typically placed outside the surgical zone but within viewing range of the surgeon.

A substantial benefit of dynamic distractor 5600 is in performing soft tissue release both in extension and in flexion. In extension, dynamic distractor 5600 can be set to a height corresponding to an insert size. In one embodiment, manufacturers of an implantable joint will provide specifications for load, balance, and alignment once sufficient clinical data has been generated. The surgeon can also manipulate the patient's leg to subjectively gauge the loading on the joint. The surgeon can adjust dynamic distractor 5600 to increase or decrease the height or gap corresponding to a different thickness insert size until a desired loading is achieved. A substantial imbalance corresponds to a differential loading measured by sensors 5608 and 5610 outside a predetermined range. The loading measured by sensors 5608 and 5610 should be approximately equal in each compartment. The data provided by sensors 5608 and 5610 can be used to provide a solution to the surgeon. For example, data from sensors 5608 and 5610 is sent wirelessly to processing unit 5906. The data indicates a substantial differential pressure between measurements from sensors 5608 and 5610 (i.e., imbalance). In one embodiment, the data can be processed and displayed on display 5908 with suggestions for the removal of material from the tibial surface to reduce the differential reading. The suggestion can include where material should be removed and how much material is removed from the tibial surface. Alternatively, the assessment of the loading and differential between compartments can indicate that soft tissue release is sufficient to bring the joint within predetermined ranges for absolute load and balance.

A further benefit of dynamic distractor 5600 is in soft tissue release to modify loading measured by sensors 5608 and 5610 and the differential (i.e., balance) between the measured values in each compartment. Dynamic distractor 5600 remains in place while soft tissue release is being performed allowing for real time measurement and modification to occur. The feedback to the surgeon is immediate as the soft tissue cuts are made. Two issues are resolved by dynamic distractor 5600. An open area formed between the interior surfaces of upper support structure 5702 and lower support structure 5704 under distraction provides surgical access. In most cases, the gap is sufficient to allow a scalpel or blade access to the lateral or medial ligaments for soft tissue release in the gap or peripheral to dynamic distractor 5600. In general, soft tissue release requires anterior access to the joint space. Handle 5612 of dynamic distractor 5600 can be removed providing further anterior access to the joint. Alternatively, handle 5612 is hinged or includes a joint allowing it to be positioned away from the surgical area. Thus, dynamic distractor 5600 enables soft tissue release by the surgeon to adjust the absolute loading measured by sensors 5608 and 5610 in each compartment to be within a predetermined range and to adjust the difference in compartment loadings within a predetermined range without removing the device.

Figure 60:
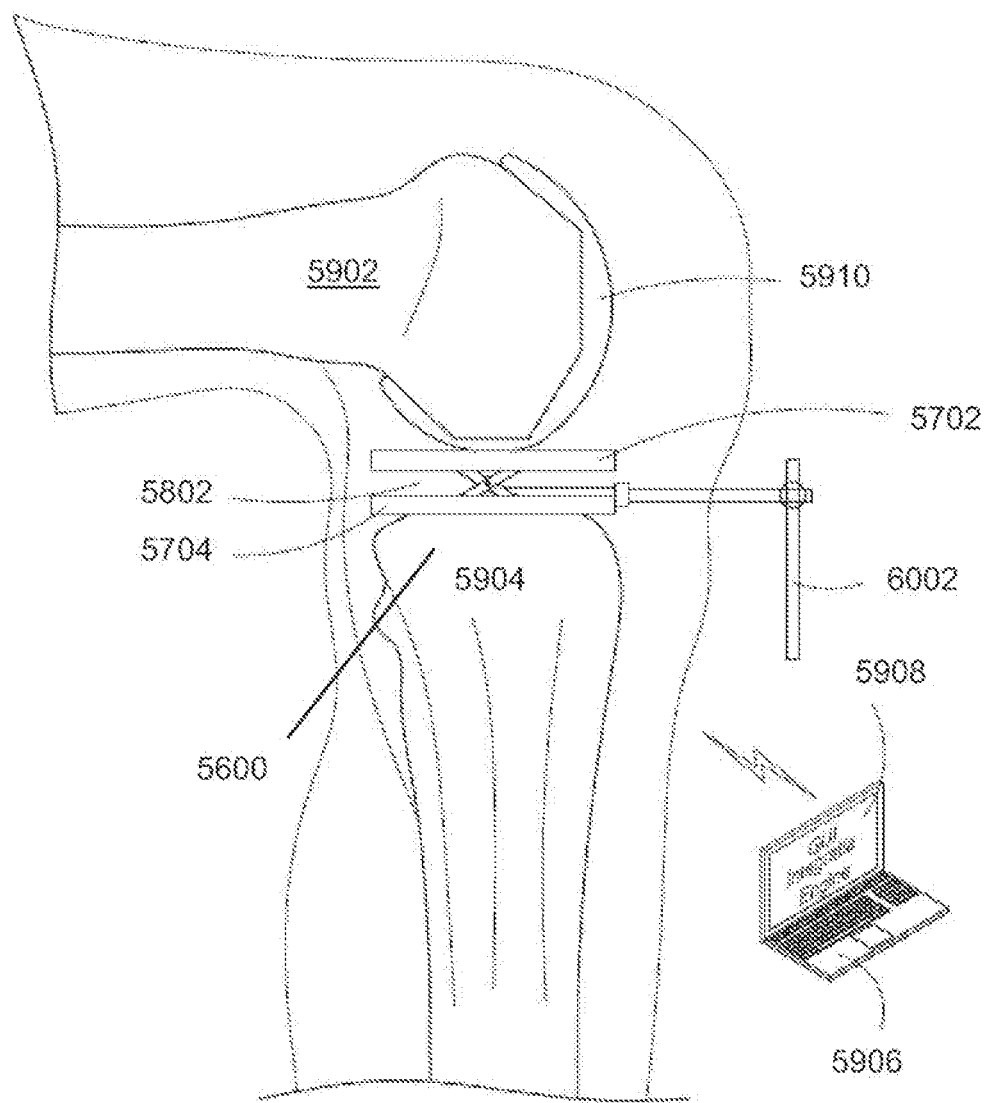
FIG. 60 is a fragmentary lateral view of the dynamic distractor of FIG. 59 in a knee joint positioned in flexion.

FIG. 60 is a lateral view of dynamic distractor 5600 in a knee joint positioned in flexion in accordance with an exemplary embodiment. In a non-limiting example, load and balance measurements are performed using dynamic distractor 5600 with the leg in at least two positions (e.g., the leg in extension and the leg in flexion). For example, measurements are taken in extension as disclosed hereinabove and in flexion with the leg positioned having femur 5902 forming a ninety-degree angle to tibia 5904. In one embodiment, accelerometers in sensors 5608 and 5610 are used to determine relative positioning of the femur and tibia to one another. Under user control, measurements are taken at several points over the range of motion with dynamic distractor 5600 in place, thereby substantially simplifying a data collection process. Measurements over the range of motion can be taken when the femoral implant has been installed or if the distal femur has not been modified. Alternatively, dynamic distractor 5600 can be reduced in height by rotating handle 5612 until there is sufficient room to move the leg to a new position and then increasing the height of distractor 5600 to create the appropriate gap.

Another beneficial feature of opening 5614 of handle 5612 is the ability to place drop alignment rod 6002 therethrough. Drop alignment rod 6002 is a visual aid for the surgeon and is used to ensure that the leg is aligned adequately when the load and balance measurements are taken. Drop alignment rod 6002 is used in conjunction with knowledge of the leg mechanical axis or with markers placed on the patient to check alignment. The surgeon aligns alignment rod 6002 to the leg mechanical axis and makes a subjective determination that the leg is correctly positioned. The surgeon can increase accuracy by pre-identifying points on the mechanical axis. The surgeon has the option of making adjustments if drop alignment rod 6002 indicates a potential positional error. Drop alignment rod 6002 can be tapered having a section with a greater width than opening 5614 to retain it in place and prevent it from falling through the opening 5614. Other embodiments to retain drop alignment rod 6002 can also be used.

Alternatively, drop alignment rod 6002 can be a smart alignment aid for the surgeon that incorporates electronics similar to that described in FIG. 2. In general, drop alignment rod includes sensors to allow depiction of the mechanical axis. For example, drop alignment rod 6002 can incorporate sensors to identify position in three-dimensional space. The electronics allow drop alignment rod 6002 to communicate with pre-operative defined locations or locations that are identified at the time of surgery using locator electronics. The drop rod can house light emitters to depict an axis as will be discussed in more detail hereinbelow. The electronics can include communication to external processing unit 5906 with a graphic user interface that has the mechanical axis loaded therein.

Figure 61:
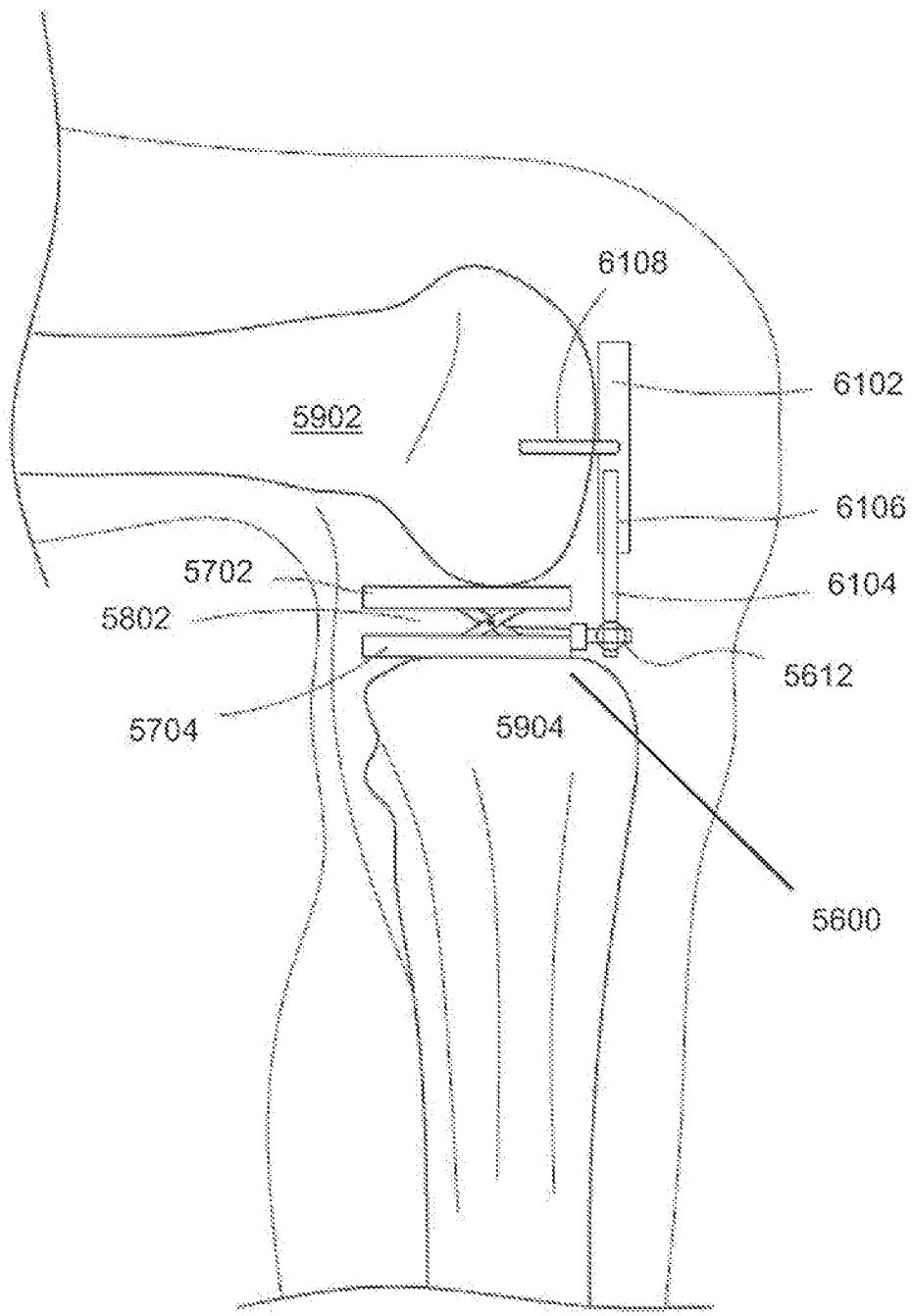
FIG. 61 is a fragmentary lateral view of the dynamic distractor of FIG. 59 in a knee joint coupled to an exemplary embodiment of a cutting block according to the invention.

FIG. 61 is a lateral view of a dynamic distractor 5600 in a knee joint coupled to a cutting block 6102 in accordance with an exemplary embodiment. In general, the surgeon utilizes surgical tools to obtain appropriate bony cuts to the skeletal system. The surgical tools are often mechanical devices used to achieve gross alignment of the skeletal system prior to or during an implant surgery. In the knee example, mechanical alignment aids are often used during orthopedic surgery to check alignment of the bony cuts of the femur and tibia to the mechanical axis of the leg. The mechanical alignment aids are not integrated together, take time to deploy, and have limited accuracy. Dynamic distractor 5600 in concert with cutting block 6102 is an integrated system for achieving alignment that can greatly reduce set up time thereby minimizing stress on the patient.

As illustrated, the leg is in flexion having a relational position of 90 degrees between femur 5902 and tibia 5904. A femoral rod 6108 is coupled through the intermedullary canal of femur 5902. A cutting block 6102 is attached to the femoral rod 6108 for shaping a portion of the surface of the distal end of femur 5902 for receiving a femoral implant. Knee replacement surgery entails cutting bone a certain thickness and implanting a prosthesis to allow pain relief and motion. During the surgery, instruments are used to assist the surgeon in performing the surgical steps appropriately. Dynamic distractor 5600 aids the surgeon by allowing quantitative measurement of the gap and parameter measurement during all stages of the procedure. For the knee, the data can supplement a surgeon's "feel" by providing data on absolute loading in each compartment, the load differential between compartments, positional information, and alignment information.

The portion of the surface of the distal end of femur 5902 in contact with dynamic distractor 5600 is shaped in a subsequent step. In a non-limiting example, the portion of the condyles in contact with superior surface 5602, sensor 5608, and sensor 5610 are the natural condyles of the femur. The portion of the distal end of femur 5902 being shaped corresponds to the condyle portion that would be in contact with the final spacer while the leg is in extension and partially through the range of motion. In at least one exemplary embodiment, an uprod 6104 of dynamic distractor 5600 couples to cutting block 6102. Uprod 6104 aids in the alignment of the cutting block 6102 to dynamic distractor 5600 and tibia 5904. Uprod 6104 further stabilizes cutting block 6102 to prevent movement as the distal end of femur 5902 is shaped.

In one exemplary embodiment, handle 5612 is removed and an uprod 6104 is attached to threaded rod 5716. The uprod 6104 can include a hinge that positions rod 6104 vertically to mate with cutting block 6102. Alternatively, handle 5612 can include a hinge. In this example, handle 5612 is uprod 6104 and is inserted into cutting block 6102. Furthermore, uprod 6104 can be fastened or coupled to an opening or feature in handle 5612 to couple to cutting block 6102. In general, uprod 6104 is placed at a right angle to the inferior surface of lower support structure 5704 of dynamic distractor 5600. In a prior step, the leg alignment can be checked to ensure it is within a predetermined range of the mechanical axis. In one exemplary embodiment, uprod 6104 aligns approximately to the mechanical axis to secure cutting block 6102 in an appropriate geometric orientation. Cutting block 6102 includes a channel 6106 for receiving uprod 6104. Uprod 6104 can be adjustable in length to simplify insertion. As previously mentioned, uprod 6104 is attached to dynamic distractor 5600 to align with the mechanical axis of the leg corresponding to tibia 5904. Fitted in the opening and into channel 6106, uprod 6104 maintains a positional relationship between cutting block 6102, dynamic distractor 5600, femur 5902, and tibia 5904. More specifically, the proximal surface of tibia 5904 is aligned to the mechanical axis thereby fixing the position of femur 5902 and cutting block 6102 in a similar fixed geometric relational position. Thus, the distal end of femur 5902 is cut having surfaces parallel to the proximal tibial surface by coupling dynamic distractor 5600 to cutting block 6102 through uprod 6104.

Figure 62:
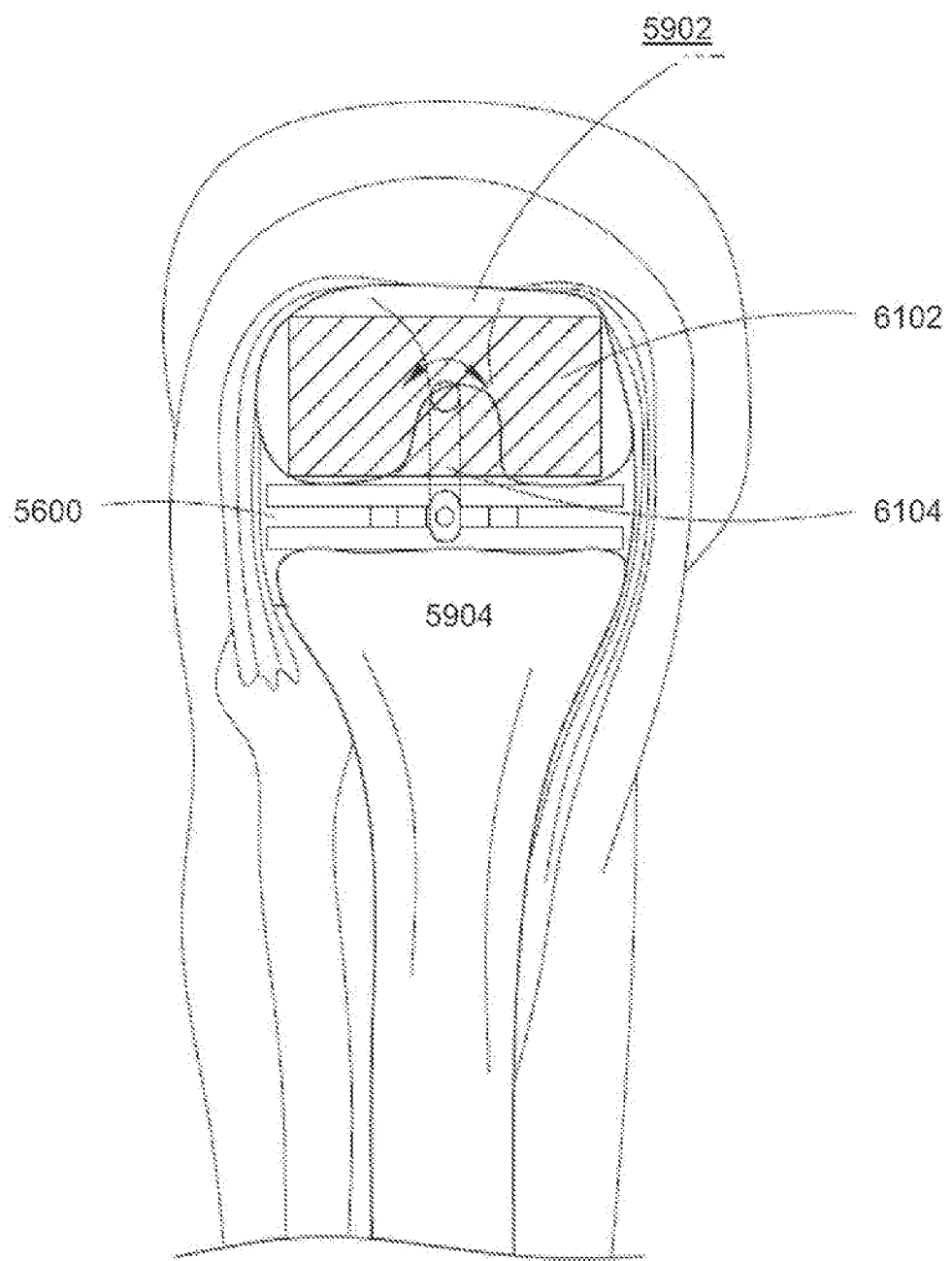
FIG. 62 is a fragmentary anterior view of the cutting block coupled to the dynamic distractor of FIG. 61.

FIG. 62 is an anterior view of a cutting block 6102 coupled to dynamic distractor 5600 in accordance with an exemplary embodiment. Cutting block 6102 is attached to the distal end of femur 5902. Femoral rod 6108 extends through cutting block 6102 into the intermedullary canal. Uprod 6104 is shown extending vertically into channel 6106 of cutting block 6102. In combination, femoral rod 6108 and uprod 6104 prevent movement and maintain alignment of the cutting block to the leg mechanical axis. As shown, cutting block 6102 is illustrated as rectangular in shape. Cutting block 6102 is shaped to form a predetermined bone shape on the distal end of femur 5902 for receiving a femoral implant. Thus, the shape of cutting block 6102 can vary significantly from that shown depending on the implant. The size of the cutting block 6102 corresponds to the distal end size and the femoral implant selected by the surgeon. The surgeon uses a bone saw to remove portions of the distal end of femur 5902 in conjunction with cutting block 6102. In general, the cutting block 6102 acts as a template to guide the bone saw and to cut the distal end of the femur in a predetermined geometric shape. As disclosed previously in the example, the portion of the distal end of femur 5902 that is shaped corresponds to the contact portion of the condyles when the leg is in full extension and partially in flexion (i.e., <90 degrees). As mentioned previously, the portion of the distal end of femur 5902 in contact with the superior surface 5602 of dynamic distractor 5600 is shaped in a subsequent step.

Figure 63:
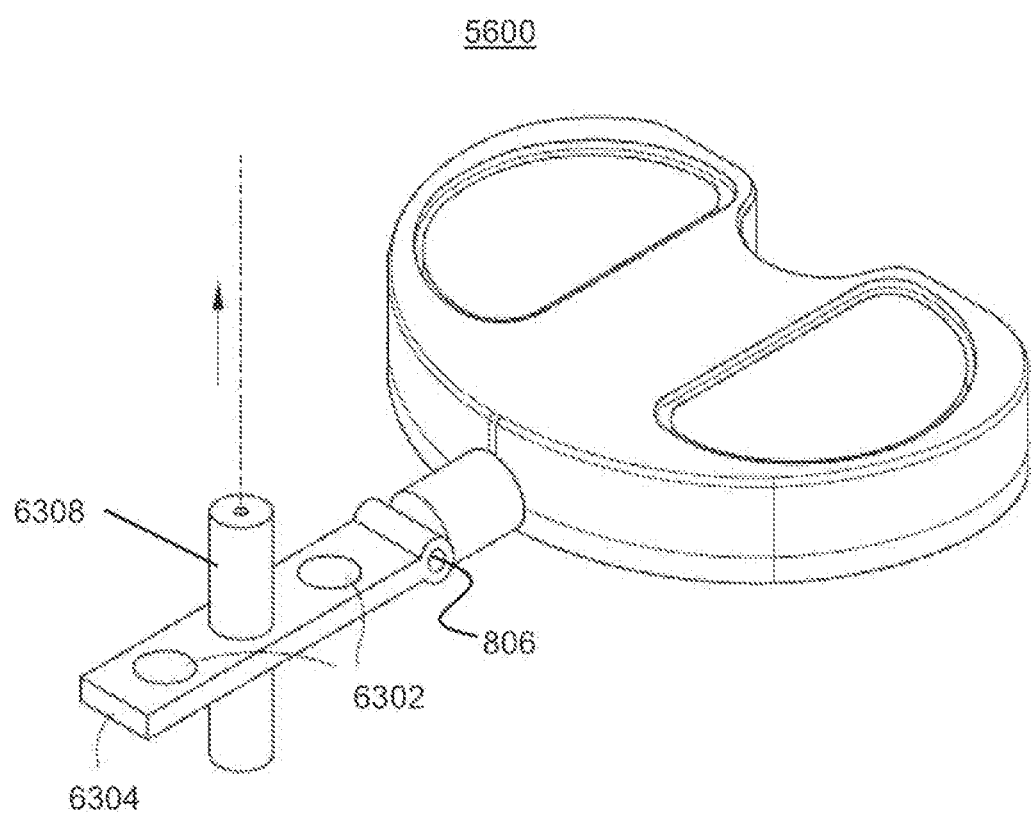
FIG. 63 is a perspective view of an exemplary embodiment of a dynamic distractor including alignment measures according to the invention.

FIG. 63 is an illustration of dynamic distractor 5600 including alignment in accordance with an exemplary embodiment. Dynamic distractor 5600 includes one or more recesses 6302 in a handle 6304 for receiving an alignment aid to align a leg along the mechanical axis. In one embodiment, handle 6304 can be handle 5612 that includes recesses 6302. Alternatively, handle 6304 is a separate handle for dynamic distractor 5600. Prior to checking alignment, handle 5612 is removed from dynamic distractor 5600. Handle 6304 is then coupled to threaded rod 5716 for raising and lowering the support structures.

Initial bony cuts are made in alignment with the mechanical axis of the leg. In the knee example, the alignment aid is used to check that the femur and the tibia are correctly oriented prior to cutting. The surfaces of the bones are cut in alignment to the mechanical axis using a jig. Thus, the cut surfaces on the distal end of the femur and the proximal end of the tibia are aligned and can be used as a reference surfaces during the procedure. Alternatively, the alignment aid can be used to verify alignment throughout the procedure. Recesses 6302 can be thru-holes in handle 6304. In a non-limiting example, the alignment aid is one or more lasers 6308. Laser 6308 is/are used to point along the mechanical axis of the leg. In one exemplary embodiment, lasers 6308 are used to check alignment of the leg. A first laser is used to point in the direction of the hip joint. A second laser is used to point towards the ankle. In one embodiment, the first and second lasers are integrated into a single body. Handle 6304 further comprises a hinge 806 to change the angle at which lasers 6308 are directed. The housing of lasers 6308 includes a power source such as a battery to generate the monochromatic light beam. The housing fits within one of recesses 6302 or a thru-hole. Lasers 6308 can be a disposable item that is discarded after the surgery is completed.

Figures 64, 65:
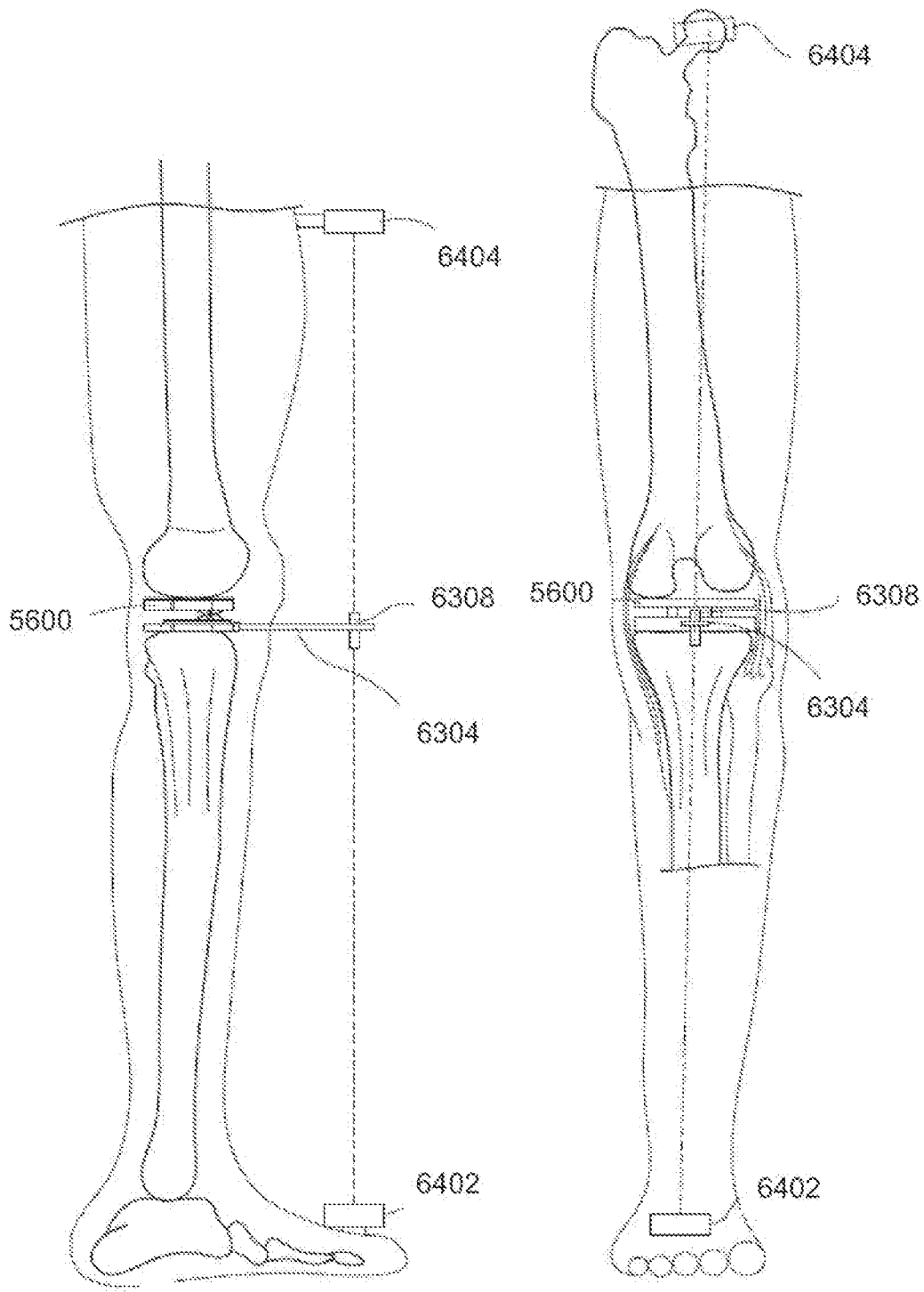
FIG. 64 is a fragmentary side elevational view of a leg in extension with an exemplary embodiment of a dynamic distractor in the knee joint region according to the invention.
FIG. 65 is a fragmentary, front elevational view of the leg in extension with the dynamic distractor of FIG. 64.

FIG. 64 is a side view of a leg in extension with dynamic distractor 5600 in the knee joint region in accordance with an exemplary embodiment. The mechanical axis of the leg is approximately a straight line from the center of the femoral head through the knee joint and extending to the middle of the ankle joint. In a correctly aligned knee joint, the mechanical axis will pass approximately through the center of the knee joint. Alignment can be checked when dynamic distractor 5600 is positioned in the knee joint region. As illustrated, the leg is in extension with handle 6304 extending vertically from the knee joint region. In one embodiment, a target 6402 is placed in an ankle or toe region of the foot in a path corresponding to center of the ankle on the mechanical axis of the leg. Similarly, a target 6404 is placed in a path corresponding to the center of the head of the femur on the mechanical axis of the leg. Targets 6402 are placed at a height similar to that of lasers 6308. Lasers 6308 are installed in the handle with one pointing in the direction of the hip joint and another pointing in the direction of the ankle joint. From the top view, lasers 6308 send out a beam of light from a position that corresponds to the center of the knee. In one embodiment, the direction of the beam from lasers 6308 is directed perpendicular to a plane of the prepared surface of the proximal end of the tibia.

Lasers 6308 are directed perpendicular to the inferior surface of dynamic distractor 5600. The placement of dynamic distractor 5600 on the prepared tibial surface is such that handle 6304 extends vertically at a point corresponding to the center of the knee joint. The leg is aligned correctly when the beams from lasers 6308 hit the target at the points corresponding to the center of the head of the femur and the center of the ankle. Lasers 6308 are positioned to align with the center of the knee joint. The surgeon can make adjustments to the bone surfaces or utilize soft tissue release to achieve alignment with the leg mechanical axis when lasers 6308 are misaligned to the target. The system can be used to give a subjective or a measured determination on leg alignment in relation to a vargus or valgus alignment. The direction of misalignment in viewing targets 6402 and 6404 will dictate the type of correction and how much correction needs to be made. In an alternate exemplary embodiment, lasers 6308 can be aimed such that the beam is viewable along the leg in a region by the center of the femoral head and the center of the angle. The surgeon can use this as a subjective visual gauge to determine if the leg is in alignment to the mechanical axis and respond appropriately, depending on what is viewed.

FIG. 65 is a front view of a leg in extension with dynamic distractor 5600 in the knee joint area in accordance with an exemplary embodiment. Dynamic distractor 5600 can measure spacing between the distal end of the femur and the tibia, loading in each compartment, and differential loading between compartments. The data can be sent to a processing unit and display as disclosed hereinabove. As mentioned previously, the mechanical axis of the leg corresponds to a straight line from the center of the ankle, through the center of the knee, and the center of the femoral head. Targets 6402 and 6404 are respectively located overlying the mechanical axis in an area local to the ankle and the hip regions. Targets 6402 and 6404 can include a fixture such as a strap, brace, or jig to hold the targets temporarily along the mechanical axis. Lasers 6308 are enabled and placed in handle 6304. FIG. 65 illustrates that targets 6402 and 6404 are on approximately the same plane as beams emitted by lasers 6308 such that the beams impinge on a target unless grossly misaligned. Targets 6402 and 6404 can include calibration markings to indicate a measure of the misalignment. Alternatively, handle 6304 is hinged allowing adjustment of the angle at which the beam from lasers 6308 is directed. The direction of the lasers 6308 corresponds to the plane of the bone cuts for the implant and the balance of the joint. Thus, the surgeon using a single device has both quantitative and subjective data relating to alignment to the mechanical axis, loading, balance, leg position, and gap measurement that allows gross/fine tuning during surgery that results in more consistent orthopedic outcomes.

Figure 66:
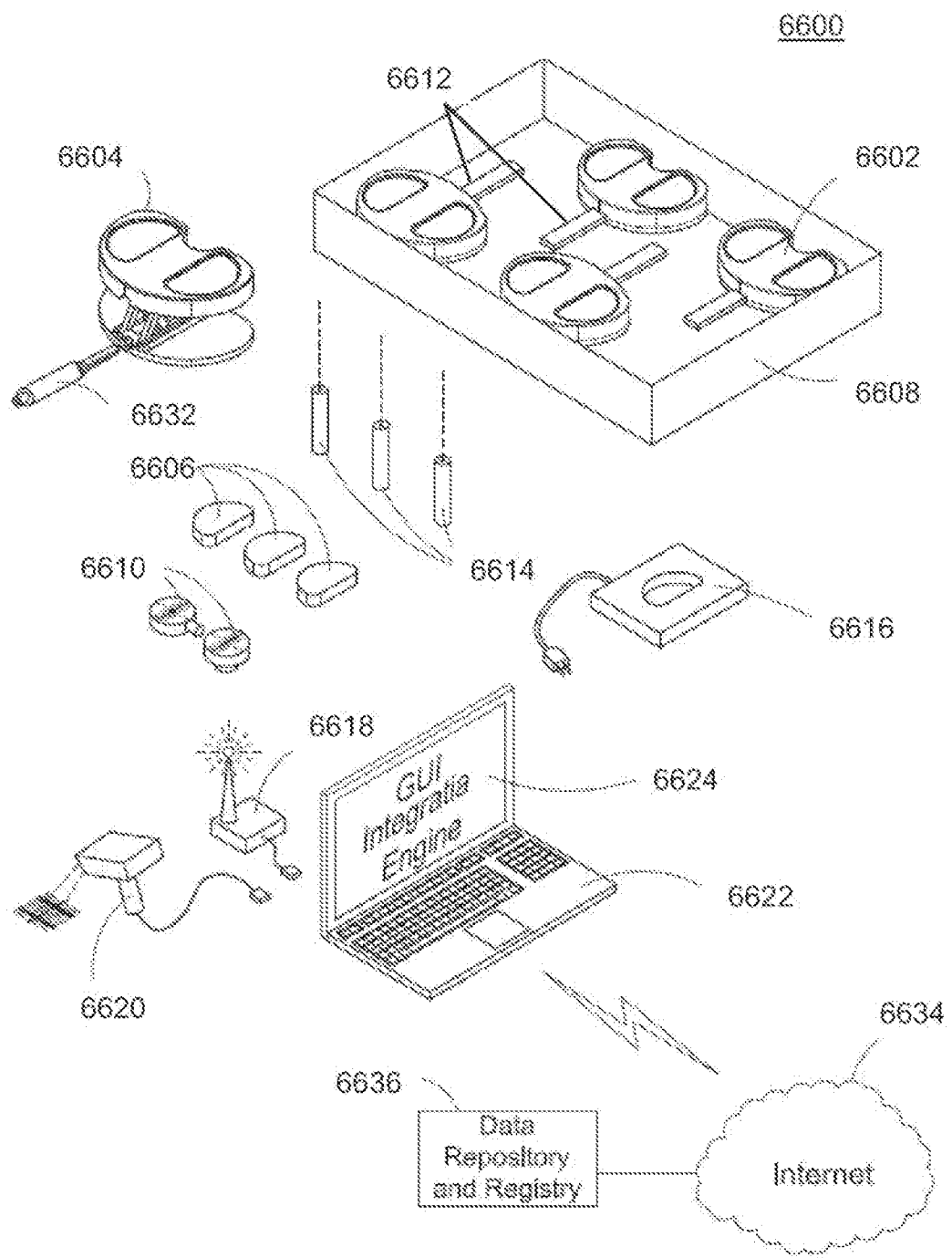
FIG. 66 is a perspective view of an exemplary embodiment of a system and kit for measuring one or more parameters of a biological life form according to the invention.

FIG. 66 is an illustration of a system or kit 6600 for measuring one or more parameters of a biological life form in accordance with an exemplary embodiment. In a non-limiting example, the system provides real time measurement capability to a surgeon of one or more parameters needed to assess a muscular-skeletal system. System 6600 comprises a plurality of spacer blocks 6602, a distractor 6604, sensors 6606, targets 6610, lasers 6614, a charger 6616, a receiver 6618, a reader 6620, a processing unit 6622, a display 6624, a drop rod, an uprod, a cutting block, a handle 6632, and a dynamic data repository and registry 6636. The system is adaptable to provide accurate measurements of parameters such as distance, weight, strain, pressure, wear, vibration, viscosity, and density to name but a few. In one exemplary embodiment, system 6600 is used in orthopedic surgery and more specifically to provide intra-operative measurement during joint implant surgery. System 6600 is adapted for orthopedic surgery and more specifically for knee surgery to illustrate operation of the system.

In general, system 6600 provides alignment and parameter measurement system for providing quantitative measurement of the muscular-skeletal system. In one exemplary embodiment, system 6600 is integrated with tools commonly used in orthopedics to reduce an adoption cycle to utilize new technology. System 6600 replaces standalone equipment or dedicated equipment that is used only for a small number of procedures that justifies the extra time and set up required to use this type of equipment. Furthermore, it is well known, that dedicated equipment can cost hundreds of thousands or millions of dollars for a single device. Many hospitals and other healthcare facilities cannot afford the high capital cost of these types of systems. Moreover, specialized equipment such as robotic systems or alignment systems for orthopedic surgery typically has a large footprint. The large footprint creates space and cost issues. The equipment must be stored, set up, calibrated, placed in the operating room, and then removed.

Conversely, measurement and alignment components of system 6600 are low cost disposables that make the measurement technology more accessible to the general public. There is no significant capital investment required to use the system. Moreover, payback begins immediately with use in providing quantitative information related to procedures thereby allowing analysis of outcomes based how the parameters being measured affect the procedure being measured. The data is used to initiate predetermined specifications for the procedure that can be measured and adjusted during the course of the procedure thereby optimizing the outcomes and reducing revisions. As mentioned previously, system 6600 can be used or integrated with tools that the majority of orthopedic surgeons have substantial experience or familiarity using on a regular basis. In one exemplary embodiment, sensors 6606 are placed in a spacer that separates two surfaces of the muscular-skeletal system. In a non-limiting example, the spacer can be spacer blocks 6602 or distractor 6604. A measurement of the parameter is taken after the spacer is inserted between at least two surfaces of the muscular-skeletal system. Sensors 6606 are in communication with processing unit 6622. In one embodiment, the processing unit 6622 is outside the sterile field and includes display 6624 and a GUI to provide the data in real time to the surgeon. Thus, the learning cycle can be very short to provide real time quantitative feedback to the surgeon as well as storing the data for subsequent use.

In a non-limiting example, a spacer separates two surfaces of the muscular-skeletal system. The spacer has an inferior surface and a superior surface that contact the two surfaces. The spacer can have a fixed height or can have a variable height. The fixed height spacer is known as spacer blocks 6602. Each spacer block 6602 has a different thickness. The variable height spacer is known as the distractor 6604. The surface area of spacer blocks 6602 and distractor 6604 that couple to the surfaces of the muscular-skeletal system can also be provided in different sizes. The handle 6632 extends from the spacer and typically resides outside or beyond the two surface regions. The handle 6632 is used to direct the spacer between the two surfaces. In one exemplary embodiment, the handle 6632 operatively couples to a lift mechanism of the distractor 6604 to increase and decrease a gap between the superior and inferior surfaces of the spacer. The spacer and handle 6632 is part of system 6600 to measure alignment of the muscular-skeletal system. In one exemplary embodiment, at least one of the surfaces of the muscular-skeletal system that contacts the spacer has an optimal alignment to a mechanical axis of the muscular-skeletal system. The system measures the surface to mechanical axis alignment. In a non-limiting example, the misalignment can be corrected by a surgeon when the surface is misaligned to the mechanical axis outside a predetermined range as disclosed below.

Knee replacement surgery entails cutting bone having a predetermined spacing and implanting a prosthesis to allow pain relief and motion. During the surgery, instruments are used to assist the surgeon in performing the surgical steps appropriately. The majority of surgeons continue to use passive spacers to aid in defining the gaps between the cut bones. The thickness of the final insert is selected after placing one or more trial inserts in the artificial joint implant. The determination of whether the implanted components are correctly installed is still to a large extent by the "feel" of the surgeon through movement of the leg. In general, spacer blocks 6602 and distractor 6604 of system 6600 is a spacer having an inferior and superior surface that separate at least two surfaces of the muscular-skeletal system. In the knee example, the inferior and superior surfaces are inserted between the femur and tibia of the knee. At least one of the inferior or superior surfaces of spacer blocks 6602 and distractor 6604 have a cavity or recess for receiving sensors 6606. In one exemplary embodiment, the cavity is on the superior surface of spacer blocks 6602 and distractor 6604. A gap between the surfaces of distractor 6604 is adjustable as described hereinabove. Tray 6608 includes multiple spacer blocks 6602 each having a different thickness. Thus, spacer blocks 6602 and distractor 6604 provide the surgeon with more than one option to measure spacing, alignment, and loading during the procedure. A benefit of the system is the familiarity that the surgeon will have with using similar type devices, thereby reducing the learning curve to utilize system 6600. Furthermore, system 6600 can comprise spacer blocks 6602 and distractor 6604 having spacer blocks having different sized superior and inferior surface areas to more readily accommodate different bone shapes and sizes.

In general, a rectangle is formed by the bony cuts during surgery. The imaginary rectangle is formed between the cut distal end of a femur and the cut proximal end of tibia in extension and in conjunction with the mechanical axis of the lower leg. The prepared surfaces of the femur and tibia are shaped to respectively receive a femoral implant and a tibial implant. The femoral and tibial surfaces are parallel to one another when the leg is in extension and in flexion at ninety degrees. A predetermined width of the rectangle is the spacing between the planar surface cuts on femur and tibia. The predetermined width corresponds to the thickness of the combined orthopedic implant device comprising the femoral implant, an insert, and the tibial implant. A target thickness for the initial cuts is typically on the order of twenty millimeters. The insert is inserted between the installed femoral implant and the tibial implant. In a full knee implant, the insert has two bearing surfaces that are shaped to receive the condyle surfaces of the femoral implant.

In at least one exemplary embodiment, when inserted into the spacer blocks 6602 and/or distractor 6604, sensors 6606 can measure load and position. While it may be beneficial for the sensors 6606 to be charged when first use, alternatively, sensors 6606 are placed in a charger 6616 prior to the implant surgery being performed. Charger 6616 provides a charge to an internal power source within sensors 6606 that will sustain sensor measurement and data transmission throughout the surgery. Charger 6616 can fully charge sensor 6606 or be used as a precautionary measure to insure the temporary power storage is holding sufficient charge. Charger 6616 can charge the sensors 6606 via a wireless connection through a sterilized packaging. Sensors 6606 are in communication with processing unit 6622. Sensors 6606 include a transmitter for sending data. Processing unit 6622 can be logic circuitry, a digital signal processor, microcontroller, microprocessor, or part of a system having computing capability. As shown, processing unit 6622 is a notebook computer having a display 6624. The communication between sensors 6606 and processing unit 6622 can be wired or wireless. In one embodiment, receiver 6618 is coupled to the processing unit 6622 for wireless communication. A carrier signal for data transmitted from sensors 6606 can be radio frequency, infrared, optical, acoustic, and microwave to name but a few. In a non-limiting example, receiver 6618 receives data via a radio frequency signal in a short range unlicensed band sufficient for transmission within the size of an operating room. Information from processing unit 6622 can be sent through the Internet 6634 to a dynamic data repository and registry 6636 for long-term storage. The dynamic data repository and registry 6636 will be discussed in greater detail hereinbelow. In one exemplary embodiment, the data is stored in a server or as part of a larger database.

The surgeon uses system 6600 to aid in the preparation of bone surfaces, to measure loading, to measure balance, to check alignment, and to tune the knee joint prior to a final insert being installed. A reader 6620 is used to scan in information prior to or during the surgery. In one exemplary embodiment, the reader 6620 can be wired or wirelessly coupled to the processing unit 6622. Processing unit 6622 can process the information, display it on display 6624 for use during a procedure, and store it in memory and/or a database for long-term use. For example, information on components used in the surgery such as the artificial knee components or components of system 6600 can be converted to an electronic digital form using reader 6620 during the procedure. Similarly, patient information or procedural information can also be scanned in, input manually, or captured by other measures to processing unit 6622.

The leg is placed in extension and the knee joint is exposed by incision. In one exemplary embodiment, the surgeon prepares the proximal end of the tibia. The prepared tibial surface is typically at a 90-degree angle to the mechanical axis of the leg. Targets 6610 are placed overlying the mechanical axis near the ankle and hip joint. The surgeon can select one of the spacer blocks 6602 or dynamic distractor 6604 for insertion in the joint region. The selected spacer block has a predetermined thickness that is imprinted on the spacer block or can be displayed on display 6624 by scanning the information. Alternatively, distractor 6604 is distracted by the surgeon within the joint region. The amount of distraction can be read off of distractor 6604 or can be displayed on display 6624.

In a non-limiting example of aligning two surfaces of the muscular-skeletal system, alignment of the leg to the mechanical axis is measured and/or a subjective check can be performed by the surgeon using an alignment aid. At least one component of the alignment aid is disposable. The alignment aid comprises lasers 6614 connectable to a handle 6612 of the selected spacer block or a handle 6632 of distractor 6604 with the leg in extension. The alignment aid further includes targets 6610. Targets 6610, lasers 6614, or both can be disposable. Accelerometers in sensors 6606 provide positional information of the tibia in relation to the femur. For example, display 6624 will indicate that the angle between the tibia and femur is 180 degrees when the leg is in extension. The beam from lasers 6614 hit targets 6610 and provides a measurement of the position of the tibia in relation to the femur compared to the mechanical axis of the leg. In one exemplary embodiment, lasers 6614 are centrally located above the knee joint overlying the mechanical axis of the leg. The beam from lasers 6614 is directed perpendicular to the plane of the surface of the tibia. The beam from lasers 6614 will align and overlie the mechanical axis if the surface of the tibia is the perpendicular to the mechanical axis. The beam from lasers 6614 would hit targets 6610 at a point that indicates alignment with the mechanical axis. A valgus or vargus reading can be read where the beam hits the calibrated markings of targets 6610 if the leg is not aligned. The surgeon can then make an adjustment to bring the leg into closer alignment to the mechanical axis if deemed necessary. Jigs or cutting blocks can also be used in conjunction with lasers 6614 and targets 6610 to check alignment prior to shaping. The jigs or cutting blocks are used to shape the bone for receiving an implant. The distal end of femur and the proximal end of tibia are shaped for receiving orthopedic joint implants. In a further exemplary embodiment, sensors can be attached to the cutting jigs or devices to aid the surgeon in optimizing the depth and angles of their cuts.

As an example, knee replacement surgery can be divided into unicompartmental knee surgery, bicompartmental (Cruciate sparing), and total knee replacement surgery. Unicompartmental knee surgery is beneficial in the appropriate patient to relieve pain from arthritis in one compartment and restore the patient's knee function. Bicompartmental knee replacement allows retention of the cruciate ligaments while treating generalized knee arthritis. Unicompartmental knee surgery has shown long lasting benefits and an earlier recovery phase than the traditional total knee replacement. Patient selection is critical. The pathology must only affect one compartment (most commonly the medial side), the knee deformity must be minimal and passively correctable. Bicompartmental Knee replacements preserve the cruciate ligaments and provide the added stability of ligament retention for post-operative function. The prostheses have been modified over time and the bearing surfaces have shown the ability to function well into the second decade.

The last parameter to address is the surgical technique. If a unicompartmental or bicompartmental knee is positioned poorly, the components will fail early and will require a revision knee surgery. If the anterior cruciate ligament and the posterior cruciate ligament are not tensioned correctly along with the medial collateral ligament and the lateral collateral ligaments in a bicompartmental bicruciate knee replacement, the knee will not function well and a revision will be required. Positioning can be divided into several issues:

1) The femoral component and tibial component must be placed at the appropriate depth in the bone and must be sized and positioned correctly on the bone;
2) The components must be positioned appropriately to each other through all ranges of motion; and
3) The flexion and extension gaps (soft tissue tension) must be balanced in order for the knee to function appropriately and to avoid early bearing wear.

Through pre-op planning (using Xrays, Cat Scans, MRI's etc.), and intra-operative jigs, the correct component-to-component alignment and implant positioning can be achieved. Recently, Robotic technology has allowed physicians to precisely prepare the bone at the correct angles, depth, etc. The ability to precisely balance the knee through all ranges of motion has not been mastered, however. While performing a unicompartmental/bicompartmental knee replacement, physicians do not routinely release collateral ligaments to achieve alignment as physicians can do in total knee replacements. Also, the anterior cruciate and posterior cruciate ligaments are required to be present. The most important parameter is the ability to balance the knee in flexion and extension, coupled with correct mechanical leg alignment; this allows physicians to achieve near normal knee kinematics. This means that the amount of bone removed from the tibia and femur allows equal balance and loads on the prosthesis through all ranges of motion.

The ligaments must be tensioned and loaded appropriately as well. The present way physicians achieve this is through the concepts of replacing what is removed. The problem with this is that the physicians have unequal wear of the extension gap compared to the flexion gap in most medial knee arthritis. The anterior part of the knee is worn, while the posterior part of the knee is preserved. The opposite is true in lateral knee arthritis. The most common procedure to achieve correct balance is to cut the tibia first and place a feeler gage in between the femur and tibia and determine the flexion gap. The surgeon then extends the knee and uses feeler gauges to determine the balance between the femur and tibia in extension (the Extension Gap). The problems encountered with this present system are that the feeler gages are plastic with no fine pressure determination. The surgeon is taught to insert and pull out the feeler gage or distractor, and get a "feel" of what is right. This is difficult to perfect if the physician does not perform a large number of surgeries and is difficult to teach other surgeons what is a "correct" feel.

The tibia is cut first due to the fact that it will control alignment and it can affect the flexion and extension gap. The angle of tibia slope will affect the flexion gap. The amount of posterior femur resected will affect the flexion gap. The extensor gap is usually worn more in the medial arthritic knee. The amount of resection of the anterior and distal femur will affect the extension gap. The other concerns include, when presently changing depth and slope, the physician affects the angles of the bone cuts and ultimately how the components will load each other and articulate in the patient's knee, as well as the tension on the cruciate and collateral ligaments.

In one exemplary embodiment, the sensor system according to the invention allows real time loads on trial inserts, implants, and instruments during surgery. This gives the surgeon true pressure readings that help determine the depth, angle and placement of the components. The ability to transmit this information to a "smart instrument" or a robotic system allows the computer to process the information. This is compared to a preset algorithm that enables a smart instrument to refine the bone cuts to achieve optimal balance of the gaps, while maintaining precise component-to-component alignment. A smart instrument as referred to herein is any mechanical jig or cutting instrument that can receive and integrate information and use this information to enable surgical preparation of a joint. The sensor system can, then, be implanted in the final polyethylene insert to determine post-operative loads, kinematics, abnormal wear, or motion of the implant.

The sensor system in one exemplary embodiment includes an exciter/receiver that sends a signal to each other. When loads are applied to the plastic insert, the signal wave is deflected. The deflection of the energy wave and the time it takes to resume its resting state is placed over time and a value is produced. This value can be a parameter of load that is sent to a transistor. Nexense sensor technology described above can be used. Other sensors utilizing ultrasound, piezoelectrics. MEMS, fiberoptics, strain gauges, and sensor composites such as film can be employed in the system. The information provided by the sensors can be sent to a computer screen by wireless technology that is in present use. The surgeon can visually analyze this information. A signal can also be sent to a "smart instrument" that has a built in algorithm to burr or cut the femur and or tibia in a fashion that will balance the loads on the implant through all ranges of motion while maintaining optimal implant positioning.

Figure 88:
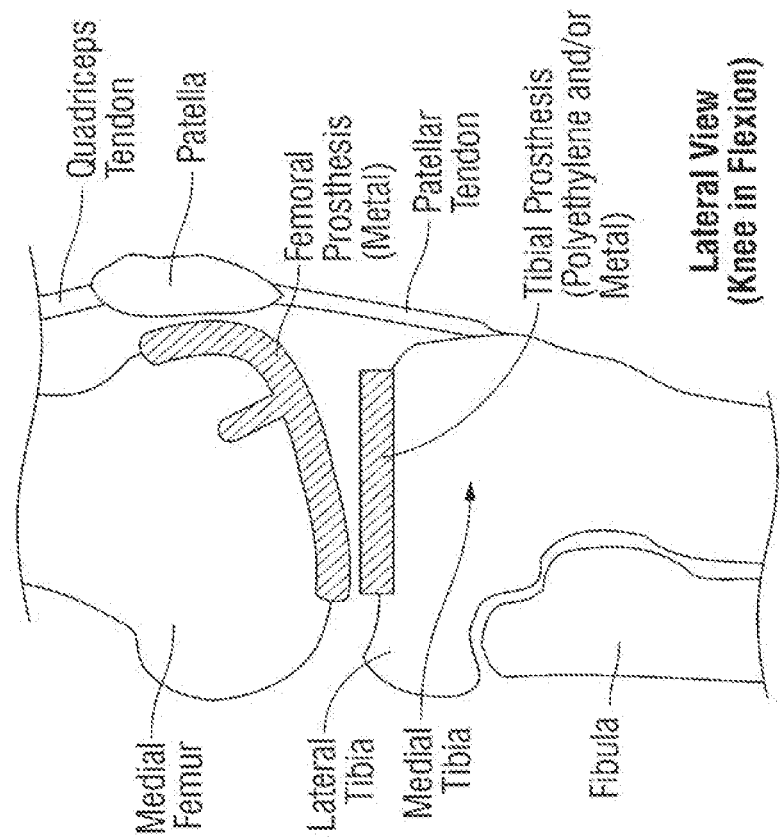
FIG. 88 is a fragmentary side elevational view of the medial knee implant of FIG. 87.
Figure 87:
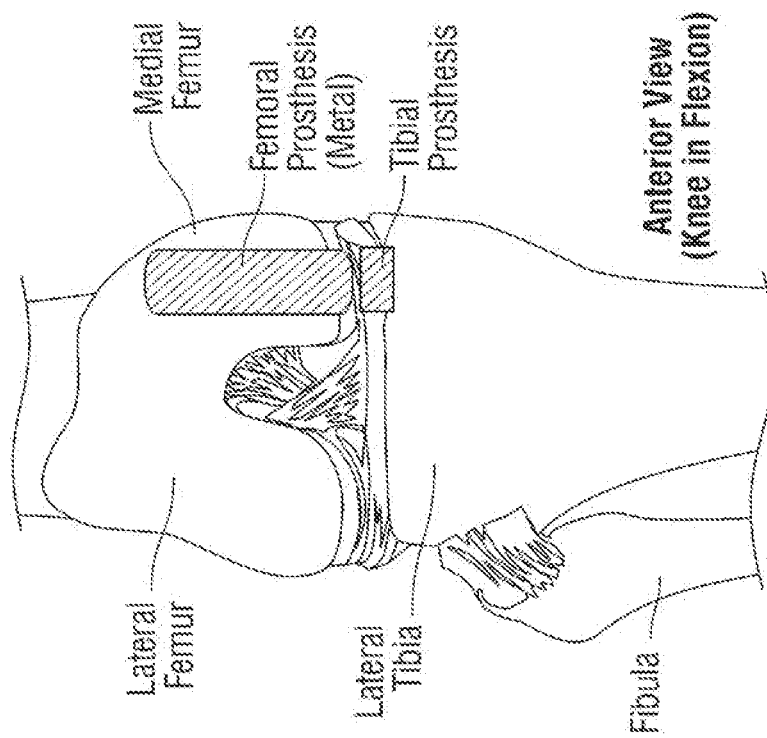
FIG. 87 is a fragmentary front elevational view of an exemplary embodiment of a medial knee implant according to the invention in flexion.
Figure 89:
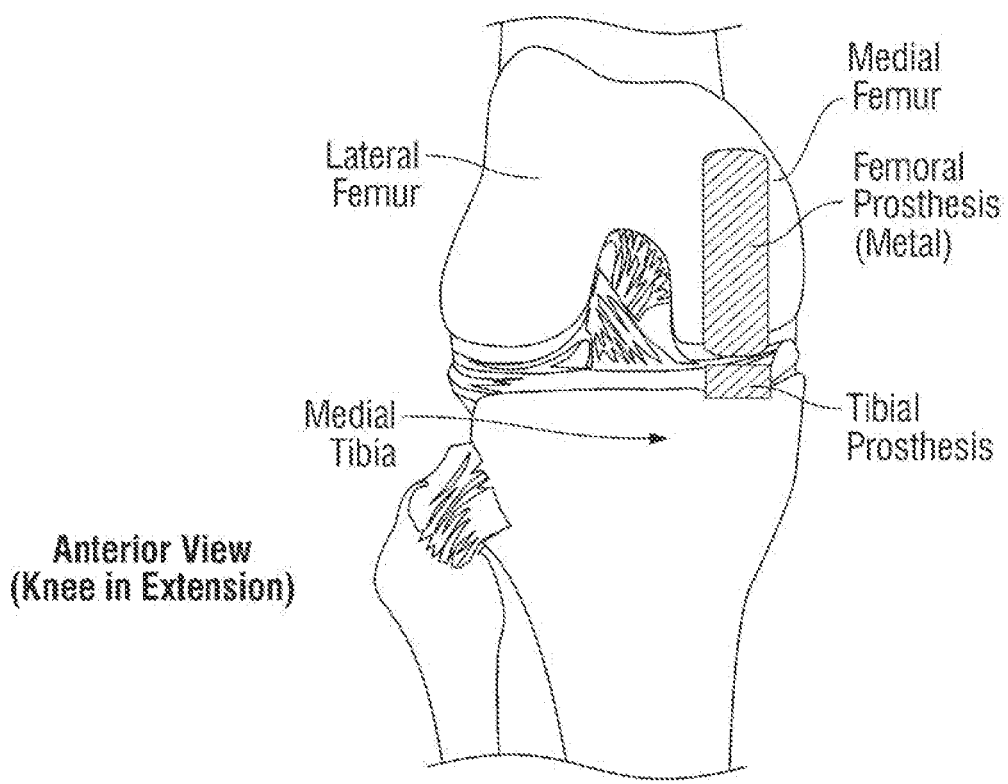
FIG. 89 is a fragmentary front elevational view of the medial knee implant of FIG. 87 in extension.
Figure 90:
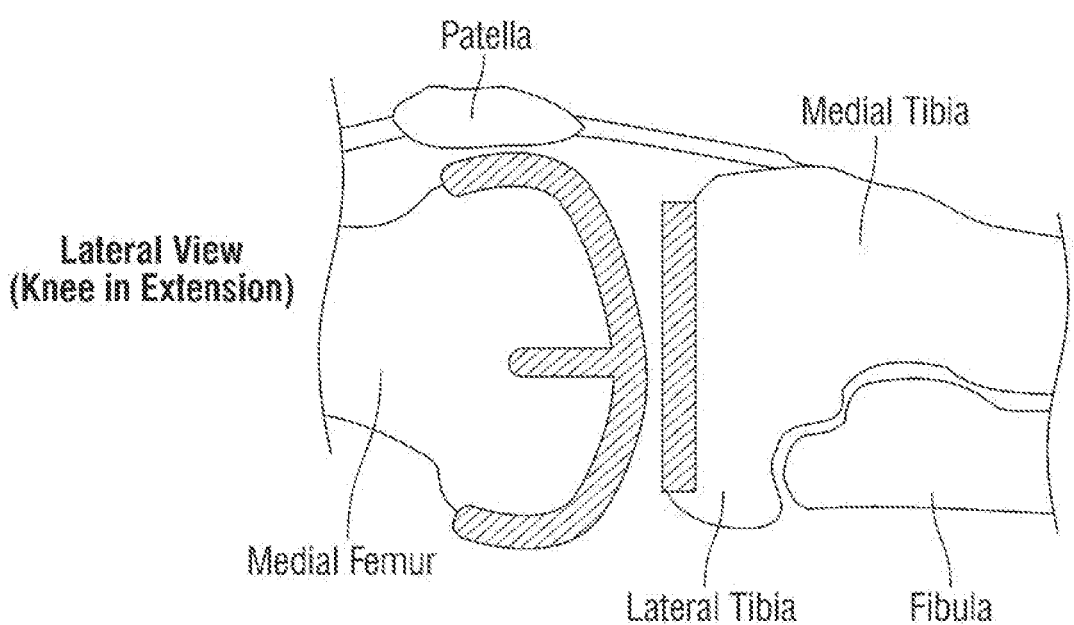
FIG. 90 is a fragmentary top plan view of the medial knee implant of FIG. 87 in extension.

FIGS. 87 to 100 are referenced with regard to this exemplary embodiment of the sensor system. FIGS. 87 and 88 illustrate a medial knee implant, which is made of a metal femoral prosthesis and a plastic and/or metal tibial implant. The implant is bonded to the bone. The flexion gap is shown. FIGS. 89 and 90 illustrate the knee implant in extension. The implant is shown on the medial side of the knee in black. FIGS. 91 and 92 depict the plastic insert that is used to trial the implant. The tibia is cut and then the tibial trial is used to determine the loads when the trial articulates through a range of motion on the natural femur. The sensors reside in the trial insert and, as loads are applied, the sensors detect them. FIG. 93 shows the transmission of load information from the trial insert in a wireless fashion. The insert houses the sensing system and the powering source and transmitter. The handle to insert the trial houses the transmitter and powering system. This information is received and processed. The information is then sent to a monitor for visual inspection. The information allows the surgeon to adjust his/her plans. The proposed change in bone cuts will be depicted in relationship to how it will affect the pre-operative planning of implant alignment. Another option exists, whereby information is sent to a "smart instrument". Such an instrument can be a mounted robotic arm or a free instrument. The smart instrument processes the information and modifies the bone cuts to balance the knee gaps and integrate the optimal component alignment.

Figure 94:
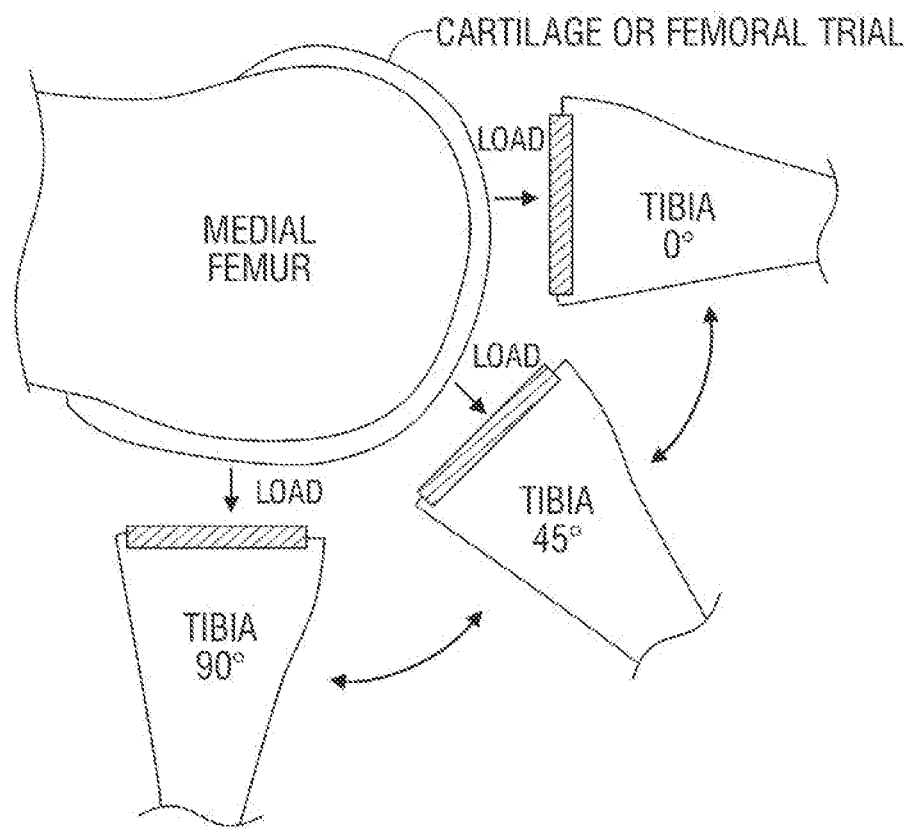
FIG. 94 is a fragmentary side elevational view of a knee as it is taken through a range of motion.
Figure 95:
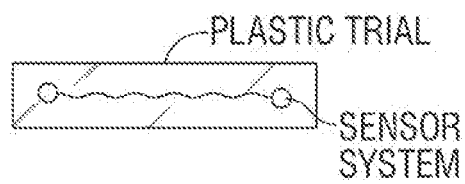
FIG. 95 is a fragmentary elevational view of an exemplary embodiment of a trial plastic insert with embedded sensors according to the invention.
Figure 96:
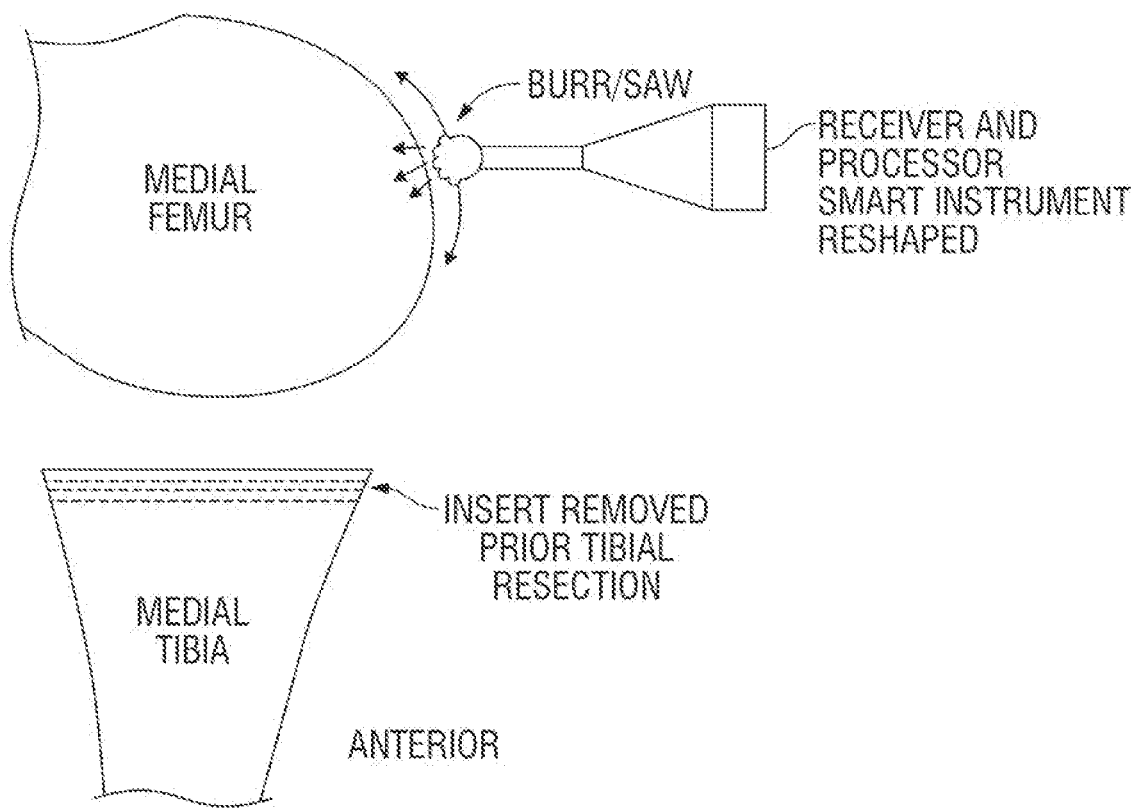
FIG. 96 is a fragmentary side elevational view of an exemplary embodiment of a smart instrument burring cartilage and bone off a femur according to the invention.

FIG. 94 depicts the knee as it is taken through a range of motion. The natural cartilage loads the trial implant. This gives the needed load parameters to determine the femoral cuts and positioning. FIG. 95 shows the plastic trial with the embedded sensors. FIG. 96 illustrates the "smart instrument" burring/cutting the appropriate pre-determined amount of cartilage and bone off the femur for optimal femoral implant placement that achieves optimal component alignment and balanced gaps.

FIGS. 97 and 98 depict the final implant that has been inserted. The final tibial insert has an embedded sensor system that will give post-operative information to the surgeon regarding any parameter that is needed. Examples includes load, wear, abnormal motion, etc. FIGS. 99 and 100 depict the final tibial insert with the embedded sensors.

This exemplary sensor system describes its use in a medial unicompartmental knee replacement. It can be used in lateral or patello-femoral implants. It can be used in Total Knee Implants. It can be used in any other orthopedic implant that is placed in the body to aid in optimal component placement and soft tissue balance of the joint.

Sensors 6606 measure the loading in each compartment for the depth or thickness of the selected spacer block or the distracted gap generated by distractor 6604. In one exemplary embodiment, the loading measurements are taken after the initial bone cuts are determined to be within a predetermined range of alignment with the mechanical axis. The load measurement in each compartment is either high, within an acceptable predetermined range, or low. A load measurement above a predetermined range can be adjusted by removing bone material, selecting a thinner spacer block, adjusting the gap of distractor 6604, or by soft tissue release. In general, the gap between the femur and the tibia at which the measurement taken corresponds to a final insert thickness. In one embodiment, the gap is selected to result in a load measurement on the high side of the predetermined range to allow for fine-tuning through soft tissue release. Conversely, a load measurement below the predetermined range can be increased using the next thicker spacer block or by increasing the gap of distractor 6604. Data from sensors 6606 is transmitted to processing unit 6622. Processing unit 6622 processes the data and displays the information on display 6624 for use by the surgeon to aid in fine-tuning. Display 6624 would further provide positional information of the femur and tibia. The absolute loading in each compartment is measured and displayed on display 6624. As is known by one skilled in the art, the gap created by the bone cuts accommodates the combined thickness of the femoral implant, the tibial implant, and the insert. The gap using spacer blocks 6602 or distractor 6604 takes into account the combined thickness of the implant components. In a non-limiting example, the gap is chosen based on the availability of different thicknesses of the final insert. Thus, the loading on the final or permanent insert placed in the joint will measure within the predetermined range as prepared by using system 6600.

Balance is a comparison of the load measurement of each condyle surface. In general, balance correction is performed when the measurements exceed a predetermined difference value. Soft tissue balancing is achieved by loosening ligaments on the side of the compartment that measures a higher loading. In one embodiment, system 6600 allows the surgeon to read the loading measurement for each compartment on one or more displays on spacer blocks 6602 or distractor 6604. Another factor is that the difference in loading can be due to surface preparation of the bony cuts for either femoral implant or the tibial implant. If the differential is substantial, the surgeon has the option of removing bone on either surface underlying the implant to reduce the loading difference.

In one exemplary embodiment, the absolute load adjustments and balance adjustments are performed by soft tissue release in response to the assessment of each compartment. Load and balance adjustment is achieved with the selected spacer block or distractor 6604 in the knee joint. Spacer blocks 6602 and distractor 6604 have a gap to provide peripheral access between the superior and inferior surfaces of the device, thereby giving the surgeon access to perform soft tissue release to either compartment with real-time load measurement shown on display 6624. In at least one exemplary embodiment, handles 6612 of spacer blocks 6602 or handle 6632 of distractor 6604 can be removed or positioned. Handles 6612 or handle 6632 can be positioned away from the surgical area or removed allowing the surgeon access to perform soft tissue release. The soft tissue release is performed to each compartment to adjust the absolute loading within the predetermined range, and further adjustment can be performed to reduce the differential loading between the compartments to within a predetermined differential range. Consequently, the surgical outcome is a function of system 6600 as complemented with the surgeon's abilities but is not so highly dependent alone on the surgeon's skill. The device captures the "feel" of how an implanted device should properly operate to improve precision and minimize variation including haptic and visual cues.

A similar process is applied with the lower leg in flexion with tibia forming a ninety degree angle with the femur. In one exemplary embodiment, one or more bone cuts are made to the distal end of femur for receiving the femoral implant. The preparation of the femur corresponds to the leg in extension. As disclosed above, the selected spacer block or distractor 6604 can be coupled using an uprod from handle 6612 or handle 6632 to cutting block to aid in alignment and stability. In particular, the surface of the distal end of femur is cut parallel to the prepared surface of the tibia with the leg in flexion. The bone cut to the femur yields an imaginary rectangle formed with the parallel surfaces of femur and tibia when the leg is in extension. It should be noted that a portion of the femoral condyle is in contact with the selected spacer block or distractor 6604 with the leg in flexion and this region is not prepared at this time. In a subsequent step, the remaining surface of the distal end of the femur is prepared. The width of the gap in extension and in flexion between the cut distal end of the femur and the prepared tibia surface corresponds to the thickness of the combined orthopedic implant device comprising the femoral implant, final insert, the tibial implant. Ideally, the measured the gap under equal loading in flexion (i.e., the tibia forms a 90 degree angle with the femur) and extension is similar or equal. The prepared femoral surfaces and the prepared tibial surfaces are parallel throughout the range of motion and perpendicular to the mechanical axis of the leg.

Load measurements are made with the leg in flexion and the selected spacer block or distractor 6604 between the distal end of the femur and the tibial surface. In a non-limiting example, the measurements as described above should be similar to the measurements made in extension. Adjustments to the load value and the balance between compartments can be made by soft tissue release or femoral component rotation in flexion with the selected spacer block or distractor 6604 in place. Alternatively, the femoral implant can be seated on the distal end of the femur and measurements taken. Adjustments can be made with the femoral implant in place. Furthermore, a gap generated by distractor 6604 can be adjusted to accommodate differences due to the femoral implant if required.

The leg with the selected spacer block or distractor 6604 can be taken through a complete range of motion. The loading in each compartment can be monitored on display 6624 and processed by processing unit 6622 over the range of motion. Processing unit 6622 can compare different points in the range of motion to the predetermined load range and the predetermined differential load range. Should an out-of-range-value condition occur, the surgeon can view and note the position of the femur and tibia position on display 6624 and take steps to bring the implant within specification. The surgeon can complete the implant surgery having knowledge that both qualitative and quantitative information was used during the procedure to ensure correct installation. In one exemplary embodiment, sensors 6606, disposable targets 6610, and lasers 6614 are disposed of upon completion of the surgery.

Thus, the sensors will enable the surgeon to measure joint loading while utilizing soft tissue tensioning to adjust balance and maximize stability of an implanted joint. Similarly, measured data in conjunction with positioning can be collected before and during surgery to aid the surgeon in ensuring that, the implanted device has an equivalent geometry and range of motion.

Figure 44:
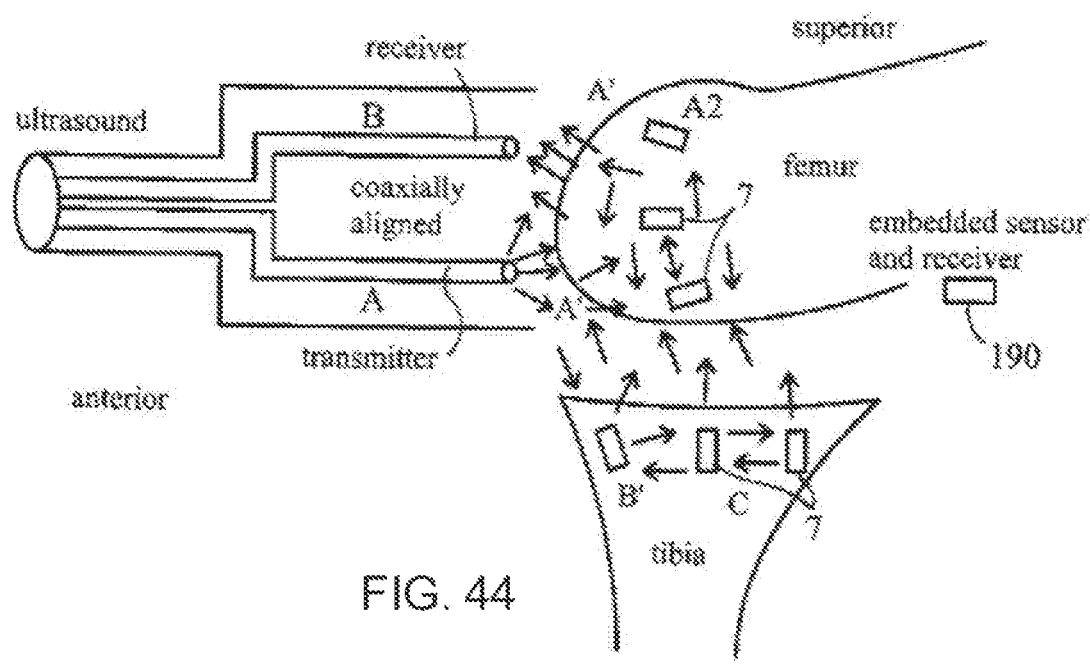
FIG. 44 is a diagrammatic, fragmentary cross-sectional view of a knee joint with ultrasound active sensors according to the invention.
Figure 45:
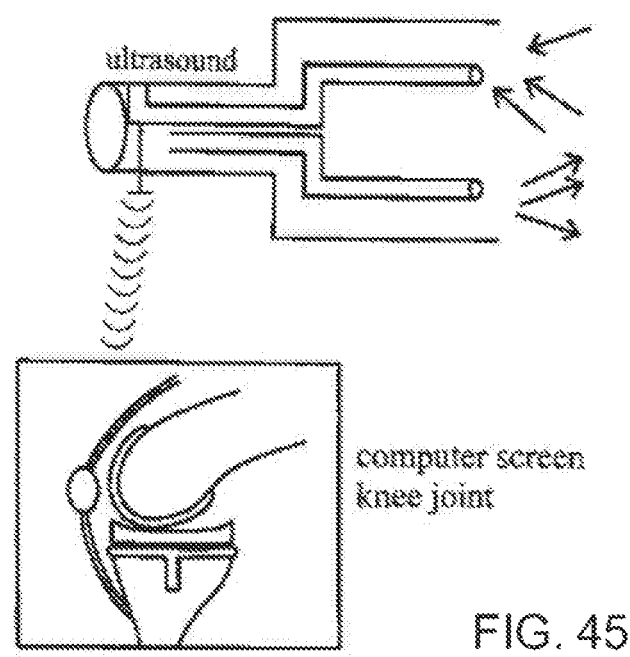
FIG. 45 is a diagrammatic illustration of an ultrasound transmitter and a computer screen showing a knee joint with ultrasound active sensors according to the invention being treated.

Sensors and leads according to the invention can be installed in a variety of ways. One exemplary embodiment employs an ultrasonic cannula system 180, which allows external non-radiating visualization of the sensor placement, and is shown in FIG. 67. The cannula 181 houses the transmitter 182 and the receiver 183. The deployment sensor 184 is, then, optimally positioned for insertion. The ultrasonic arm can, then, be used to obtain a rapid topography of the joint surface and depth. The ultrasonic inserter sends energy waves to the multiple embedded sensors 7 that reflect to one another and back to the ultrasonic transducer as shown in FIG. 44, FIG. 44 depicts the ultrasonic sensors 7 using reflection techniques with the sound wave. The sound waves reflect off the end of the bone and the embedded sensor 7 back to the receiver in the ultrasonic inserter. The receiver detects the reflected sound waves and activates the sensor output to a computer screen for visualization as shown in FIG. 45.

The ultrasonic wave also exhibits a thru-beam to the tibia. Here, the transmitter beams the ultrasonic wave to a separate receiver 190. The femur/tibia deflect the beam triggering the receiver output. The added ability of the embedded sensors 7 to continually reflect the ultrasonic beam to the network of sensors 7 allows precise three-dimensional information. The sensor 7 is programmed to compensate for irregular surfaces and variable surface temperature. The measurement of bone is based on the processing of the received ultrasound signals. Speed of the sound and the ultrasound velocity both provide measurements on the basis of how rapidly the ultrasound wave propagates through the bone and the soft tissue. These measures characteristics permit creation of a rapid three-dimensional geometry, which information can be externally sent to the computer system that will allow integration of the prosthesis as shown in FIG. 45.

Figure 72:
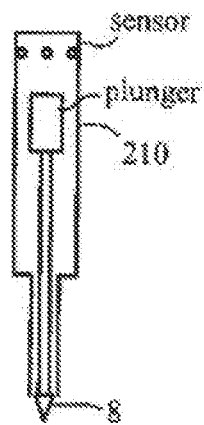
FIG. 72 is a fragmentary, cross-sectional view of a trocar tip according to the invention housing sensor elements.

In order for the sensor system to obtain the needed information regarding the spatial three dimensional topography of the joint, a minimum of three sensors are needed to be implanted into each bone that is an integral part of the joint. Deployment of the sensor can be by a single cannula (FIG. 68) with one or several sensors (FIG. 69), or by a multiple sensor deployment cannula (FIG. 70). The sensor has a calibrated trocar that penetrates skin, muscle, ligament, tendon, cartilage and bone. FIG. 71, for example, depicts the deployment of the sensors in an open knee surgery where the soft tissue has been excluded and the cartilage and bone cuts have been made. A handle 190 houses a plunger 191 that controls the depth of sensor deployment. See FIGS. 72 to 75. The minimal depth is determined by the amount of cartilage and bone to be cut for the implantation of the prosthesis or implant. For example, in the femur and tibia, a minimum of 10 to 15 millimeters is cut. The sensor is deployed deep with respect to that cut so as not to be dislodged during the procedure and to be able to be used in the post-operative period. The trocar tip houses the elements of the sensor (FIG. 72) and, upon reaching the desired depth of deployment, the sensor 8 is inserted by a release of the locking mechanism (FIG. 46), which, for example, can be a screw, or a rotate-to-unlock joint, a break-away, or any other decoupling mechanism.

Figure 32:
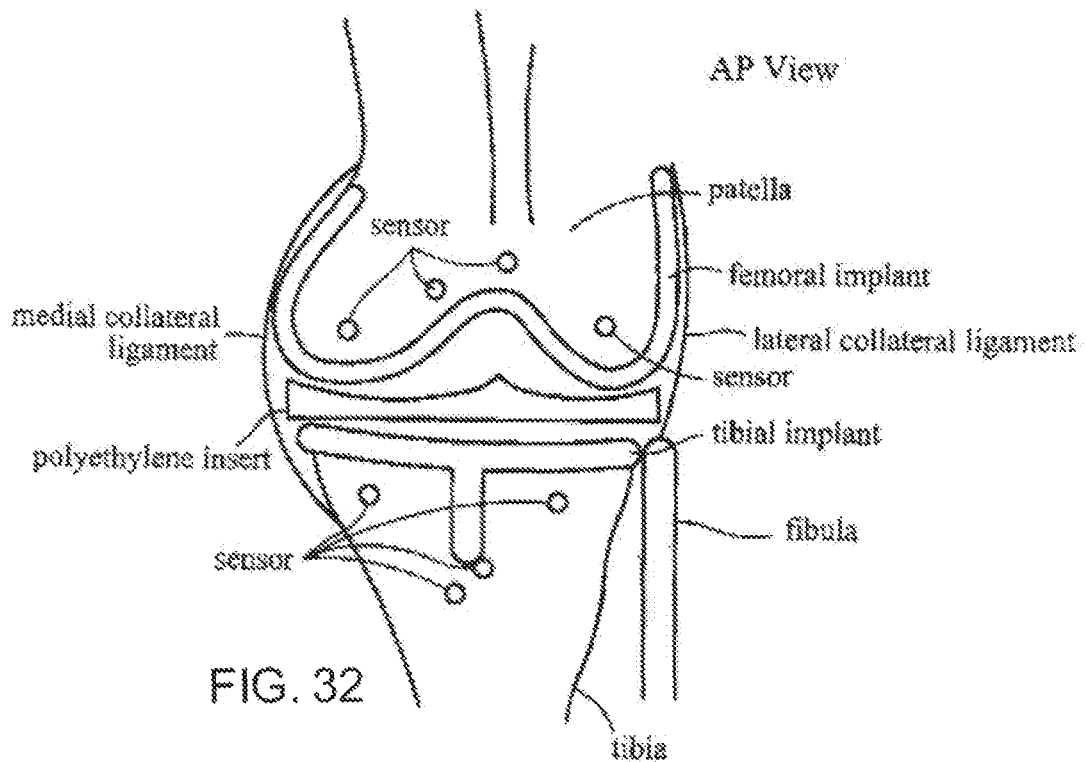
FIG. 32 is a diagrammatic, fragmentary, anterior-posterior, cross-sectional view of a knee joint with sensors according to the invention.
Figure 33:
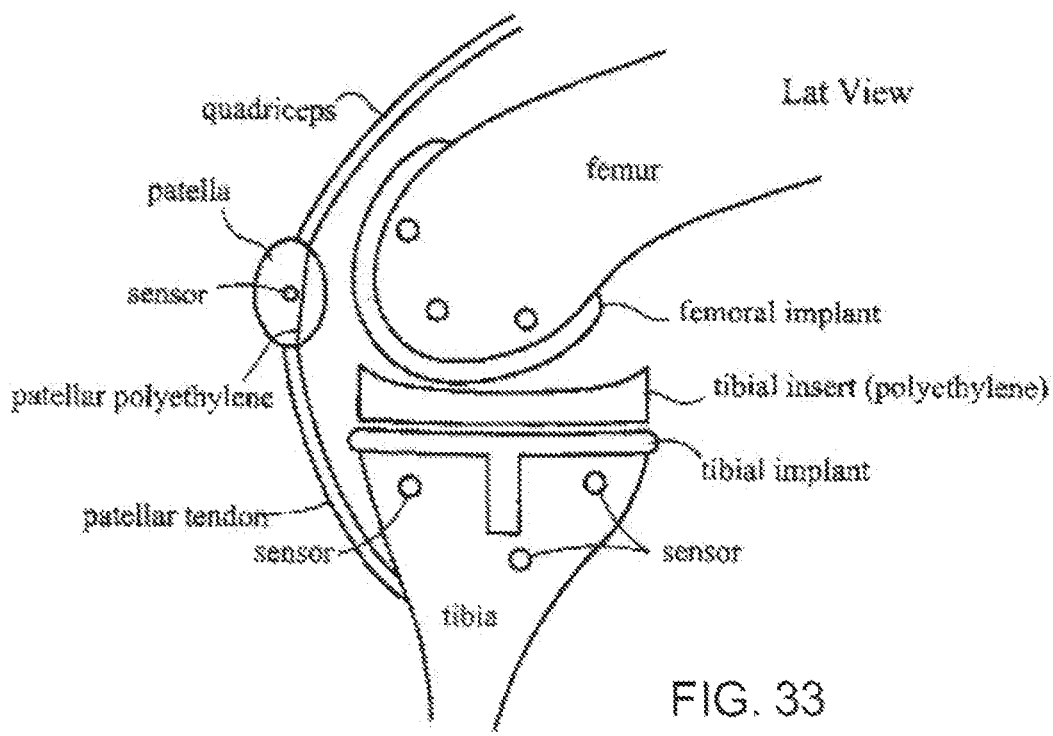
FIG. 33 is a diagrammatic, fragmentary lateral, cross-sectional view of a knee joint with sensors according to the invention.

Once the sensor system has been inserted, the external energy wave that will be used can be ultrasonic or electromagnetic. The use of an optical array method could, therefore, be avoided. The deflection of the energy through the various mediums (cartilage and bone) and the time element of the energy wave is received by the sensors 8 and/or reflected back to the external receiver. By having the various sensors 8, a three-dimensional model is depicted. This enables the surgeon to embed the sensors (FIG. 71), use them during surgery (FIGS. 45, 49) and, then, leave them implanted to be utilized after surgery (FIGS. 32 and 33). Accordingly, the speed of information transmission is greatly increased and processed.

FIGS. 50 and 51 depict some elements of the knee joint soft tissue. The ACL, the PCL, the medial collateral ligament, and the lateral collateral ligament are important for balancing of a knee joint during surgery. In one exemplary embodiment, the sensors are embedded into the ligament of a tendon by a clip mechanism (see FIGS. 52 to 55). The information is received and processed by a software system that is integrated into the computer-assisted joint surgery device and presents a visual analogue of an intra-operative joint (FIG. 49). Ligament tension, pressure, shear, etc, is evaluated. A soft-tissue balancing grid aids in the surgeons approach regarding soft tissue releases and component rotation.

Figure 76:
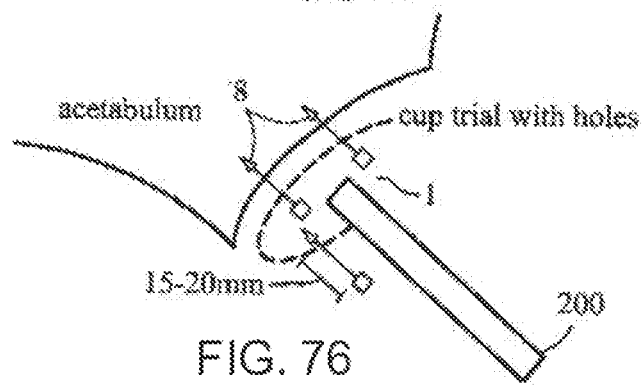
FIG. 76 is a fragmentary, cross-sectional view of a sensor system according to the invention implanted in a hip.
Figure 78:
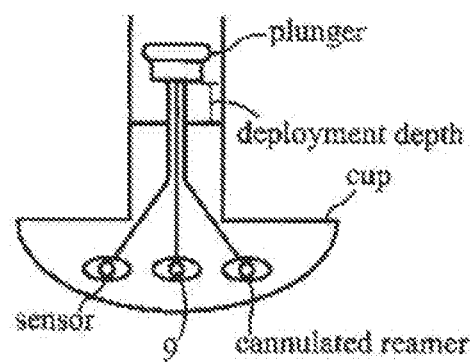
FIG. 78 is a fragmentary, cross-sectional view of a cup sensor inserter according to the invention for deployment of multiple sensors.

FIG. 76 depicts a similar sensor system in the hip. The inserter is similar to a single sensor inserter as shown in FIG. 76 or can be modified as shown in FIG. 76. The inserter is configured to a cannulated acetabular reamer that is used in standard hip surgery. The handle 200 stabilizes the construct and the sensors 8 are deployed by depressing a plunger in the handle 200. FIG. 78 depicts a cup sensor inserter. The cannulated holes allow deployment of the sensor 9. The construct can be modified similar to FIG. 67 to include an ultrasonic component to help visualize the anatomy.

Figure 73:
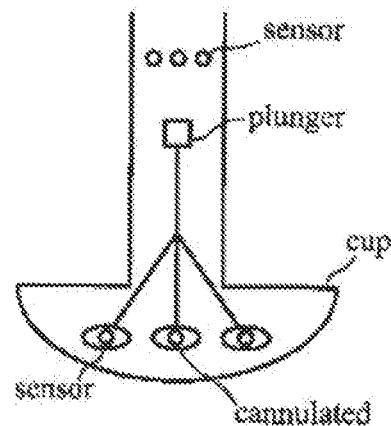
FIG. 73 is fragmentary, cross-sectional view of an inserter for an array of sensors.
Figure 74:
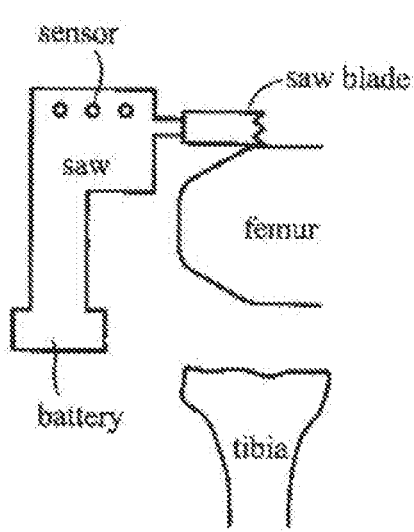
FIG. 74 is diagrammatic, side elevational view of a cutter housing an array of sensors according to the invention.
Figure 75:
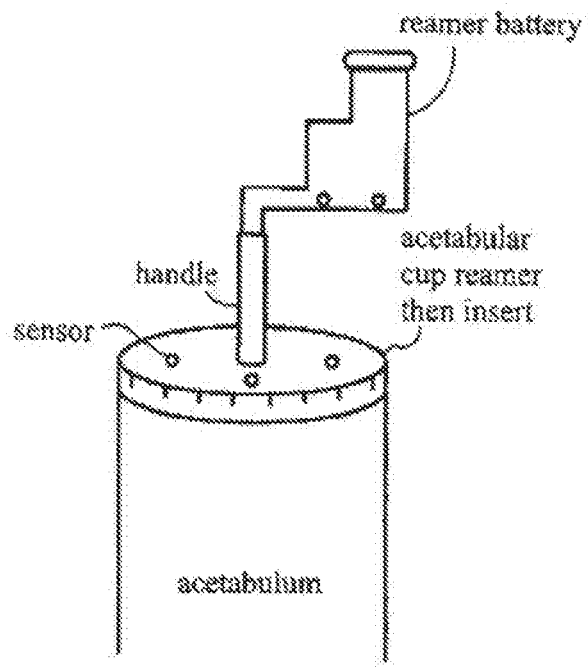
FIG. 75 is a diagrammatic, side elevational view of a bone reamer.

FIGS. 72 to 75 depict the development of "smart" inserters and "smart" instruments. The handle 210 of the inserter/instrument houses an array of sensors 8 to aid in the precise cutting of the bone (FIG. 74) as well as the insertion of the prosthesis and sensors (FIGS. 73 and 75). These sensors 8 are spatially identified by the ultrasonic/electromagnetic transducer and receiver to allow confirmation that the implant/bone interface was prepared appropriately and that the implant was inserted to the appropriate depth and angle. The stability of a cemented or press fit component could, then, be tested. Sensors implanted onto the prosthesis at the time of surgery or prior to surgery also allow precision insertion and orientation of the prosthesis. Post-operative implant evaluation also is performed.

Figure 77:
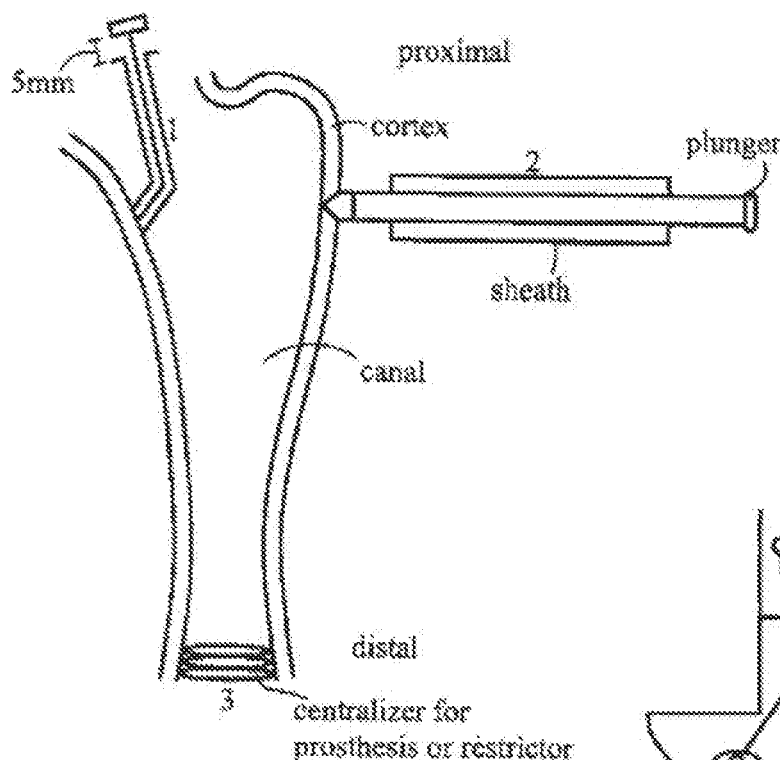
FIG. 77 is a fragmentary, cross-sectional view of a sensor system according to the invention implanted in a femur.

FIG. 77 depicts the insertion of the sensors 8 into a femur. The sensor 8 can be deployed from the inside-out, from the outside-in, or incorporated into the distal centralizer of the prosthesis and or the canal restrictor.

Figure 79:
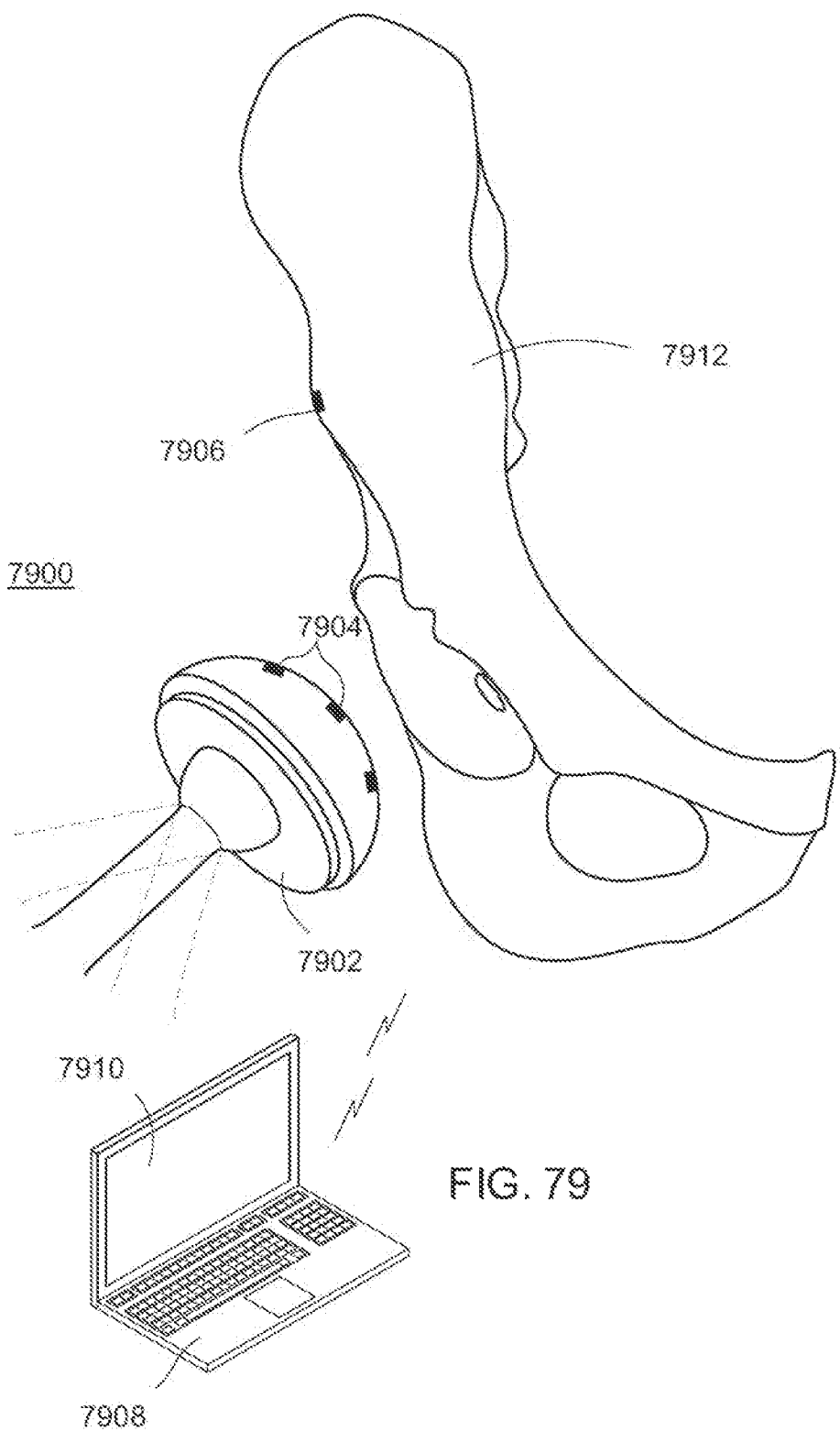
FIG. 79 is a fragmentary, perspective view of an exemplary embodiment of a system having sensor arrays according to the invention.

FIG. 79 is an illustration of a system 7900 having sensor arrays in accordance with an exemplary embodiment. The system disclosed is a non-limiting example used in the installation of an orthopedic device for a hip replacement. The appropriate kinematics of the hip joint is achieved by implant alignment and refined by increasing or decreasing the hips offset or the limb length. One or more sensor arrays 7906 are coupled to the pelvis 7912 and one or more sensor arrays are placed in the femur prior to dislocation of the hip. Sensor arrays 7906 provide position and measurement data on the existing joint that can be compared later to the implanted joint or during refinement of the implant to inform the surgeon of the hip joint function. It is noted that the hip joint sensor integration described here can be utilized in other areas of the skeletal system.

The system comprises one or mote tools and implanted orthopedic devices incorporating sensor arrays in communication with a processing unit 7908. The system measures and displays parameters of the hip joint including load, position, relational positioning, distance, geometry, and other parameters disclosed hereinabove (e.g., with regard to the knee). In general, the damaged portions of the hip joint are replaced. Typically, the femoral head of the femur is removed and the acetabulum is shaped. The acetabulum is a partial spherical shaped bony region in the pelvis 7912 that receives the femoral head. It cannot be understated that the orthopedic implants have an orientation and geometry similar to the original bone structure. This can only be achieved if the implanted orthopedic devices can be oriented correctly (hip to pelvis 7912) with similar physical geometry and symmetry. Incorrect replacement can lead to hip dislocation, one leg being longer or shorter than the other, instability, and other movement difficulties after implantation.

The acetabulum in the pelvis 7912 is shaped with a reaming tool 7902 of the system that removes bony material and cartilage in the region. Reaming tool 7902 includes sensor arrays 7904 that define the varying depths and angles in three planes as the acetabulum is shaped. A trial cup is to be inserted that is similar in size to the patient's natural cup to define the starting angles. Sensor arrays 7906 in the pelvis 7912 define the planes of the pelvis 7912. In at least one exemplary embodiment, sensor arrays 7906 comprise accelerometers. Sensor arrays 7904 and 7906 are in communication with a processing unit 7908. As the reamer is installed, sensor arrays 7904 will maintain the visual positioning the surgeon wants to achieve. This process can be used in cutting instruments/reamers during knee, shoulder, ankle, joint, and/or spine surgery. Processing unit 7908 processes information from reaming tool 7902 and displays positional and shape information of the material removal process on a screen 7910. Once the acetabulum is shaped, the trial cup (socket) is selected to be fitted into the shaped acetabulum.

Typically, an interference fit is used to hold the cup in the acetabulum. A cup is selected that is slightly larger than the opening. Glue can also be used to ensure a secure fit if the surgeon deems it necessary. At this time, the fitting of the cup is difficult because two angles in relation to the pelvis 7912 must be contemplated in the insertion process. In at least one exemplary embodiment, an impaction instrument is fitted with sensors similar to reaming tool 7902 to enable the surgeon to define cup orientation. For example, accelerometers can be used to monitor position and relative positioning of the impaction instrument. In particular, the accelerometers will allow the orientation in at least three planes to achieve appropriate anteversion, opening, and depth.

The impaction instrument fits into a trial cup and includes a handle that can be rotated to direct a force applied to the end of the handle to a specific region of the cup, thereby positioning the cup in the acetabulum. The sensors of the cup impaction instrument are in communication with processing unit 7908. The sensors provide positional information of the impaction instrument (and thereby the trial cup) in relation to the pelvis 7912. Screen 7910 can indicate when the handle is positioned correctly to drive the cup in at the appropriate angles to seat the acetabular cup fully and define full stability. The surgeon can then use a mallet to drive in the cup. In a non-limiting example, a reamer and an impaction tool can be part of the same tool.

Figure 80:
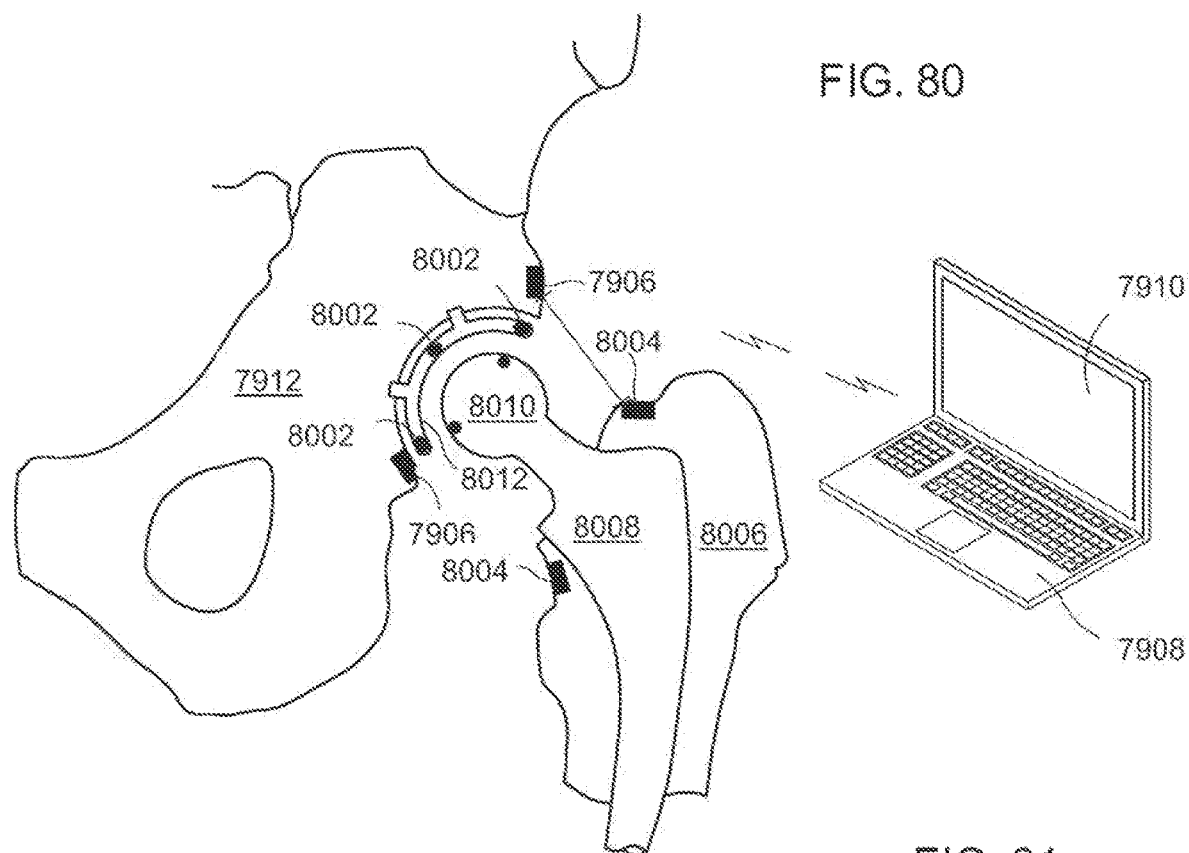
FIG. 80 is a diagrammatic, fragmentary perspective view of a hip implant having sensors according to the invention.

FIG. 80 is an illustration of a hip implant having sensors in accordance with an exemplary embodiment. A proximal end of a femur 8006 has been prepared for receiving a femoral implant 8008. The femoral implant 8008 includes a femoral head 8010 that is fitted into a trial cup 8012. In at least one exemplary embodiment, sensor arrays 8004 are in or attached to femur 8006. The femoral head of the implant can also include sensor arrays. In at least one exemplary embodiment, sensor arrays 8002 are placed in trial cup 8012. Sensors 7906, 8002, and 8004 are in communication with processing unit 7908 for providing location and distance information that is displayed on screen 7910. In particular, the system can make a distance measurement that ensures that femoral implant 8008 results in an appropriate leg length. More specifically, a distance measured between sensors 7906 and sensors 8004 corresponds to a length measured prior to installing femoral implant 8008. The distance of installed femoral implant 8008 should be similar to that of the prior spacing. An incorrect distance can result in a different leg length than the person had originally, which is very noticeable and is a source of complaint by hip replacement patients. The joint offset can also be measured and displayed on screen 7910 using the sensor arrays to display the working hip joint in three-dimensional space. The surgeon can make further adjustments to prevent rework or potential problems at this time based on measurements of the actual implanted joint thereby ensuring the best fit possible.

Figure 81:
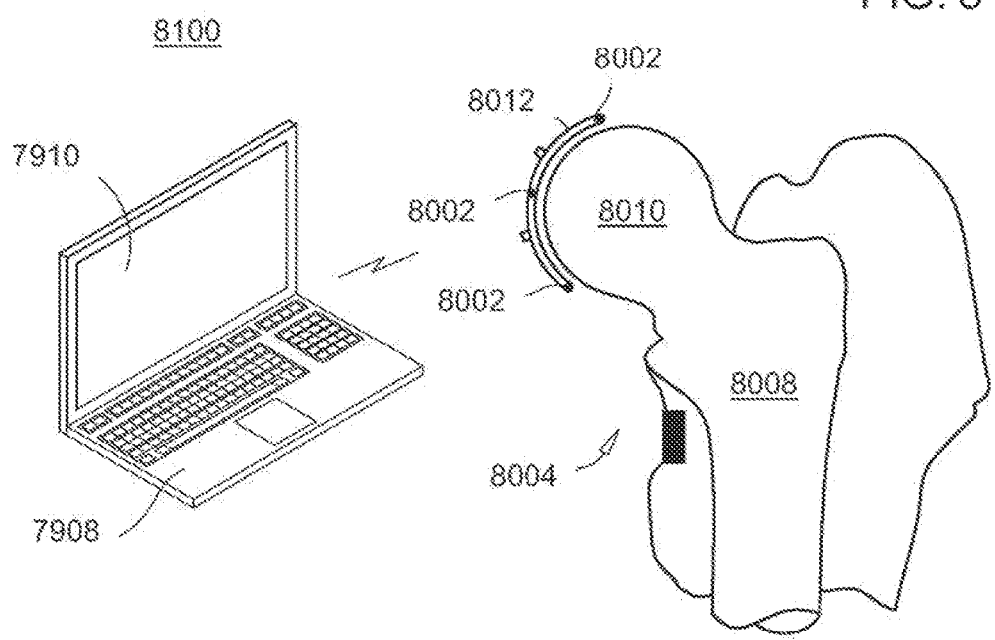
FIG. 81 is a diagrammatic, fragmentary perspective view of a hip implant having load sensors according to the invention.

FIG. 81 is an illustration of a hip implant having load sensors 8002 in accordance with an exemplary embodiment. System 8100 measures appropriate implant and implant articulation. In general, femoral head 8010 of femoral implant 8008 is made of metal that articulates with a polymer or another metal that forms a bearing surface in the acetabulum. If the alignment of the prostheses is not optimal, the implants can impinge on each other leading to edge loading, early implant wear, and dislocation.

As mentioned above, trial cup 8012 includes load sensors 8002. Load sensors 8002 are positioned in different regions of the trial cup and are in communication with processing unit 7908. Once inserted, measurements of the loading in different areas of trial cup 8012 can be made and displayed on screen 7910. The loading measured by sensors 8002 should be within a predetermined range. The cup may not be fully seated if the measurement is outside the range.

Figure 82:
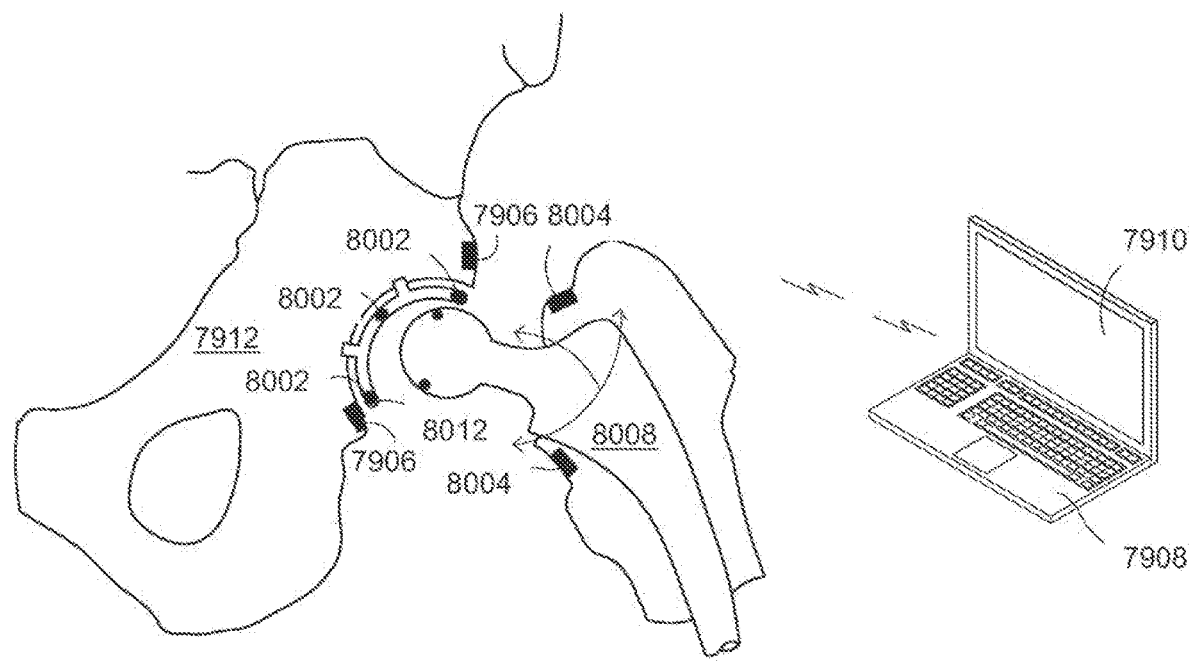
FIG. 82 is diagrammatic, fragmentary perspective view of moving the hip implant to measure load and position through a range of motion according to the invention.

FIG. 82 is an illustration of moving the hip implant to measure, load and position through a range of motion in accordance with an exemplary embodiment. Sensors 7906, 8002, and 8004 provide position and load information to processing unit 7908. The position of the pelvis and hip in relation to each other can be displayed on screen 7910. Load measurements are taken by sensors 8002 on cup 8012 as the hip is moved over the entire range of motion. The surgeon can use the real-time measurements to balance the loading over the range of motion through ligament tensioning and implant positioning. In general, the femoral head 8010 defines that the cup 8012 is fully seated and that femoral head 8010 is equally loading the geometry of cup 8012 as the sensors define the position of the joint. This allows the surgeon to rotate the insert, reposition the cup or femoral implant to achieve optimal implant to implant articulation through all degrees of motion, and define any aspects of instability or overload.

Fine tuning of the implant can be made utilizing the alignment and load measurements in three dimensions. The impaction instrument can be used to make fine adjustments in placement of cup 8012 by positioning the handle and applying a force to move the cup within the acetabulum. The surgeon can be directed to apply the force in an appropriate direction by processing unit 7908 to position cup 8012 using an analysis of the data that is viewed on screen 7910 (e.g., current position versus ideal position). Thus, the system can provide each of alignment, positional, relational positioning, loading, and other measured parameters that aids the surgeon in the installation of cup 8012 and femoral implant 8008 such that it is fitted very accurately, thereby reducing post-operative complications for a patient.

Figure 83:
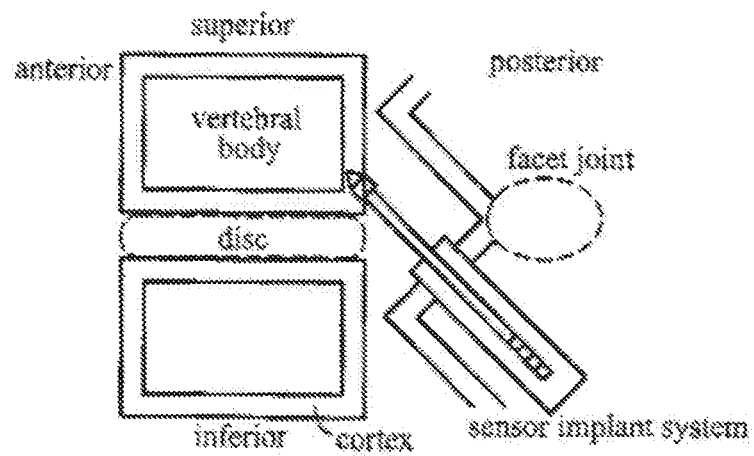
FIG. 83 is a fragmentary, cross-sectional lateral view of two spinal segments with a sensor implantation system according to the invention.
Figure 84:
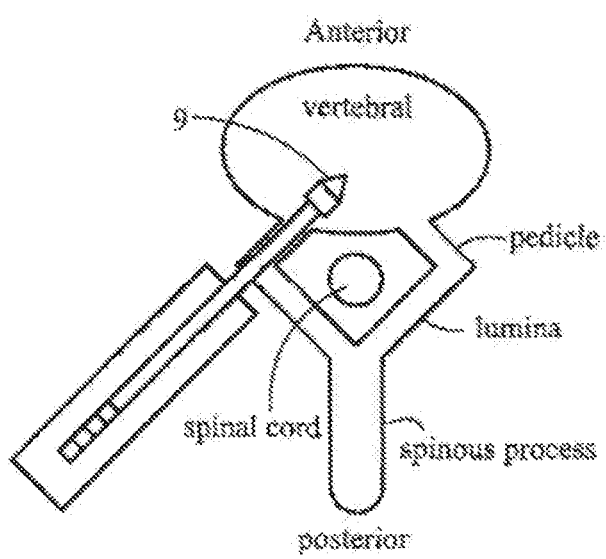
FIG. 84 is a fragmentary, axially cross-sectional view a vertebral level with a sensor implanted through a pedicle.

FIG. 83 depicts the lateral view of two spinal segments. The sensor inserter is shown in a percutaneous manner deploying the sensor into the vertebral body. FIG. 84 depicts an axial view of one vertebral level. The sensor 9 is implanted through the pedicle that has been prepared for instrumentation.

Figure 41:
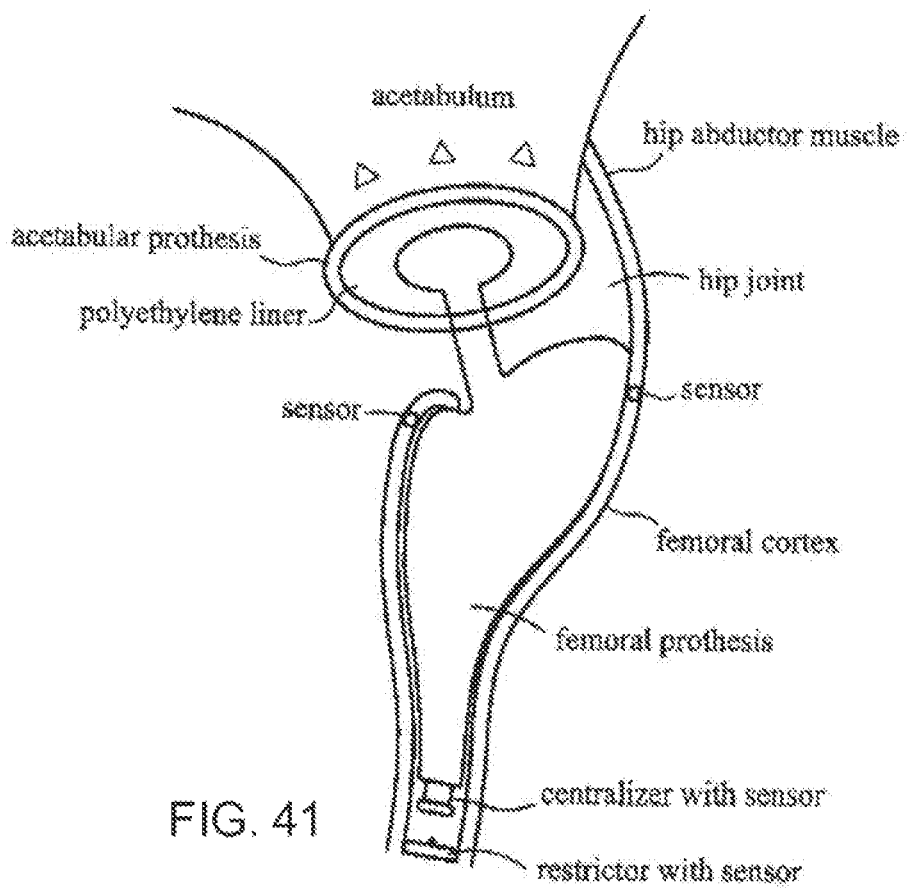
FIG. 41 is a diagrammatic, fragmentary, cross-sectional view of a hip joint with sensors according to the invention.
Figure 42:
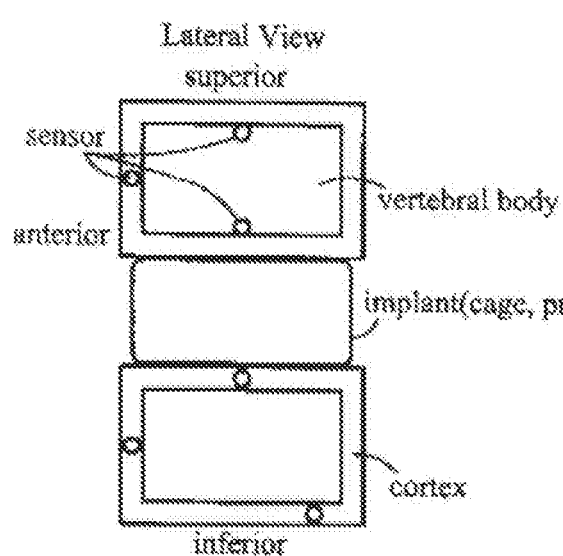
FIG. 42 is a diagrammatic, fragmentary, lateral cross-sectional view of vertebrae with sensors according to the invention.
Figure 43:
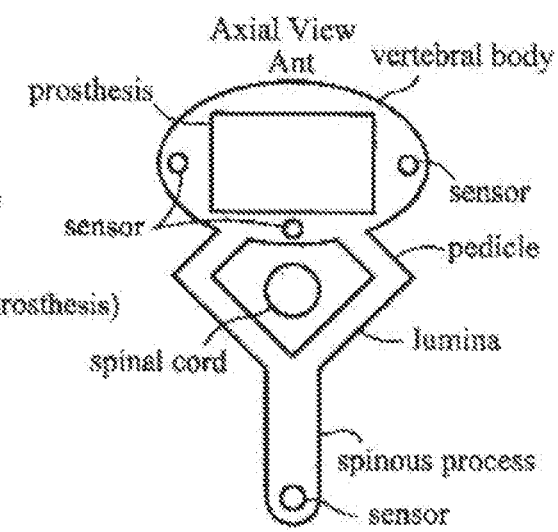
FIG. 43 is a diagrammatic, fragmentary, axial cross-sectional view of a vertebra with sensors according to the invention.

The implanted sensor system following prosthesis insertion is depicted in FIG. 32, an anterior view of the prosthesis, and shows the knee joint, femoral and tibial prostheses, the polyethylene implant, and the embedded sensors. FIG. 33 depicts a lateral view of the knee joint with the prosthesis implanted with sensor system. Likewise, FIG. 41 depicts a total hip prosthesis with the embedded sensor system. FIG. 42 depicts a lateral view of the embedded sensors within two segments of the vertebrae and an implant. FIG. 43 depicts a sensor system within a vertebral body with a superior (axial) view of a prosthesis/implant.

The sensor system of the present invention can be used pre-operatively to follow the progression of joint pathology and the different treatment interventions. The system can be used intra-operatively to aid in the implantation of the prosthesis/instrumentation/hardware. In the spine, affects on the neural elements can be evaluated, as well as the vascular changes during surgery, especially corrective surgery. The sensors can, then, be used post-operatively to evaluate changes over time and dynamic changes. The sensors are activated intra-operatively and parameter readings are stored. Immediately post-operatively, the sensor is activated and a baseline is known.

The sensor system allows evaluation of the host bone and tissue regarding, but not limited to, bone density, fluid viscosity, temperature, strain, pressure, angular deformity, vibration, vascular/venous/lymphatic flow, load, torque, distance, tilt, shape, elasticity, motion, and others. Because the sensors span a joint space, they can detect changes in the implant function. Examples of implant functions include bearing wear, subsidence, bone integration, normal and abnormal motion, heat, change in viscosity, particulate matter, and kinematics, to name a few.

The sensors can be powered by internal batteries or by external measures. A patient could be evaluated in bed at night by a non-contact activation system that can use radio frequency or electromagnetic/ultrasonic energy. The sensor systems' energy signal can penetrate the bed, activate the sensors, and transmit to a receiver that also can be attached to the bed. The sensors can be "upgraded" over time (e.g., with appropriate software enhancements) to evaluate various parameters. The sensors can be modified by an external device, such as a flash drive. For example, a set of embedded sensors can monitor the progression of a spinal fusion that is instrumented. Once a given parameter is confirmed, the same sensors can be m-programmed to monitor the adjacent spinal segments to predict increased stress and, ultimately, subluxation of an adjacent level.

Another feature of the sensor system is that it can rotate through a series of sensor parameters during an evaluation period. An example of such rotation can be evaluation of the bone density as the patient sleeps and, following this, an evaluation of vascular joint fluid viscosity and bearing surfaces. Such evaluation can occur on a fixed time sequence on specific intervals or randomly as desired. The information can be sent telemetrically to the health care provider by current telephonic devices. Likewise, the patient can be evaluated in the doctor's office with an external sensor activator. The patient could, then, go through a series of motions that allow the physician to evaluate implant function, including such parameters as load, tongue, motion, stability, etc.

The software system houses the sensor information in a grid that allows interval comparisons. The physician, then, evaluates the data, and functions that fall outside the standard deviations are highlighted, with these parameters being further evaluated.

Figure 85:
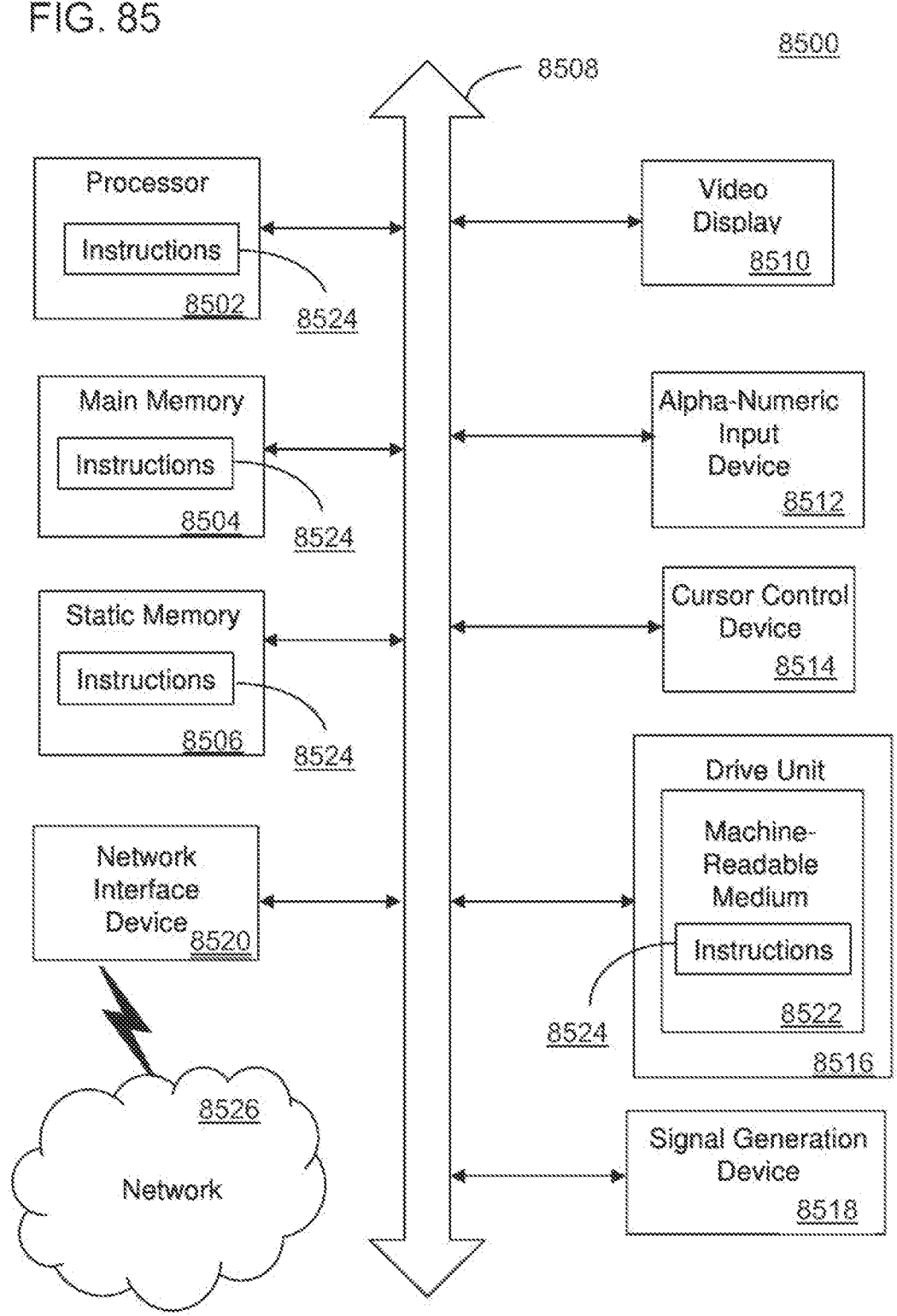
FIG. 85 is a block circuit diagram of an exemplary embodiment of a machine in the form of a computer system according to the invention.

FIG. 85 depicts an exemplary diagrammatic representation of a machine in the form of a computer system 8500 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 8500 may include a processor 8502 (e.g., a central processing unit (CPU), a graphics processing unit (GPU, or both), a main memory 8504 and a static memory 8506, which communicate with each other via a bus 8508. The computer system 8500 may further include a video display unit 8510 (e.g., a liquid crystal display (LCD), a flat panel, a solid state display, or a cathode ray tube (CRT)). The computer system 8500 may include an input device 8512 (e.g., a keyboard), a cursor control device 8514 (e.g., a mouse), a disk drive unit 8516, a signal generation device 8518 (e.g., a speaker or remote control) and a network interface device 8520.

The disk drive unit 8516 may include a machine-readable medium 8522 on which is stored one or more sets of instructions (e.g., software 8524) embodying any one or more of the methodologies or functions described herein, including those methods illustrated above. The instructions 8524 may also reside, completely or at least partially, within the main memory 8504, the static memory 8506, and/or within the processor 8502 during execution thereof by the computer system 8500. The main memory 8504 and the processor 8502 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 8524, or that which receives and executes instructions 8524 from a propagated signal so that a device connected to a network environment 8526 can send or receive voice, video or data, and to communicate over the network 8526 using the instructions 8524. The instructions 8524 may further be transmitted or received over a network 8526 via the network interface device 8520.

While the machine-readable medium 8522 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having substantially the same functions. Accordingly, replacement standards and protocols having the same functions are considered equivalents.

FIG. 86 illustrates a communication network 8600 for measurement and reporting in accordance with an exemplary embodiment. Briefly, the communication network 8600 expands broad data connectivity to other devices or services. As illustrated, the measurement and reporting system 8600 can be communicatively coupled to the communications network 8600 and any associated systems or services.

As one example, the measurement system 8655 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 8600 can further be tied to an Electronic Medical Records (EMR) system to implement health information technology practices. In other embodiments, the communication network 8600 can be communicatively coupled to HIS Hospital Information System. HIT Hospital Information Technology. HIM Hospital Information Management, EHR Electronic Health Record. CPOE Computerized Physician Order Entry, and CDSS Computerized Decision Support systems. This provides the ability of different information technology systems and software applications to communicate, to exchange data accurately, effectively, and consistently, and to use the exchanged data.

The communications network 8600 can provide wired or wireless connectivity over a Local Area Network (LAN) 8601, a Wireless Local Area Network (WLAN) 8605, a Cellular Network 8614, and/or other radio frequency (RE) system. The LAN 8601 and WLAN 8605 can be communicatively coupled to the Internet 8620, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television). Internet services, and so on.

The communication network 8600 can utilize common computing and communications technologies to support circuit-switched and/or packet-switched communications. Each of the standards for Internet 8620 and other packet switched network transmission (e.g., TCP/IP, UDP/IP, HTML, HTTP, RTP, MMS, SMS) represent examples of the state of the art. Such standards are periodically superseded by faster or more efficient equivalents having substantially the same functions. Accordingly, replacement standards and protocols having the same functions are considered equivalent.

The cellular network 8614 can support voice and data services over a number of access technologies such as GSM-GPRS, EDGE. CDMA, UMTS, WiMAX, 2G, 3G, 4G, WAP, software defined radio (SDR), and other known technologies. The cellular network 8614 can be coupled to base receiver 8610 under a frequency-reuse plan for communicating with mobile devices 8602.

The base receiver 8610, in turn, can connect the mobile device 8602 to the Internet 8620 over a packet switched link. The Internet 8620 can support application services 8650 and service layers for distributing data from the measurement system 8655 to the mobile device 8602. The mobile device 8602 can also connect to other communication devices through the Internet 8620 using a wireless communication channel.

The mobile device 8602 can also connect to the Internet 8620 over the WLAN 8605. Wireless Local Access Networks (WLANs) provide wireless access within a local geographical area. WLANs are typically composed of a cluster of Access Points (APs) 8604 also known as base stations. The measurement system 8655 can communicate with other WLAN stations such as laptop 8603 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc).

By way of the communication network 8600, the measurement system 8655 can establish connections with a remote server 8630 on the network and with other mobile devices for exchanging data. The remote server 8630 can have access to a database 8640 that is stored locally or remotely and which can contain application specific data. The remote server 8630 can also host application services directly, or over the internet 8620.

It is noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study, it does yield substantive data about the initial installation, post-operative use, and long-term use from a measurement perspective. Just as each person is different, each device installation is different having variations in initial loading, balance, and alignment. Having measured data and using the data to install an orthopedic device will greatly increase the consistency of the implant procedure, thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Even though these sensor systems are discussed herein mainly with respect to the knee, hip, and spine, these systems can be applied to any of the skeletal systems in the body.

Use of the system has been explained in the description of the present invention for a musculoskeletal sensor system. It

I claim:

1. An implant screw, comprising:
a body portion including a proximal body portion, a distal body portion, and an intermediate body portion extending between the proximal body portion and the distal body portion;
a head portion disposed on the proximal body portion;
threads disposed on the distal body portion; and
a plurality of sensors embedded within the body portion;
wherein the intermediate body portion is configured to span a fracture site when the implant screw is inserted into a bone,
wherein a first sensor of the plurality of sensors is embedded within the proximal body portion and the first sensor is configured to be positioned at a first side of the fracture site when the implant screw is inserted into the bone,
wherein a second sensor of the plurality of sensors is embedded within the distal body portion, the intermediate body portion is positioned between the first sensor and the second sensor, and the second sensor is configured to be positioned at a second side of the fracture site when the implant screw is inserted into the bone, and
wherein the first and second sensors are ultrasonic sensors configured to measure motion detected at the fracture site, and
wherein the first sensor and the second sensor are configured to communicate with one another.

2. The implant screw of claim 1, wherein at least one sensor of the plurality of sensors comprises a strain gauge, wherein the strain gauge measures load.

3. The implant screw of claim 1, wherein at least one sensor of the plurality of sensors is a position sensor.

4. The implant screw of claim 1, wherein at least one sensor of the plurality of sensors is a fracture site motion sensor or an implant motion sensor.

5. The implant screw of claim 1, wherein at least one sensor of the plurality of sensors is a bone density sensor.

6. The implant screw of claim 1, wherein at least one sensor of the plurality of sensors is a viscosity sensor, a blood flow sensor, or a metabolic factor sensor.

7. The implant screw of claim 1, further comprising a control circuit, communication circuitry, and a power source.

8. The implant screw of claim 1, wherein at least one sensor of the plurality of sensors is a microelectromechanical sensor (MEMS).

9. The implant screw of claim 1, wherein the implant screw may communicate with at least one other implanted sensor.

10. The implant screw of claim 1, wherein at least one sensor of the plurality of sensors may be remotely activated.

11. An implant screw comprising:
a body portion including external screw threads at a distal portion of the body portion;
a head portion disposed on a proximal end of the body portion;
a control circuit;
communication circuitry;
a battery; and
a plurality of sensors including a first sensor embedded in the distal portion of the body portion and a second sensor embedded in the body portion, wherein the first sensor is an ultrasonic sensor configured to detect abnormal motion at a fracture site spanned by the implant screw by communicating with the second sensor using an energy wave.

12. The implant screw of claim 11, wherein the ultrasonic sensor is capable of measuring motion between the implant screw and at least one bone.

13. The implant screw of claim 11, further comprising one or more of a viscosity sensor, and/or a blood flow sensor.

14. The implant screw of claim 11, further comprising a strain gauge.

15. An implant screw, comprising:
a body portion;
a head portion disposed on a proximal end of the body portion;
threads disposed on a distal end portion of the body portion; and
a plurality of sensors including (i) a first density sensor within the body portion and (ii) a second density sensor within the body portion and spaced longitudinally from the first density sensor;
wherein the first density sensor and the second density sensor are configured to measure density by sending an energy wave across a fracture site and reflecting the energy wave to one another.

16. The implant screw of claim 15, wherein at least one sensor of the plurality of sensors comprises a strain gauge and/or a microelectromechanical sensor (MEMS).

17. The implant screw of claim 15, wherein at least one sensor of the plurality of sensors is a position sensor.

18. The implant screw of claim 15, wherein at least one sensor of the plurality of sensors is an implant motion sensor and/or a fracture site motion sensor.

19. The implant screw of claim 15, wherein at least one sensor of the plurality of sensors measures bone density by receiving an energy wave from an external source.

* * * * *